United States Patent
Mashiach

(10) Patent No.: US 9,415,216 B2
(45) Date of Patent: *Aug. 16, 2016

(54) DEVICES FOR TREATMENT OF SLEEP APNEA

(71) Applicant: Nyxoah SA, Mont-St-Guibert (BE)

(72) Inventor: Adi Mashiach, Tel Aviv (IL)

(73) Assignee: NYXOAH SA, Mont-St-Guibert (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/884,977

(22) Filed: Oct. 16, 2015

(65) Prior Publication Data
US 2016/0030740 A1    Feb. 4, 2016

Related U.S. Application Data

(63) Continuation of application No. 14/041,598, filed on Sep. 30, 2013, which is a continuation-in-part of application No. 13/629,690, filed on Sep. 28, 2012, and a continuation-in-part of application No.

(Continued)

(51) Int. Cl.
*A61N 1/05* (2006.01)
*A61N 1/36* (2006.01)
*A61N 1/372* (2006.01)

(52) U.S. Cl.
CPC .......... *A61N 1/36003* (2013.01); *A61N 1/0551* (2013.01); *A61N 1/37211* (2013.01)

(58) Field of Classification Search
CPC ..... A61N 1/3787; A61N 1/3601; A61N 1/08; A61N 1/0548; A61N 1/36003; A61N 1/37211; A61N 1/0551

USPC .......................................... 607/61, 134, 118
See application file for complete search history.

(56) References Cited

U.S. PATENT DOCUMENTS

| | | | |
|---|---|---|---|
| 3,796,221 A | 3/1974 | Hagfors | |
| 3,870,051 A | 3/1975 | Brindley | |
| 4,765,983 A | 8/1988 | Takayanagi et al. | |
| 4,830,008 A | 5/1989 | Meer | |

(Continued)

FOREIGN PATENT DOCUMENTS

| | | |
|---|---|---|
| DE | 10 2009027997 | 1/2011 |
| WO | WO2007/098200 | 8/2007 |
| WO | WO2007/098202 | 8/2007 |
| WO | WO2008/048471 | 4/2008 |
| WO | WO2011/077433 | 6/2011 |

OTHER PUBLICATIONS

Maurer, Joachim T., Operative Technique of Upper Airway Stimulation: An Implantable Treatment of Obstructive Sleep Apnea, Operative Techniques in Otolarygology, vol. 23, No. 3, Sep. 2012, pp. 227-233.

(Continued)

*Primary Examiner* — Christopher D Koharski
*Assistant Examiner* — Michael Carey
(74) *Attorney, Agent, or Firm* — Finnegan, Henderson, Farabow, Garrett & Dunner, LLP

(57) ABSTRACT

A method for delivering energy as a function of degree coupling may utilize an external unit configured for location external to a body of a subject and at least one processor associated with the implant unit and configured for electrical communication with a power source. The method may determine a degree of coupling between the primary antenna and a secondary antenna associated with the implant unit, and regulate delivery of power to the implant unit based on the degree of coupling between the primary antenna and the secondary antenna.

8 Claims, 17 Drawing Sheets

Related U.S. Application Data

13/629,694, filed on Sep. 28, 2012, now Pat. No. 8,577,472, and a continuation-in-part of application No. 13/629,701, filed on Sep. 28, 2012, now Pat. No. 8,588,941, and a continuation-in-part of application No. 13/629,712, filed on Sep. 28, 2012, now Pat. No. 9,314,613, and a continuation-in-part of application No. 13/629,725, filed on Sep. 28, 2012, now Pat. No. 8,577,478, and a continuation-in-part of application No. 13/629,730, filed on Sep. 28, 2012, now Pat. No. 8,577,465, and a continuation-in-part of application No. 13/629,741, filed on Sep. 28, 2012, now Pat. No. 8,577,466, and a continuation-in-part of application No. 13/629,748, filed on Sep. 28, 2012, now Pat. No. 8,700,183, and a continuation-in-part of application No. 13/629,757, filed on Sep. 28, 2012, now Pat. No. 9,302,093, and a continuation-in-part of application No. 13/629,762, filed on Sep. 28, 2012, now Pat. No. 8,577,467, and a continuation-in-part of application No. 13/629,793, filed on Sep. 28, 2012, now Pat. No. 8,577,468, and a continuation-in-part of application No. 13/629,819, filed on Sep. 28, 2012, now Pat. No. 8,718,776, and a continuation-in-part of application No. 13/630,392, filed on Sep. 28, 2012, now Pat. No. 8,644,957, and a continuation-in-part of application No. 13/629,721, filed on Sep. 28, 2012, now Pat. No. 8,574,164, and a continuation-in-part of application No. 13/629,686, filed on Sep. 28, 2012, now Pat. No. 8,577,464, which is a continuation-in-part of application No. 12/642,866, filed on Dec. 21, 2009, now Pat. No. 8,585,617, and a continuation-in-part of application No. 12/581,907, filed on Oct. 20, 2009, said application No. 13/629,721 is a continuation-in-part of application No. 12/642,866, and a continuation-in-part of application No. 12/581,907.

(60) Provisional application No. 61/541,651, filed on Sep. 30, 2011, provisional application No. 61/657,424, filed on Jun. 8, 2012.

(56) References Cited

U.S. PATENT DOCUMENTS

| | | | |
|---|---|---|---|
| 4,837,049 | A | 6/1989 | Byers et al. |
| 5,094,242 | A | 3/1992 | Gleason et al. |
| 5,174,287 | A | 12/1992 | Kallok et al. |
| 5,178,156 | A | 1/1993 | Takishima et al. |
| 5,193,539 | A | 3/1993 | Schulman et al. |
| 5,485,851 | A | 1/1996 | Erickson |
| 5,540,733 | A | 7/1996 | Testerman et al. |
| 5,591,216 | A | 1/1997 | Testerman et al. |
| 5,697,076 | A | 12/1997 | Troyk et al. |
| 5,895,360 | A | 4/1999 | Christopherson et al. |
| 5,948,006 | A | 9/1999 | Mann |
| 6,024,702 | A | 2/2000 | Iversen |
| 6,026,818 | A | 2/2000 | Blair et al. |
| 6,038,480 | A | 3/2000 | Hrdlicka et al. |
| 6,051,017 | A | 4/2000 | Loeb et al. |
| 6,126,611 | A | 10/2000 | Bourgeois et al. |
| 6,163,725 | A | 12/2000 | Peckham et al. |
| 6,185,296 | B1 | 2/2001 | Saitoh |
| 6,210,326 | B1 | 4/2001 | Ehwald |
| 6,240,316 | B1 | 5/2001 | Richmond et al. |
| 6,275,737 | B1 | 8/2001 | Mann |
| 6,345,202 | B2 | 2/2002 | Richmond et al. |
| 6,572,543 | B1 | 6/2003 | Christopherson et al. |
| 6,587,725 | B1 | 7/2003 | Durand et al. |
| 6,587,728 | B2 | 7/2003 | Fang et al. |
| 6,625,494 | B2 | 9/2003 | Fang et al. |
| 6,636,767 | B1 | 10/2003 | Knudson et al. |
| 6,643,552 | B2 | 11/2003 | Edell et al. |
| 6,770,022 | B2 | 8/2004 | Mechlenburg et al. |
| 6,814,706 | B2 | 11/2004 | Barton et al. |
| 7,062,330 | B1 | 6/2006 | Boveja et al. |
| 7,155,278 | B2 | 12/2006 | King et al. |
| 7,272,443 | B2 | 9/2007 | Min et al. |
| 7,277,749 | B2 | 10/2007 | Gordon et al. |
| 7,295,132 | B2 | 11/2007 | Steiner |
| 7,367,935 | B2 | 5/2008 | Mechlenburg et al. |
| 7,371,220 | B1 | 5/2008 | Koh et al. |
| 7,447,551 | B2 | 11/2008 | Kuo et al. |
| 7,623,929 | B1 | 11/2009 | Griffith |
| 7,644,714 | B2 | 1/2010 | Atkinson et al. |
| 7,667,511 | B2 | 2/2010 | Staszewski et al. |
| 7,680,538 | B2 | 3/2010 | Durand et al. |
| 7,697,990 | B2 | 4/2010 | Ujhazy et al. |
| 7,709,961 | B2 | 5/2010 | Greenberg et al. |
| 7,725,195 | B2 | 5/2010 | Lima et al. |
| 7,729,772 | B2 | 6/2010 | Williams et al. |
| 7,729,781 | B2 | 6/2010 | Swoyer et al. |
| 7,733,218 | B2 | 6/2010 | Drago et al. |
| 7,756,583 | B2 | 7/2010 | Demarais et al. |
| 7,773,695 | B2 | 8/2010 | Zhou et al. |
| 7,809,442 | B2 | 10/2010 | Bolea et al. |
| 7,845,357 | B2 | 12/2010 | Buscemi et al. |
| 7,869,885 | B2 | 1/2011 | Begnaud et al. |
| 8,072,310 | B1 | 12/2011 | Everhart |
| 8,577,465 | B2 * | 11/2013 | Mashiach ............ A61N 1/0551 607/42 |
| 8,577,467 | B2 | 11/2013 | Mashiach et al. |
| 2001/0018547 | A1 | 8/2001 | Mechlenburg et al. |
| 2002/0188333 | A1 | 12/2002 | Nowick et al. |
| 2003/0225403 | A1 | 12/2003 | Woloszko et al. |
| 2004/0049245 | A1 | 3/2004 | Gass et al. |
| 2004/0059392 | A1 | 3/2004 | Parramon et al. |
| 2004/0085792 | A1 | 5/2004 | Lin et al. |
| 2004/0102820 | A1 | 5/2004 | Moune et al. |
| 2004/0153127 | A1 | 8/2004 | Gordon et al. |
| 2004/0172089 | A1 | 9/2004 | Whitehurst et al. |
| 2004/0199212 | A1 | 10/2004 | Fischell et al. |
| 2005/0010265 | A1 | 1/2005 | Baru Fassio et al. |
| 2005/0043772 | A1 | 2/2005 | Stahmann et al. |
| 2005/0070971 | A1 | 3/2005 | Fowler et al. |
| 2005/0075694 | A1 | 4/2005 | Schmeling et al. |
| 2005/0075695 | A1 | 4/2005 | Schommer |
| 2005/0075697 | A1 | 4/2005 | Olson et al. |
| 2005/0075700 | A1 | 4/2005 | Schommer |
| 2006/0062580 | A1 | 3/2006 | Mahbobi |
| 2006/0114104 | A1 | 6/2006 | Scaramozzino |
| 2006/0145878 | A1 | 7/2006 | Lehrman et al. |
| 2006/0180647 | A1 | 8/2006 | Hansen |
| 2006/0217779 | A1 | 9/2006 | Ransbury et al. |
| 2006/0224211 | A1 | 10/2006 | Durand et al. |
| 2006/0271110 | A1 | 11/2006 | Vernon et al. |
| 2007/0073357 | A1 | 3/2007 | Rooney et al. |
| 2007/0112404 | A1 | 5/2007 | Mann et al. |
| 2007/0150022 | A1 | 6/2007 | Ujhazy et al. |
| 2007/0173893 | A1 | 7/2007 | Pitts |
| 2007/0185546 | A1 | 8/2007 | Tseng et al. |
| 2007/0221231 | A1 | 9/2007 | Macken |
| 2007/0222560 | A1 | 9/2007 | Posamentier |
| 2007/0233204 | A1 | 10/2007 | Lima et al. |
| 2007/0255379 | A1 | 11/2007 | Williams et al. |
| 2007/0265606 | A1 | 11/2007 | DeBenedictis et al. |
| 2007/0290859 | A1 | 12/2007 | Held et al. |
| 2008/0021506 | A1 | 1/2008 | Grocela |
| 2008/0027503 | A1 | 1/2008 | Marrosu et al. |
| 2008/0030363 | A1 | 2/2008 | Rezvani et al. |
| 2008/0041398 | A1 | 2/2008 | Hegde et al. |
| 2008/0081982 | A1 | 4/2008 | Simon et al. |
| 2008/0103407 | A1 * | 5/2008 | Bolea ................... A61N 1/0556 600/529 |
| 2008/0109046 | A1 | 5/2008 | Lima et al. |
| 2008/0109047 | A1 | 5/2008 | Pless |
| 2008/0119911 | A1 | 5/2008 | Rosero |
| 2008/0132962 | A1 | 6/2008 | DiUbaldi et al. |
| 2008/0140152 | A1 | 6/2008 | Imran et al. |
| 2008/0165058 | A1 | 7/2008 | Ayachitula et al. |
| 2008/0243014 | A1 | 10/2008 | Moussavi et al. |

(56) References Cited

U.S. PATENT DOCUMENTS

| | | | |
|---|---|---|---|
| 2008/0300654 | A1 | 12/2008 | Lambert et al. |
| 2008/0319506 | A1 | 12/2008 | Cauller |
| 2009/0048647 | A1 | 2/2009 | Tingey |
| 2009/0062675 | A1 | 3/2009 | Weigand et al. |
| 2009/0069648 | A1 | 3/2009 | Irazoqui et al. |
| 2009/0078274 | A1 | 3/2009 | Bhat et al. |
| 2009/0128262 | A1 | 5/2009 | Lee et al. |
| 2009/0132018 | A1 | 5/2009 | DiUbaldi et al. |
| 2009/0157150 | A1 | 6/2009 | Cauller |
| 2009/0173351 | A1 | 7/2009 | Sahin et al. |
| 2009/0281595 | A1 | 11/2009 | King et al. |
| 2010/0030298 | A1 | 2/2010 | Martens et al. |
| 2010/0087896 | A1 | 4/2010 | McCreery |
| 2010/0094379 | A1 | 4/2010 | Meadows et al. |
| 2010/0114190 | A1 | 5/2010 | Bendett et al. |
| 2010/0121413 | A1 | 5/2010 | Willerton et al. |
| 2010/0125304 | A1 | 5/2010 | Faltys |
| 2010/0131029 | A1 | 5/2010 | Durand et al. |
| 2010/0137948 | A1 | 6/2010 | Aghassian et al. |
| 2010/0139667 | A1 | 6/2010 | Atkinson et al. |
| 2010/0152553 | A1 | 6/2010 | Ujhazy et al. |
| 2010/0191136 | A1 | 7/2010 | Wolford |
| 2010/0196744 | A1 | 8/2010 | Tucholski et al. |
| 2010/0198305 | A1 | 8/2010 | Farbarik |
| 2010/0228313 | A1 | 9/2010 | Starkebaum et al. |
| 2010/0234924 | A1 | 9/2010 | Willis |
| 2010/0241195 | A1 | 9/2010 | Meadows et al. |
| 2010/0292527 | A1 | 11/2010 | Schneider et al. |
| 2010/0312320 | A1 | 12/2010 | Faltys et al. |
| 2010/0331634 | A1 | 12/2010 | Müller et al. |
| 2011/0065979 | A1 | 3/2011 | Lehrman et al. |
| 2011/0071591 | A1 | 3/2011 | Bolea et al. |
| 2011/0093036 | A1 | 4/2011 | Mashiach |
| 2011/0112601 | A1 | 5/2011 | Meadows et al. |
| 2011/0152965 | A1 | 6/2011 | Mashiach et al. |
| 2011/0152966 | A1 | 6/2011 | Bolea et al. |
| 2011/0172733 | A1 | 7/2011 | Lima et al. |
| 2011/0213438 | A1 | 9/2011 | Lima et al. |
| 2011/0230702 | A1 | 9/2011 | Honour |
| 2011/0264163 | A1 | 10/2011 | Tracey et al. |
| 2011/0301670 | A1 | 12/2011 | Gross et al. |
| 2012/0123498 | A1 | 5/2012 | Gross |
| 2014/0107732 | A1 | 4/2014 | Mashiach et al. |

OTHER PUBLICATIONS

Brindley, G.S., Transmission of electrical stimuli along many independent channels through a fairly small area of skin, Proceedings of the Physiological Society, Dec. 1964, pp. 44-46.

Tran W.H., First Subject Evaluated with Simulated BION Treatment in Posterior Genioglossus to Prevent Obstructive Sleep Apnea, Proceedings of the 26th Annual International Conference of IEEE EMBS, Sep. 2004, pp. 4287-4289.

Schwartz, Alan R., Therapeutic Stimulation of the Hypoglossal Nerve in Obstructive Sleep Apnea, Archives of Otolaryngology Head and Neck Surgery, vol. 127, Oct. 2001, pp. 1216-1223.

Eastwood, P.R. Treatment of Obstructive Sleep Apnea with Unilateral Hyopglossal Nerve Stimulation, American Journal of Respiratory Critical Care Medicine, vol. 181, May 2010, pp. 5393-5394.

Eisele, David W., Tongue neuromuscular and direct hypoglossal nerve stimulation for obstructive sleep apnea, Otolaryngologic Clinics of North America, Jun. 2003, pp. 501-510.

Robblee, L.S., Studies of the electrochemistry of stimulating electrodes, National Institutes of Health, Contract No. N01-NS-8-2313, Nov. 1991, pp. 6-8.

Levin, Morris, Nerve Blocks in the Treatment of Headaches, Neurotherapeutics: The Journal of the American Society for Experimental Neuro Therapeutics, Apr. 2010, pp. 197-203.

Lundy, Larry, Ear, Nose, and Throat Journal, Cochlear Implant Fixation Using Resorbable Mesh, Jul. 1, 2011, 4 pages.

Upson, James; King, Frederick; Roberts, Lamar; A constant amplitude transistorized unit for remote brain stimulation, Electroencephalography and Clinical Neurophysiology, Jun. 11, 1962.

Brindley, G.S., An implant to empty the bladder or close the urethra, Journal of Neurology, Neurosurgery, and Psychiatry, 1977.

Kaplan, Hilton; Loeb, Gerald, Design and Fabrication of an Injection Tool for Neuromuscular Microstimulators, Annals of Biomedical Engineering, vol. 37, No. 9., Jun. 24, 2009.

Troyk, Philip; Schwan, Martin; Closed-Loop Class E Transcutaneous Power and Data Link for MicroImplants. IEEE Transactions on Biomedical Engineering, vol. 39, No. 6, Jun. 1992.

Mithun, Joe; Rajkumar, Vikram, Shanmugapriya: Apnea Detecting Sensors; Sathyabama Deemed University, 2006.

Babak, Ziaie; Nardin, Mark; Coghlan, Anthony; Najafi, Khalil, A Single-Channel Implantable Microstimulator for Functional Neuromuscular Stimulation, IEEE Transactions on Biomedical Engineering, vol. 44, No. 10, Oct. 1997.

Robin, S; Sawan, M.; Harvey, J.F.; Abdel-Gawad, M.; Abdel-Baky, T.M.; Eihili, M.M., A New Implantable Microstimulator Dedicated to Selective Stimulation of the Bladder, 19th International Conference, IEEE/EMBS Oct. 30-Nov. 2, 1997.

Troyk, P.R.; Donaldson N. de N.; Implantable FES Stimulation Systems: What is Needed, 2001 Neuromodulation Society, Neuromodulation vol. 4, No. 4, 2001.

Loeb, Gerald; Richmond, Frances; Moore, W. Henry; Peck, Raymond, 1st Annual International IEEE-EMBS Spedal Topic Conference on Microtechnologies in Medicine & Biology, Oct. 2000.

Harrison, Reid, Designing Efficient inductive Power Links for Implantable Devices, University of Utah, 2007.

Mohtashami, Saba, Electrochemical Properties of Flexible Electrodes for Implanted Neuromuscular Excitation Applications, McMaster University, Oct. 1, 2011.

Baker, Michael; Sarpeshkar, Rahul, Feedback Analysis and DEsign of RF Power Links for Low-Power Bionic Systems, IEEE Transactions on Biomedical Circuits and Systems, vol. 1, No. 1, Mar. 2007.

Zierhofer, Clemens, HOchmair, Erwin, High-Efficiency Coupling-Insensitive Transcutaneous Power and Data Transmission Via an Inductive Link, IEEE Transactions on Biomedical Engineering, vol. 37, No. 3, Jul. 1990.

Tran, W.H., Loeb, G.E. Richmond, F.J.R.; Ahmed, R.; Clark, G.T.; Haberman, P.B., First Subject Evaluated with Simulated BION Treatment in Posterior Genioglossus to Prevent Obstructive Sleep Apnea, Proceedings of the 26th Annual International Conference of the IEEE EMBS, San Francisco, CA, USA, Sep. 2004.

Jow, Uei-Ming; Ghovanloo, Maysam, Design and Optimization of Printed Spiral Coils for Efficient Transcutaneous Inductive Power Transmission, IEEE Transactions on Biomedical Circuits and Systems, vol. 1, No. 3, Sep. 2007.

Steiglitz, Thomas, Polymer-based Substrates and Flexible Hybrid Assembly Techniques for Implantable Active Microdevices, Business Briefing: Medical Device Manufacturing & Technology, 2002.

Jarvis, Jonathan; Salmons, Stanley, The Application and Technology of Implantable Neuromuscular StimulatorsL an introduction and overview, Medical Engineering and Physics 23, 2001.

Manola, Ljubomir; Holsheimer, Jan; Veltink, Peter; Bradley, Kerry; Peterson, David, Theoretical Investigation Into Longitudinal Cathodal Field Steering in Spinal Cord Stimulation, Neurmodulation: Technology at the Neural Interface, vol. 10, No. 2, 2007.

Joho, Dominik, Plagemann, Christian, Burgard, Wolfram, Modeling RFID Signal Strength and Tag Detection for Localization and Mapping, Proceedings of the IEEE International Conference on Robotics and Automation, Kobe Japan, May 2009.

Werber, D.; Schwenter, A.; Biebl, E.M., Investigation of RF Transmission Properties of Human Tissues, Advances in Radio Science, vol. 4, 2006.

Cameron, Tracy; Loeb, Gerald; Peck, Raymond; Schulman, Joseph; Strojnik, Primoz; Troyk, Philip, Micromodular Implants to Provide Electrical Stimulation of Paralyzed Muscles and Limbs, IEEE Transactions on Biomedical Engineering, vol. 44, No. 9, Sep. 1997.

Mokwa, Wilfried; Schnakenberg, Uwe, Micro-Transponder Systems for Medical, IEEE Transactions on Instrumentation and Measurement, vol. 50, No. 6, Dec. 2001.

Grill, Warren; Veraart, Claude; Mortimer, Thomas, Selective Activation of Peripheral Nerve Fascicles: Use of Field Steering Currents, Annual International Conference of the IEEE Engineering in Medicine and Biology Society, vol. 13, No. 2, 1991.

(56) References Cited

OTHER PUBLICATIONS

Loeb, G.E.; Zemin, C,J.; Schulman, J.H.; Troyk, P.R., Injectable Microstimulator for Functional Electrical Stimulation, Med. and Biol. Eng, & Comput, 1991.

Young, Darrin, Wireless Powering and Data Telemetry for Biomedical Implants, 31st Annual International Conference of the IEEE EMBS, Minnesota, USA, Sep. 2009.

Han, J.H.; Lim, H.G.; Kim, J.M.; Lee, C.W.; Park, I.Y.; Cho, J.H., Inductively-Coupled Control Unit for Fully Implantable Middle Ear Hearing Devices, Proceedings of the 2005 IEEE Engineering in Medicine and Biology 27th Annual Conference, China, Sep. 2005.

Oliven, A; Kaufman, E.; Kaynan, R.; Golboda, T.; Oliven, R.; Geitini, L.; Odeh, M.; Tov, N.; Schwartz, A.R.; Kimel, E., Effects of Cross-Sectional Area, Compliance and External Pressure on Pharyngeal Collapsibility in Patients with Obstructive Sleep Apnea, A68 Upper Airway and Repiratory Physiology, 2010.

Yoo, Paul B.; Durand, Dominique, Effects of Selective Hypoglossal Nerve Stimulation on Canine Upper Airway Mechanics, Journal of Applied Physiology, 2005.

Huang, Jingtao; Sahin, Mesut; Druand, Dominique, Dilation of the oropharynx via selective stimulation of the hypoglossal nerve, Journal of Neural Engineering, 2005.

Oliven, A; Tov, N.; Geltini, L.; Steinfeld, U.; Oliven, R.; Schwartz, A.R.; Odeh, M., Effect of Genioglossus Contraction on Pharyngeal Lumen and Airflow in Sleep Apnoea Patients, European Respiratory Journal, 2007.

David, Ross; Cosendal, Gregoire; Arcos, Isabel; Kushner, Douglas; Mishler, Delta; Decker, Christopher; Ripley, Anne-Marie; Maceri, Dennis; Sanderson, Donna; Zilberman, Yitzhak; Schulman, Joseph, Development of the BION Microstimulator for Treatment in Obstructive Sleep Apnea, Alfred Mann Foundation, 2003.

Eastwood, P.R.; Barnes, M.; McEvoy, R.D; Wheatley, J; Walsh, J.H.; O'Donoghue, F.J.; Catcheside, P.; Tyler, L.; Maddison, K.J.; Rochford, P.D.; Antic, N.; Worsnop C.; Churchward, T.; Eckert, D.J.; Campbell, M.C., Hee, G.; Palme, C.E., Robinson, S.H.; Kezirian, E.; Goding, G.; Jordan, A.S.; Smith, P.L.; Schwartz, A.R.; Malhotra, A.; Hillman, D.R., Feasibility of Hypoglossal Nerve Stimulation Therapy to Treat Obstructive Sleep Apnea, Am. J. Respir Crit Care Med, 2010.

Randerath, Winfried, Electrical Stimulation of the Upper Airways Muscles, Institute for Pheumology at the University Witten/Herdecke, 2006.

Schwartz, Alan; Eisele, David; Hari, Anil; Testerman, Roy; Erickson, Donald; Smith, Philip, Electrical Stimulation of the Lingual Musculature in Obstructive Sleep Apnea, Johns Hopkins Asthma and Allergy Center, Feb. 1996.

Kezirian, Eric J.; Boudewyns, An; Eisele, David; Schwartz, Alan; Philip, Smith; Van de Heyning, Paul; De Backer, Wilfried, Electrical Stimulation of the Hypoglossal Nerve in the Treatment of Obstructive Sleep Apnea, Sleep Medicine Reviews, 2009.

Isono, S.; Tanaka, A.; Nishino, T., Effects of Tongue Electrical Stimulation on Pharyngeal Mechanics in Anaesthetized Patients with Obstructive Sleep Apnoea, Eur Respir J, 1999.

Fregosi, Ralph, Influence of Tongue Muscle Contraction and Dynamic Airway Pressure on Velopharyngeal Volume in the Rat, J. Appl. Physiol, Dec. 2007.

Van De Heyning, Paul; Badr, M. Safwan; Baskin, Jonatha Z.; Bornermann, Michael Cramer; De Backer, Wilfried A.; Dotan, Yaniv; Hohenhorst, Winfried; Knaack, Lennart; Lin, Ho-Sheng, Maurer, Joachim T.; Netzer, Aviram; Odland, Rick M.; Oliven, Arie; Strohl, Kingman P.; Vanderveken, Oliver M.; Verbraecken, Johan; Woodson, B. Tucker, Implanted Upper Airway Stimulation Device for Obstructive Sleep Apnea, The Laryngoscope, Jul. 2012.

Oliven, Ron; Tov, Naveh; Odeh, Majed; Gaitini, Luis; Steinfeld, Uri; Schwartz, Alan; Oliven, Arie, Interacting Effects of Genioglossus Stimulation and Mandibular Advancements in Sleep Apnea, J. Appl. Physiol, 2009.

Peng, Chih-Wei; Chen, Jia-Jin Jason; Lin, Chou-Ching K.; Poon, Paul Wai-Fung; Liang, Chih-Kuo; Lin, Kang-Ping, High Frequency Block of Selected Axons Using an Implantable Microstimulator, 2004.

Burnett, Theresa; Mann, Eric; Cornell, Sonia; Ludlow, Christy, Laryngeal Elevation Achieved by Neuromuscular Stimulation at Rest, J. Appl. Physiol. 94, 2003.

Hu, Linggang; Xu, Xiaomei; Gong, Yongeheng; Fan, Xiaofang; Wang, Liangxing; Zhang, Jianhua, Percutaneous Biphasic Electrical Stimulation for Treatment of Obstructive Sleep Apnea Syndrom, IEEE Transactions on Biomedical Engineering, vol. 55, No. 1, Jan. 2008.

Dotan, Y.; Goliboda, T.; Netzer, A.; Geitini, L.; Oliven, A., Parameters Affecting the Mechanical Effect of Electrical Stimulation (ES) of the Tongue Muscles in Patients with Obstructive Sleep Apnea (OSA), Am. J. Respir. Crit Care Med, 2010.

Yoo, Paul Byong-Suk, Selective Stimulation and Recording of the Canine Hypoglossal Nerve for the Treatment of Obstructive Sleep Apnea, Case Western Reserve University, May 2004.

Oliven, Arie, Treating Obstructive Sleep Apnea with Hypoglossal Nerve Stimulation, Curr. Opin. Pulm. Med. 2011.

Goding, George; Eisele, David; Testerman, Roy; Smith, Philip; Roertgen, Karen; Schwartz, Alan, Relief of Upper Airway Obstruction with Hypoglossal Nerve Stimulation in the Canine, Laryngoscope, 1998.

Oliven, Arie; Schnall, Robert; Pillar, Giora; Gavriely, Noam; Oden, Majed, Sublingual Electrical Stimulation of the Tongue During Wakefulness and Sleep, Respiration Physiology, 127, 2001.

Mwenge, Gimbada; Rombaux, Phillippe; Dury, Myriam; Lengele, Benoit; Rodenstein, Daniel, Targeted Hypoglossal Neurostimulation for Obstructive Sleep Apnea. A 1 year pilot study, ERJ Express, May 17, 2012.

Mann, Eric; Burnett, Theresa; Cornell, Sonia; Ludlow, Christy, The Effect of Neuromuscular Stimulation of the Genioglossus on the Hypopharyngeal Airway, The Laryngoscope, 2002.

Oliven, Arie; O'Hearn, Daniel; Boudewyns, An; Odeh, Majed; De Backer, Wilfried; van de Heyning, Paul; Smith, Philip; Eisele, David; Allan, Larry; Schneider, Hartmut; Testerman, Roy; Schwartz, Alan, Upper Airway Response to Electrical Stimulation of the Genioglossus in Obstructive Sleep Apnea, J. Appl. Physiol. vol. 95, 2003.

Guillemeniualt, Christian; Powell, Nelson; Bowman, Bruce; Stoohs, Riccardo, The Effect of Electrical Stimulation on Obstructive Sleep Apnea Syndrome, Chest, Jan. 1995.

Eastwood, Peter; Barnes, Maree; Walsh, Jennifer; Maddison, Kathieen; Hee, Geoffrey; Schwartz, Alan; Smith, Philip; Malhotra, Atul; McEvoy, Douglas; Wheatley, John; O'Donoghue, Fergal; Rochford, Peter; Churchward, Tom; Campbell, Matthew; Palme, Carsten; Robinson, Sam; Goding, George; Eckert, Danny; Jordan, Amy; Catcheside, Peter; Tyler, Louise; Antic, Nick; Worsnop, Christopher; Kezirian, Eric; Hillman, David, Treating Obstructive Sleep Apnea with Hypoglossal Nerve Stimulation, Sleep vol. 34, No. 11, 2011.

Schwartz, Alan; Bennet, Marc; Smith, Philip; De Backer, Wilfried; Hedner, Jan; Boudewyns, An; Van de Heyning, Paul; Ejnell, Hasse; Hochban, Walter; Knaack, Lennart; Podszus, Thomas; Penzel, Thomas; Peter, J. Hermann; Goding, George; Erickson, Donald; Testerman, Roy: Ottenhoff, Frans; Eisele, David, Therapeutic Electrical Stimulation of the Hypoglossal Nerve in Obstructive Sleep Apnea, Arch Otolaryngol Head Neck Surg, vol. 127, Oct. 2001.

Randerath, Winfried, Galetke, Wolfgang; Domanski, Uinke; Weitkunat, Rolf; Ruhle Karl-Heinz, Tongue-Muscle Training by Intraoral Electrical Neurostimulation in Patients with Obstructive Sleep Apnea, Sleep, vol. 27, No. 2, 2004.

Eastwood, P.R.; Walsh, J.H.; Maddison, K.J.; Baker, V.A.; Tesfayesus, W.; Hillman, D.R., Treatment of Obstructive Sleep Apnea With Unilateral Hypoglossal Nerve Stimulation, Am J Respir Crit Care Med 181, 2010.

Loeb, Gerald; Richmond, Frances; Baker, Lucinda, The BION devices: injectable interfaces with peripheral nerves and muscles, Neurosurgery Focus 20, 2006.

U.S. Appl. No. 14/041,519, filed Sep. 30, 2013.

* cited by examiner

DEVICES FOR TREATMENT OF SLEEP APNEA

RELATED APPLICATIONS

This application is a continuation of application Ser. No. 14/041,598, filed on Sep. 30, 2013, which is a continuation-in-part application of application Ser. No. 13/629,690, filed on Sep. 28, 2012 (pending), application Ser. No. 13/629,694, filed on Sep. 28, 2012, now U.S. Pat. No. 8,577,472, issued Nov. 5, 2013, application Ser. No. 13/629,701 filed on Sep. 28, 2012, now U.S. Pat. No. 8,588,941, issued Nov. 19, 2013, application Ser. No. 13/629,712, filed on Sep. 28, 2012 (pending), application Ser. No. 13/629,725, filed on Sep. 28, 2012, now U.S. Pat. No. 8,577,478, issued Nov. 5, 2013, application Ser. No. 13/629,730, filed on Sep. 28, 2012, now U.S. Pat. No. 8,577,465, issued Nov. 5, 2013 application Ser. No. 13/629, 741, filed on Sep. 28, 2012, now U.S. Pat. No. 8,577,466, issued Nov. 5, 2013, application Ser. No. 13/629,748, filed on Sep. 28, 2012, now U.S. Pat. No. 8,700,183, issued Apr. 15, 2014, application Ser. No. 13/629,757, filed on Sep. 28, 2012 (pending), application Ser. No. 13/629,762, filed on Sep. 28, 2012, now U.S. Pat. No. 8,577,467, issued Nov. 5, 2013, application Ser. No. 13/629,793, filed on Sep. 28, 2012, now U.S. Pat. No. 8,577,468, issued Nov. 5, 2013, application Ser. No. 13/629,819, filed on Sep. 28, 2012, now U.S. Pat. No. 8,718,776, issued May 6, 2014, application Ser. No. 13/630, 392, filed on Sep. 28, 2012, now U.S. Pat. No. 8,644,957, issued Feb. 4, 2014, application Ser. No. 13/629,721, filed on Sep. 28, 2012, now U.S. Pat. No. 8,574,164, issued Nov. 5, 2013, and application Ser. No. 13/629,686, filed on Sep. 28, 2012, now U.S. Pat. No. 8,577,464, issued Nov. 5, 2013, each of which claims the benefit of priority under 35 U.S.C. §119 (e) to U.S. Provisional Application No. 61/541,651, filed Sep. 30, 2011, and also to U.S. Provisional Application No. 61/657,424, filed Jun. 8, 2012. Additionally, application Ser. Nos. 13/629,686 and 13/629,721 are also continuations-in-part of both application Ser. No. 12/642,866, filed Dec. 21, 2009, now U.S. Pat. No. 8,585,617, issued Nov. 19, 2013, and of application Ser. No. 12/581,907, filed Oct. 20, 2009 (pending). All of the above-referenced applications are incorporated herein by reference in their entirety.

TECHNICAL FIELD

Embodiments of the present disclosure generally relate to devices and methods establishing communications between an implantable device and an external unit. In some cases, the implantable unit may be configured for modulating a nerve. More particularly, embodiments of the present disclosure relate to devices and methods for modulating a nerve through the delivery of energy via an implantable electrical modulator.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

At least some of the presently disclosed embodiments may include methods of communicating between an implantable device, such as a neural modulator, and an external unit configured to communicate with the implantable device. In applications related to nerve modulation, such methods of communication may increase the efficiency of signal transmission between the implantable device and the external unit. Such methods of communication may also assist in other applications; for example, where an implantable device may include a sensor to sense one or more physiological conditions. For example, an implantable glucose sensor may monitor glucose levels of a subject, and, utilizing communication methods disclosed herein, relay information about glucose levels to an external device.

The foregoing are just a few examples of conditions to which neuromodulation may be of benefit, however embodiments of the invention described hereafter are not necessarily limited to treating only the above-described conditions.

SUMMARY

A device according to some embodiments may include a housing configured for temporary affixation on at least one of a neck and a head of a subject. The device may also include at least one processor associated with the housing and configured for electrical communication with a power source, and an antenna associated with the at least one processor. The at least one processor may be configured to communicate with an implant circuit in at least one of the neck and the head of the subject in a location proximate a hypoglossal nerve, cause the implant circuit to receive power in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

A device according to some embodiments may include a housing configured for location external to a body of a subject. The device may also include at least one processor associated with the housing and configured for electrical communication with a power source, and an antenna associated with the at least one processor. The at least one processor may be configured to communicate with an implant circuit located within the body of the subject, cause the implant circuit to receive power in a first power mode and in a second power mode, wherein a first level of power delivered in the first power mode is less than a second level of power delivered in the second power ode, and wherein during a therapy period, power delivery in the first mode occurs over a total time that is greater than about 50% of the therapy period.

A device according to some embodiments may include a primary antenna and a housing configured for location external to a body of a subject. The device may also include at least one processor associated with the housing and the primary antenna and configured for electrical communication with a power source. The at least one processor may be further configured to communicate with an implant circuit implanted in a blood vessel of the subject proximate to at least one of a renal nerve, a baroreceptor, and a glossopharyngeal nerve of the subject, cause the implant circuit to receive power in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

A device according to some embodiments may include a patch configured for placement on a side of a hairline opposite a substantially haired region of a head of a subject. The device may also include at least one processor associated with the patch and configured for electrical communication with a power source, and a primary antenna associated with the at least one processor. The at least one processor may be configured to communicate, via the primary antenna, with a secondary antenna located beneath the skin of a subject on a side of a hairline opposite a substantially haired region of the subject, cause an implant circuit to receive power through the secondary antenna in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

Some embodiments may include a method of delivering power to an implanted circuit. The method may include communicating with the implanted circuit, which is implanted in a body of a subject. The method may also include transmitting power to the implanted circuit in a first power mode and in a second power mode, wherein a first level of power delivered in the first power mode is less than a second level of power delivered in the second power mode, and wherein during a therapy period, power delivery in the first power mode occurs over a total time that is greater than about 50% of the therapy period.

A device according to some embodiments may include a housing configured for location external to a body of a subject. The device may also include at least one processor associated with the housing and configured to communicate with a circuit implanted in the subject within proximity to a tongue of the subject, wherein the circuit is in electrical communication with at least one electrode, receive a physiological signal from the subject via the circuit, and send a control signal to the implanted circuit in response to the physiological signal, wherein the control signal is predetermined to activate neuromuscular tissue within the tongue.

Some embodiments may include a method of activating neuromuscular tissue within an implanted circuit. The method may include communicating with the implanted circuit, which is implanted within a proximity of a tongue of a subject, wherein the implanted circuit is in electrical communication with at least one electrode, receiving a physiological signal from the subject via the implanted circuit, sending a control signal to the implanted circuit in response to the physiological signal, and activating neuromuscular tissue within the tongue of the subject via the control signal.

A device according to some embodiments may include a housing configured for location external to a body of a subject. The device may also include at least one processor associated with the housing and configured to communicate with a circuit implanted in a blood vessel of the subject within proximity to at least one of a renal nerve, a baroreceptor, and a glossopharyngeal nerve, wherein the circuit is in electrical communication with at least one electrode, receive a physiological signal from the subject, and send a control signal to the implanted circuit in response to the physiological signal, wherein the control signal is predetermined to modulate nerve tissue to affect blood pressure.

A device according to some embodiments may include a housing configured for location external to a body of a subject. The device may also include at least one processor associated with the housing and configured to communicate with a circuit implanted in the subject within proximity to at least one nerve to be modulated, wherein the circuit is in electrical communication with at least one electrode, receive a physiological signal from the subject, and send a control signal to the implanted circuit in response to the physiological signal, wherein the control signal is predetermined to modulate the at least one nerve to be modulated.

A device according to some disclosed embodiments may include an external unit configured for location on a neck of a subject to communicate with an implant unit implanted proximal to a tongue of a subject. An indicator, associated with the external unit, may be configured to produce an indicator signal when the external unit is within a predetermined range of the implant unit. In addition, the indicator may be configured to vary the indicator signal according to a distance between the external unit and the implant unit.

A device according to some disclosed embodiments may include an external unit configured to communicate with an implant unit beneath the skin of a subject, an indicator associated with the external unit, and at least one processor configured to generate a primary signal on a primary antenna associated with the external unit. The primary signal being configured to cause a secondary signal on a secondary antenna associated with the implant unit. In addition, the processor may be configured to determine a degree of coupling between a primary antenna associated with the external unit and a secondary antenna associated with the implant unit and cause the indicator to produce a signal when the degree of coupling exceeds a predetermined threshold.

A device according to some disclosed embodiments may include an external unit configured to communicate with an implant unit beneath the skin of a subject and an indicator associated with the external unit. The indicator being configured to produce an indicator signal when the external unit is within a predetermined range of the implant unit and being configured to vary the indicator signal according to a distance between the external unit and the implant unit.

A device according to some disclosed embodiments may include a housing, configured for location on a subject to communicate with an implant unit implanted proximate to at least one of a renal nerve, a baroreceptor, and a glossopharyngeal nerve, and an indicator associated with the housing. The indicator may be configured to produce an indicator signal when the housing is within a predetermined range of the implant unit. In addition, the indicator may be configured to vary the indicator signal according to a distance between the housing and the implant unit.

A device according to some disclosed embodiments may include a patch configured for placement on a side of hairline opposite a substantially haired region of a subject and an indicator associated with the patch. The indicator may be configured to produce an indicator signal when the patch is within a predetermined range of the implant unit. In addition, the indicator may be configured to vary the indicator signal according to a distance between the patch and the implant unit.

The device may further include one or more of the following features: the indicator signal may include a visual output, a tactile output, an audible output, or an electrical signal configured to communicate with the implant unit; the electrical signal may cause the implant unit to modulate a nerve and to induce at least one of a proprioceptive or kinesthesic reaction in the subject; the external unit may comprise at least one processor; the at least one processor being configured to: generate a primary signal on a primary antenna associated with the external unit, the primary signal being configured to cause a secondary signal on a secondary antenna associated with the implant unit; determine a degree of coupling between the primary antenna associated with the external unit and the secondary antenna associated with the implant unit; and cause the indicator to produce the indicator signal when the degree of coupling exceeds a predetermined threshold; determination of the degree of coupling between the primary antenna associated with the external unit and the secondary antenna associated with the implant unit may be based, at least in part, on a measure of capacitive coupling, on a measure of radio frequency coupling, on a measure of inductive coupling, or on an observation of non-linear behavior in a circuit associated with the implant unit; the observation of non-linear behavior may include at least one of observation of a transition from linear behavior to non-linear behavior or observation of non-linear harmonic behavior.

In addition, the processor may further be configured to cause the indicator to produce the indicator signal when the degree of coupling does not exceed a predetermined threshold; the at least one processor may be configured to operate in a placement mode and a therapy mode, cause the indicator to produce the variable signal during operation in the placement mode, and transition from the placement mode to the therapy mode when a correct placement condition is satisfied; the correct placement condition may include at least one of a predetermined coupling threshold and a predetermined timing threshold, such that the predetermined timing threshold includes a pre-sleep waiting period. The device may further comprise a skin patch with an adhesive and configured for adherence to the skin of the subject, such that the external unit is removably connected to the skin patch, and such that the at least one processor is configured to operate in a placement mode when the external unit is connected to the skin patch.

A method of locating an external unit with respect to an implant unit according to some disclosed embodiments may include the steps of detecting a distance between the external unit and the implanted unit located beneath the skin of a subject, producing an indicator signal when the external unit is within a predetermined range of the implant unit, and varying the indicator signal as a function of a distance between the external unit and the implant unit.

A device according to some disclosed embodiments may include an external unit comprising at least one processor. The processor may be configured to receive a signal indicative of tongue movement in a subject from an implant unit implanted in the subject, determine whether the tongue movement is representative of sleep disordered breathing, generate a modulation control signal to correct the sleep disordered breathing when the at least one processor determines an occurrence of sleep disordered breathing.

The device may further include one or more of the following features: the at least one processor may be configured to determine whether the sleep disordered breathing includes an apnea precursor, determine whether the sleep disordered breathing includes hypopnea, and/or determine whether the sleep disordered breathing includes an hypopnea precursor; the implant unit may be implanted in a location in contact with the subject's tongue muscle; and there may be a primary antenna in electrical communication with the at least one processor, the primary antenna being configured to transmit the modulation control signal to a secondary antenna associated with the implant unit, such that the modulation control signal includes a stimulation control signal configured to interact with the implant unit to cause a contraction of the muscle.

In addition, the signal indicative of tongue movement may be indicative of relative motion between a primary antenna associated with the at least one processor and a secondary antenna associated with the implant unit; the at least one processor may be further configured to generate a sub-modulation control signal for transmission to the implant unit via the primary antenna and/or detect relative motion between the primary antenna and the secondary antenna based on a degree of coupling between the primary antenna and the secondary antenna; the degree of coupling may include at least one of a measure of capacitive coupling, radiofrequency coupling, or inductive coupling; the degree of coupling may further include a measure of non-linear behavior in a circuit associated with the implant unit; and the at least one processor may be configured to adjust at least one characteristic of the modulation control signal based on a severity of the sleep disordered breathing, the at least one characteristic of the modulation control signal including voltage amplitude, current amplitude, pulse frequency, or pulse duration.

Another device according to some disclosed embodiments may include an external unit comprising at least one processor. The at least one processor may be configured to receive a signal indicative of movement of a subject's tongue, generate a modulation control signal based on the received signal indicative of movement of the subject's tongue, and transmit the modulation control signal via a primary antenna to a secondary antenna associated with an implant unit.

The device may further include one or more of the following features: the modulation control signal may include a stimulation control signal configured to interact with the implant unit to cause a contraction in a muscle, the signal may be indicative of movement of a subject's tongue is indicative of relative motion between the primary antenna and the secondary antenna associated with the implant unit; the at least one processor may further be configured to generate a sub-modulation control signal for transmission to the implant unit via the primary antenna, and detect relative motion between the primary antenna and the secondary antenna based on a determination of a degree of coupling between the primary antenna and the secondary antenna; the determination of the degree of coupling may include at least one of a measure of capacitive coupling, radiofrequency coupling, inductive coupling, or an observation of non-linear behavior in a circuit associated with the implant unit; and the at least one processor may further be configured to adjust at least one characteristic of the modulation control signal based on the movement of the subject's tongue, the at least one characteristic of the modulation control signal including voltage amplitude, current amplitude, pulse frequency, or pulse duration.

A method for detecting tongue movement in a subject according to some disclosed embodiments may include receiving from an implant unit implanted in the subject a signal indicative of tongue movement in the subject, generating a modulation control signal based on the signal indicative of tongue movement, and transmitting the modulation control signal from a primary antenna associated with an external unit to a secondary antenna associated with an implant unit.

The method may further include one or more of the following features: determining whether the tongue movement is representative of sleep disordered breathing, determining whether the sleep disordered breathing includes an apnea precursor, and determining whether the sleep disordered breathing includes hypopnea. In addition, the at least one processor may further be configured to determine whether the sleep disordered breathing includes an hypopnea precursor; the modulation control signal may include a stimulation control signal configured to interact with the implant unit to cause a contraction in a muscle; and the signal indicative of tongue movement may be indicative of relative motion between the primary antenna associated with the external unit and the secondary antenna associated with the implant unit.

Moreover, the method may include generating a sub-modulation control signal for transmission to the implant unit via the primary antenna, and detecting relative motion between the primary antenna and the secondary antenna based on determination of a degree of coupling between the primary antenna and the secondary antenna; the determination of the degree of coupling may include at least one of a measure of capacitive coupling, radiofrequency coupling, inductive coupling, or an observation of non-linear behavior in a circuit associated with the implant unit; and adjusting at least one characteristic of the modulation control signal based on the signal indicative of tongue movement, the at least one characteristic of the modulation control signal including voltage amplitude, current amplitude, pulse frequency, or pulse duration.

A device may include at least one pair of modulation electrodes configured for implantation in the vicinity of a nerve to be modulated such that the electrodes are spaced apart from one another along a longitudinal direction of the nerve to be modulated. The electrodes may be further configured to facilitate an electric field in response to an applied electric signal, the electric field including field lines extending in the longitudinal direction of the nerve to be modulated. The device may further include at least one circuit in electrical communication with the at least one pair of modulation electrodes and being configured to cause application of the electric signal applied at the at least one pair of modulation electrodes. A method of modulating a nerve may include receiving an alternating current (AC) signal at a device configured to be implanted into a body of a subject and generating a voltage signal in response to the AC signal. The method may further include applying the voltage signal to at least one pair of modulation electrodes configured for implantation in the vicinity of the nerve such that the electrodes are spaced apart from one another along a longitudinal direction of the nerve; generating an electrical field in response to the voltage signal applied to the at least one pair of modulation electrodes, the electric field including field ones extending in a longitudinal direction of the nerve; and modulating the nerve.

A device according to some embodiments may include a primary antenna configured to be located external to a subject. The device may also include at least one processor in electrical communication with the primary antenna and configured to receive a condition signal from an implantable device, the condition signal indicative of a precursor to sleep disordered breathing, and cause transmission of a primary signal from the primary antenna to the implantable device, in response to the condition signal, to stimulate at least one nerve in response to the precursor to sleep disordered breathing.

Some embodiments may include a method of detecting a sleep breathing disorder. The method may include receiving, via a primary antenna located external to a body of a subject, a condition signal from an implantable device, the condition signal indicating the presence of a precursor to sleep disordered breathing, and transmitting a primary signal from the primary antenna to the implantable device, in response to the condition signal, to stimulate at least one nerve in response to the occurrence of the precursor to sleep disordered breathing.

A device according to some embodiments may include a primary antenna configured to be located external to a subject and at least one processor in electrical communication with the primary antenna. The at least one processor may be configured to cause transmission of a primary signal from the primary antenna to an implantable device implanted in the subject on a genioglossus muscle proximal to a hypoglossal nerve of the subject, wherein the implantable device includes at least one pair of modulation electrodes. The at least one processor may be further configured to adjust one or more characteristics of the primary signal to generate a sub-modulation control signal adapted to cause a current at the at least one pair of modulation electrodes below a neuromuscular modulation threshold of the hypoglossal nerve when received by the implanted device and to generate a modulation control signal adapted to cause a current at the at least one pair of modulation electrodes above a neuromuscular modulation threshold of the hypoglossal nerve when received by the implantable device.

A device according to some embodiments may include a primary antenna configured to be located external to a subject and at least one processor in electrical communication with the primary antenna. The at least one processor may be configured to cause transmission of a primary signal from the primary antenna to an implantable device implanted in a blood vessel of a subject in proximity to at least one of a renal nerve, a baroreceptor, and a glossopharyngeal nerve, wherein the implantable device includes at least one pair of modulation electrodes. The at least one processor may be further configured to adjust one or more characteristics of the primary signal to generate a sub-modulation control signal adapted to cause a current at the at least one pair of modulation electrodes below a neuromuscular modulation threshold of the at least one of a renal nerve, a baroreceptor, and a glossopharyngeal nerve when received by the implantable device and to generate a modulation control signal adapted to cause a current at the at least one pair of modulation electrodes above a neuromuscular modulation threshold at least one of a renal nerve, a baroreceptor, and a glossopharyngeal nerve when received by the implantable device.

A device according to some embodiments may include a primary antenna configured to be located on the skin of a subject on a substantially hairless region of a head of the subject and at least one processor in electrical communication with the primary antenna. The at least one processor may be configured to cause transmission of a primary signal from the primary antenna to an implantable device implanted beneath the skin of the subject, wherein the implantable device includes at least one pair of modulation electrodes located in a vicinity of an occipital nerve beneath the skin of the subject in a substantially hairless region of the head. The at least one processor may be further configured to adjust one or more characteristics of the primary signal to generate a sub-modulation control signal adapted to cause a current at the at least one pair of modulation electrodes below a neuromuscular modulation threshold of the occipital nerve when received by the implantable device and to generate a modulation control signal adapted to cause a current at the at least one pair of modulation electrodes above a neuromuscular modulation threshold of the occipital nerve when received by the implantable device.

A device according to some embodiments may include a primary antenna configured to be located external to a subject and at least one processor in electrical communication with the primary antenna. The at least one processor may be configured to cause transmission of a primary signal from the primary antenna to an implantable device, wherein the implantable device includes at least one pair of modulation electrodes. The at least one processor may be further configured to adjust one or more characteristics of the primary signal to generate a sub-modulation control signal adapted to cause a current at the at least one pair of modulation electrodes below a neuromuscular modulation threshold when received by the implantable device and to generate a modulation control signal adapted to cause a current at the at least one pair of modulation electrodes above a neuromuscular modulation threshold when received by the implantable device.

Some embodiments may include a method of transmitting signals to an implantable device. The method may include determining one or more sub-modulation characteristics of a sub-modulation control signal so as not to cause a neuromuscular modulation inducing current across at least one pair of modulation electrodes in electrical communication with an implantable device when the sub-modulation control signal is received by the implantable device. The method may further include generating the modulation control signal having the one or more modulation characteristics and generating the sub-modulation control signal having the one or more sub-modulation characteristics. The method may further include transmitting, via the primary antenna, the modulation control signal to a secondary antenna associated with the implantable device and transmitting, via the primary antenna, the sub-modulation control signal to a secondary antenna associated with the implantable device.

An implant unit according to some embodiments may include a flexible carrier, at least one pair of modulation electrodes on the flexible carrier, and at least one implantable circuit in electrical communication with the at least one pair of modulation electrodes. The at least one pair of modulation electrodes and the at least one circuit may be configured for implantation through derma on an underside of a subject's chin and for location proximate to terminal fibers of the medial branch of the subject's hypoglossal nerve. In addition, the implantable circuit and the electrodes may be configured to cooperate in order to generate an electric field adapted to modulate one or more of the terminal fibers of the medial branch of the hypoglossal nerve.

According to another embodiment of the present disclosure, an implant unit may include a flexible carrier, at least one pair of modulation electrodes on the flexible carrier, and at least one implantable circuit in electrical communication with the at least one pair of modulation electrodes. The at least one pair of modulation electrodes and the at least one circuit may be configured for implantation through derma on an underside of a subject's chin. The at least one pair of modulation electrodes may be configured for implantation at a location between the subject's geniohyoid muscle and the subject's genioglossus muscle and may be configured to cooperate with the implantable circuit in order to generate an electric field adapted to cause modulation of the subject's hypoglossal nerve from that location.

According to still another embodiment of the present disclosure, an implant unit may include a flexible carrier, at least one pair of modulation electrodes on the flexible carrier, and at least one implantable circuit in electrical communication with the at least one pair of modulation electrodes. The at least one pair of modulation electrodes and the at least one circuit may be configured for intravascular implantation in a subject in a location proximal to at least one of a renal nerve, a baroreceptor, and a glossopharyngeal nerve, and wherein the implantable circuit and the electrodes may be configured to cooperate in order to generate an electric field adapted to cause modulation of at least a portion of the at least one of a renal artery, a carotid baroreceptor, and a glossopharyngeal nerve.

According to still another embodiment of the present disclosure, an implant unit may include an elongated flexible carrier sized and configured for implantation beneath the skin to extend from a first location of a substantially hairless region on one side of a hairline, across a hairline to a second location of a substantially hafted region in a vicinity of an occipital nerve. In addition, the implant unit may include an antenna located on the carrier for implantation in the first location and at least one pair of modulation electrodes configured on the carrier for implantation in the second location. At least one circuit may be in electrical communication with the at least one pair of modulation electrodes and wherein the implantable circuit and the at least one pair of modulation electrodes are configured to cooperate in order to generate an electric field adapted to cause modulation of at least a portion of the occipital nerve through application of an electric field.

An implant unit configured for implantation into a body of a subject according to some embodiments may include an antenna configured to receive a signal. The implant unit may also include at least one pair of modulation electrodes configured to be implanted proximal to the tongue of the subject in the vicinity of a hypoglossal nerve, the at least one pair of modulation electrodes may be configured to receive an applied electric signal in response to the signal received by the antenna and generate an electrical field to modulate the hypoglossal nerve from a position where the at least one pair of modulation electrodes are spaced apart from the hypoglossal nerve.

An implant unit configured for implantation into a body of a subject according to some embodiments may include an antenna configured to receive a signal. The implant unit may also include at least one pair of modulation electrodes configured to be implanted into the body of the subject in the vicinity of at least one nerve to be modulated, the at least one pair of modulation electrodes may be configured to receive an applied electric signal in response to the signal received by the antenna and generate an electrical field to modulate the at least one nerve from a position where the at least one pair of modulation electrodes are spaced apart from the at least one nerve.

A hypertension therapy device for affecting blood pressure according to some embodiments may include an antenna configured to receive a signal. The device may also include at least one pair of modulation electrodes configured to be implanted in the blood vessel of the subject in the vicinity at least one of a renal nerve, a carotid baroreceptor, and a glossopharyngeal nerve, the at least one pair of modulation electrodes may be configured to receive an applied electric signal in response to the signal received by the antenna and generate an electrical field to modulate the at least one of a renal nerve, a carotid baroreceptor, and a glossopharyngeal nerve from a position where the at least one pair of modulation electrodes are spaced apart from the at least one nerve.

A head pain management device configured for implantation beneath skin of a head of a subject according to some embodiments may include an antenna configured to receive a signal and to be implanted beneath the skin of a subject in a substantially hairless region. The device may also include at least one pair of modulation electrodes configured to be implanted beneath the skin of a subject in a substantially haired region and a flexible carrier configured to electrically connect the antenna and the at least one pair of modulation electrodes. In addition, the least at one pair of modulation electrodes may be configured to receive an applied electric signal in response to the signal received by the antenna and generate an electrical field to modulate an occipital nerve of the subject from a position where the at least one pair of modulation electrodes are spaced apart from the occipital nerve.

A method of modulating at least one nerve may include receiving an alternating current (AC) signal at an implant unit and generating a voltage signal in response to the AC signal. The method may also include applying the voltage signal to at least one pair of modulation electrodes, the at least one pair of modulation electrodes being configured to be implanted into the body of a subject in the vicinity of the at least one nerve; and generating an electrical field in response to the voltage signal applied to the at least one pair of modulation electrodes to modulate the at least one nerve from a position where the at least one pair of modulation electrodes do not contact the at least one nerve.

A device according to some embodiments may include an implantable circuit and at least one pair of implantable electrodes electrically connected with the implantable circuit. The circuit and the electrodes may be configured for implantation in a subject proximal to a genioglossus muscle in the vicinity of a hypoglossal nerve. The circuit may be configured to deliver to the electrodes an electrical signal having a current less than about 1.6 milliamps, and the electrodes may be configured to emit an electric field such that a portion of the field lines extend along a length of the hypoglossal nerve such that the delivery of the electrical signal of less than about 0.6 milliamps causes modulation of the hypoglossal nerve.

A device according to some embodiments may include an implantable circuit and at least one pair of implantable electrodes electrically connected with the implantable circuit. The circuit and the electrodes may be configured for implantation in a subject in the vicinity of a nerve. The circuit may be configured to deliver to the electrodes an electrical signal having a current less than about 1.6 milliamps, and the electrodes may be configured to emit an electric field such that a portion of the field lines extend along a length of the nerve such that the delivery of the electrical signal of less than about 1.6 milliamps causes modulation of the nerve.

A device according to some embodiments may include an implantable circuit and at least one pair of implantable electrodes configured to be implanted beneath the skin of a subject in a substantially haired region in the vicinity of an occipital nerve of a subject. The device may include an antenna configured to receive a signal and to be implanted beneath the skin of the subject in a substantially hairless region. The implantable electrodes may be electrically connected with a first end of the implantable circuit and the antenna may be electrically connected with a second end of the implantable circuit. In addition, the circuit may be configured to deliver to the electrodes an electrical signal having a current less than about 1.6 milliamps, and the electrodes may be configured to emit an electric field such that a portion of the field lines extend along a length of the nerve such that the delivery of the electrical signal of less than about 1.6 milliamps causes modulation of the nerve.

A device according to some embodiments may include an implantable circuit and at least one pair of implantable electrodes electrically connected with the implantable circuit. The circuit and the electrodes may be configured for implantation in a subject in a blood vessel in the vicinity of at least one of a renal nerve, a carotid baroreceptor, and a glossopharyngeal nerve. The circuit may be configured to deliver to the electrodes an electrical signal having a current less than about 1.6 milliamps, and the electrodes may be configured to emit an electric field such that a portion of the field lines extend along a length of the nerve such that the delivery of the electrical signal of less than about 1.6 milliamps causes modulation of the at least one of a renal nerve, a carotid baroreceptor, and a glossopharyngeal nerve.

Some embodiments may include a method of stimulating a nerve via at least one pair of electrodes associated with an implanted circuit and implanted in the vicinity of the nerve. The method may include delivering to the electrodes, via the implanted circuit, an electrical signal having a current less than about 1.6 milliamps. The method may further include stimulating the nerve via the generation of an electrical field between the electrodes by the electrical signal having a current less than about 1.6 milliamps.

A device for regulating energy delivery to an implanted circuit is disclosed. The device according to some embodiments may include at least one implantable circuit and at least one pair of implantable electrodes in electrical communication with the circuit. The at least one implantable circuit and at least one pair of implantable electrodes may be configured for implantation in a vicinity of a genioglossus muscle of a subject. The at least one pair of implantable electrodes may be configured to modulate a hypoglossal nerve. The at least one implantable circuit may be configured deliver a power signal to the at least one pair of implantable electrodes. The power signal may have at least one of a power level and a duration determined based on a severity of a detected physiologic condition.

The device according to some embodiments may include at least one implantable circuit and at least one pair of implantable electrodes in electrical communication with the circuit. The at least one pair of implantable electrodes may be configured to modulate at least one nerve. The at least one implantable circuit may be configured deliver a power signal to the at least one pair of implantable electrodes. The power signal may have at least one of a power level and a duration determined based on a severity of a detected physiologic condition.

The device according to some embodiments may include a flexible carrier configured for implantation in a blood vessel of a subject, at least one implantable circuit, and at least one pair of implantable electrodes in electrical communication with the circuit and located on the carrier. The at least one pair of implantable electrodes being configured to modulate at least one of a renal nerve, a baroreceptor, and a glossopharyngeal nerve. The at least one implantable circuit may be configured deliver a power signal to the at least one pair of implantable electrodes. The power signal may have at least one of a power level and a duration determined based on a severity of a detected physiologic condition.

Some embodiments may include a method of regulating energy delivery to an implanted circuit for treating a sleep disordered breathing condition. The method may include detecting a severity of a physiological condition in a body of a subject and determining, based on the severity of the physiological condition, at least one of a power level or a duration of a power signal to be delivered by the implanted circuit to at least one pair of electrodes implanted proximal to a hypoglossal nerve of the subject and in electrical communication with the implanted circuit. The method may further include delivering the power signal to the at least one pair of electrodes and the hypoglossal nerve of the subject via the power signal. The method may include determining a degree of coupling between a primary antenna associated with an external unit and a secondary antenna associated with an implant unit implanted in a body of a subject, and regulating delivery of power to the implant unit based on the determined degree of coupling.

A device according to some embodiments may include an implantable flexible carrier configured for implantation proximal to a genioglossus muscle of a subject and a pair of electrodes located on the carrier. The electrodes may be spaced from each other by a distance greater than 3 mm, and may be configured to facilitate, when supplied with an electrical signal, a substantially unidirectional electric field sufficient to modulate a hypoglossal nerve.

A device according to some embodiments may include an implantable flexible carrier and a pair of electrodes located on the carrier. The electrodes may be spaced from each other by a distance greater than 3 mm, and may be configured to facilitate, when supplied with an electrical signal, a substantially unidirectional electric field sufficient to modulate at least one nerve.

A device according to some embodiments may include an implantable flexible carrier configured for implantation in a blood vessel of a subject in a vicinity of at least one of a renal nerve, a carotid baroreceptor, and a glossopharyngeal nerve, and a pair of electrodes located on the carrier. The electrodes may be spaced from each other by a distance greater than 3 mm and may be configured to facilitate, when supplied with an electrical signal, a substantially unidirectional electric field sufficient to modulate the at least one of a renal nerve, a carotid baroreceptor, and a glossopharyngeal nerve.

A device according to some embodiments may include an implantable flexible carrier configured for location beneath the skin of a head of a subject, and a pair of electrodes located on the carrier. The electrodes may be configured for implantation beneath the skin of a substantially haired region of the head of the subject in a vicinity of an occipital nerve. In addition, the electrodes may be spaced from each other by a distance greater than 3 mm, and may be configured to facilitate, when supplied with an electrical signal, a substantially unidirectional electric field sufficient to modulate the occipital nerve.

A device according to some disclosed embodiments may include a skin patch configured for temporary affixation on at least one of a neck and a head of a subject. The device may additionally include a primary antenna associated with the skin patch and at least one processor associated with the skin patch and configured for electrical communication with a power source. The processor may be further configured to communicate with an implant unit via the primary antenna when the implant unit is implanted in at least one of the neck and the head of the subject in a location proximate a hypoglossal nerve, and to determine a degree of coupling between the primary antenna and a secondary antenna associated with the implant unit and to regulate delivery of power from the power source to the implant unit based on the degree of coupling between the primary antenna and the secondary antenna.

A device according to some disclosed embodiments may include an external unit configured for location external to a body of a subject and at least one processor associated with the external unit and configured for electrical communication with a power source. The device may additionally include a primary antenna associated with the at least one processor. The processor may be configured to communicate with an implant unit when the implant unit is implanted beneath skin of the subject, to determine a degree of coupling between the primary antenna and a secondary antenna associated with the implant unit, and to regulate delivery of power from the power source to the implant unit based on the degree of coupling between the primary antenna and the secondary antenna.

A device according to some disclosed embodiments may include a primary antenna and a housing configured for location on a body of a subject proximate to at least one of a renal nerve, a baroreceptor, and a glossopharyngeal nerve. The primary antenna may be associated with the housing. The device may additionally include at least one processor associated with the housing and configured for electrical communication with a power source. The at least one processor may be further configured to communicate with an implant unit inserted into a blood vessel of the subject, to determine a degree of coupling between the primary antenna and a secondary antenna associated with the implant unit, and to regulate delivery of power from the power source to the implant unit based on the degree of coupling between the primary antenna and the secondary antenna.

A device according to some disclosed embodiments may include a patch configured for placement on a side of a hairline opposite a substantially haired region of a subject and a primary antenna associated with the patch. The device may additionally include at least one processor associated with the patch and configured for electrical communication with a power source. The processor may be further configured to communicate with a modulator including electrodes implanted in a scalp of the subject, to determine a degree of coupling between the primary antenna and a secondary antenna associated with the modulator, and to regulate delivery of power from the power source to the modulator based on the degree of coupling between the primary antenna and the secondary antenna.

The device may further include one or more of the following features, either alone or in combination: the external unit may include a skin patch configured for adherence to the subject's skin; the primary antenna may include a coil antenna; the external unit may include a flexible substrate; and the at least one processor may be configured to receive physiologic data via the implant unit and regulate delivery of power from the power source to the implant unit based on both the physiologic data and the degree of coupling between the primary antenna and the secondary antenna, such that the physiologic data may be representative of a motion of the implant unit.

In addition, an upper limit of power delivered from the power source to the implant unit may be determined according to an upper threshold associated with the implant unit; a lower limit of power delivered from the power source to the implant unit may be determined according to an efficacy threshold of the delivered power; the primary antenna may be configured to transmit power to the secondary antenna through radiofrequency transmission of an alternating current signal; and the at least one processor may be configured to regulate the delivered power by adjusting at least one of voltage, pulse rate, and current associated with the alternating current signal.

The degree of coupling between the primary antenna and the secondary antenna may include a measure of capacitive coupling, radiofrequency coupling, inductive coupling, or non-linear behavior in the implant unit; and the measure of non-linear behavior may include at least one of a measure of a transition to non-linear harmonic behavior and a measure of non-linear harmonic behavior.

A method for regulating delivery of power to an implant unit is also disclosed. The method may include communicating with the implant unit, which may be implanted in a body of a subject, determining a degree of coupling between a primary antenna associated with a power source and a secondary antenna associated with the implant unit, and regulating delivery of power from the power source to the implant unit based on the degree of coupling.

The method may further include one or more of the following features, either alone or in combination: receiving physiologic data via the implant unit; regulating delivery of power from the power source to the implant unit based on the physiologic data and the degree of coupling; and the physiologic data may be representative of a motion of the implant unit. Moreover, the method may include determining an upper limit of the power delivered from the power source to the implant unit according to an upper threshold associated with the implant unit; and determining a lower limit of the power delivered from the power source to the implant unit according to an efficacy threshold of the power delivered.

In addition, the power may be delivered from the power source to the implant unit via radiofrequency transmission of an alternating current signal; regulating delivery of power from the power source to the implant unit may comprise adjusting at least one of voltage, pulse rate, and current associated with the alternating current signal; the degree of coupling between the primary antenna and the secondary antenna may include a measure of capacitive coupling, radiofrequency coupling, inductive coupling, or non-linear behavior in the implant unit, and the measure of non-linear behavior may include at least one of a measure of a transition to non-linear harmonic behavior and a measure of non-linear harmonic behavior.

A device according to some embodiments may include a housing configured for temporary affixation on at least one of a neck and a head of a subject. The device may also include at least one processor associated with the housing and configured for electrical communication with a power source, and an antenna associated with the at least one processor. The at least one processor may be configured to communicate with an implant circuit in at least one of the neck and the head of the subject in a location proximate a hypoglossal nerve, cause the implant circuit to receive power in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

A device according to some embodiments may include a housing configured for location external to a body of a subject. The device may also include at least one processor associated with the housing and configured for electrical communication with a power source, and an antenna associated with the at least one processor. The at least one processor may be configured to communicate with an implant circuit located within the body of the subject, cause the implant circuit to receive power in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

A device according to some embodiments may include a primary antenna and a housing configured for location external to a body of a subject. The device may also include at least one processor associated with the housing and the primary antenna and configured for electrical communication with a power source. The at least one processor may be further configured to communicate with an implant circuit implanted in a blood vessel of the subject proximate to at least one of a renal nerve, a baroreceptor, and a glossopharyngeal nerve of the subject, cause the implant circuit to receive power in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

A device according to some embodiments may include a patch configured for placement on a side of a hairline opposite a substantially haired region of a head of a subject. The device may also include at least one processor associated with the patch and configured for electrical communication with a power source, and a primary antenna associated with the at least one processor. The at least one processor may be configured to communicate, via the primary antenna, with a secondary antenna located beneath the skin of a subject on a side of a hairline opposite a substantially haired region of the subject, cause an implant circuit to receive power through the secondary antenna in a first power mode and in a second power mode, wherein a first level of power delivered in the first power mode is less than a second level of power delivered in the second power mode, and wherein during a therapy period, power delivery in the first mode occurs over a total time that is greater than about 50% of the therapy period.

Some embodiments may include a method of delivering power to an implanted circuit. The method may include communicating with the implanted circuit, which is implanted in a body of a subject. The method may also include transmitting power to the implanted circuit in a first power mode and in a second power mode, wherein a first level of power delivered in the first power mode is less than a second level of power delivered in the second power mode, and wherein during a therapy period, power delivery in the first power mode occurs over a total time that is greater than about 50% of the therapy period.

A device according to some embodiments of the present disclosure includes a housing configured to retain a battery, a primary antenna associated with the housing, and at least one processor in electrical communication with the battery and the primary antenna. In some embodiments, the at least one processor may be configured to cause transmission of a primary signal from the primary antenna to an implant unit implanted in at least one of a neck and a head of a subject during a treatment session of at least three hours in duration, wherein the primary signal is generated using power supplied by the battery and includes a pulse train, the pulse train including a plurality of stimulation pulses.

A device according to some embodiments of the present disclosure includes a housing configured to retain a battery, a primary antenna associated with the housing, and at least one processor in electrical communication with the battery and the primary antenna. In some embodiments, the at least one processor may be configured to cause transmission of a primary signal from the primary antenna to an implantable device during a treatment session of at least three hours in duration, wherein the primary signal is generated using power supplied by the battery and includes a pulse train, the pulse train including a plurality of stimulation pulses.

A device according to some embodiments of the present disclosure includes a housing configured to retain a battery, a primary antenna associated with the housing, and at least one processor in electrical communication with the battery and the primary antenna. In some embodiments, the at least one processor may be configured to cause transmission of a primary signal from the primary antenna to an implantable device located in a blood vessel of a subject in a vicinity of at least one of a renal nerve, carotid baroreceptor, and glossopharyngeal nerve of a subject during a treatment session of at least three hours in duration, wherein the primary signal is generated using power supplied by the battery and includes a pulse train, the pulse train including a plurality of stimulation pulses.

A device according to some embodiments of the present disclosure includes a patch configured for placement on a one side of a hairline opposite a substantially haired region of a subject, a primary antenna associated with the patch, and at least one processor associated with the patch and configured for electrical communication with a battery. In some embodiments, the at least one processor may be configured to cause transmission of a primary signal from the primary antenna to a secondary antenna of an implantable device during a treatment session of at least three hours in duration, wherein the primary signal is generated using power supplied by the battery and includes a pulse train, the pulse train including a plurality of modulation pulses.

Additional embodiments consistent with the present disclosure may include a method for delivering electrical modulation treatment pulses. The method may include generating a primary signal in a primary antenna using power supplied by a battery, wherein the primary antenna is associated with a housing configured to retain the battery. The method may further include transmitting the primary signal from the primary antenna to an implantable device during a treatment session of at least three hours in duration, wherein the primary signal includes a pulse train and the pulse train includes a plurality of modulation pulses.

A device may include at least one pair of modulation electrodes configured for implantation in the vicinity of a nerve to be modulated such that the electrodes are spaced apart from one another along a longitudinal direction of the nerve to be modulated. The electrodes may be further configured to facilitate an electric field in response to an applied electric signal, the electric field including field lines extending in the longitudinal direction of the nerve to be modulated. The device may further include at least one circuit in electrical communication with the at least one pair of modulation electrodes and being configured to cause application of the electric signal applied at the at least one pair of modulation electrodes. A method of modulating a nerve may include receiving an alternating current (AC) signal at a device configured to be implanted into a body of a subject and generating a voltage signal in response to the AC signal. The method may further include applying the voltage signal to at least one pair of modulation electrodes configured for implantation in the vicinity of the nerve such that the electrodes are spaced apart from one another along a longitudinal direction of the nerve; generating an electrical field in response to the voltage signal applied to the at least one pair of modulation electrodes, the electric field including field lines extending in a longitudinal direction of the nerve; and modulating the nerve.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

DESCRIPTION OF EXEMPLARY EMBODIMENTS

Figure 1:
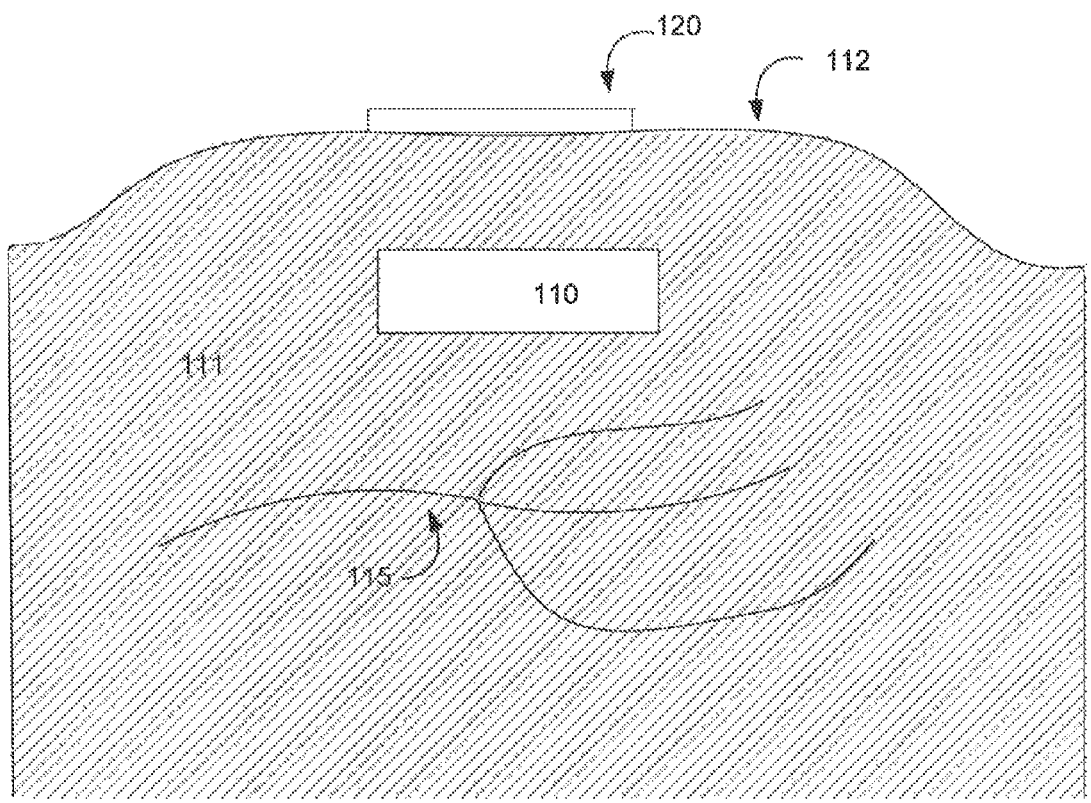
FIG. 1 schematically illustrates an implant unit and external unit, according to an exemplary embodiment of the present disclosure.

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for neuromuscular modulation through the delivery of energy. Neuromuscular modulation may refer to the modulation of nerves, muscles or a combination of both. Muscular modulation may include the stimulation, modification, regulation, or therapeutic alteration of muscular activity, electrical activity. Muscular modulation may be applied directly to a muscle. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied. Furthermore, implant unit 110 may be configured to not perform any modulation at all. Implant unit 110 may be configured to measure physiological data, for example through sensors or other measuring devices. For example, implant unit 110 may include sensors to detect a level of glucose in a subject, such information may be communicated to external unit 120 through various means as described herein. Some of the exemplary embodiments described herein refer to neural modulation. It will be understood that many of the exemplary techniques, devices, and methods disclosed may also be applied directly to muscles to cause muscular modulation.

In patients with OSA, for example, a primary target response of nerve stimulation may include contraction of a tongue muscle (e.g., the genioglossus muscle) in order to move the tongue to a position that does not block the patient's airway, e.g. away from the pharyngeal wall. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with OSA, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

FIG. 1 illustrates an implant unit and external unit, according to an exemplary embodiment of the present disclosure. An implant unit 110 may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. A more detailed discussion of non contacting neuromodulation is provided below with respect to FIGS. 10a, 10b, 10c, and 11. The implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Further details regarding implantation locations of an implant unit 110 for treatment of OSA are provided below with respect to FIGS. 12 and 13. Implant unit 110 may also be configured for placement in other locations. For example, migraine treatment may require subcutaneous implantation in the back of the neck, near the hairline of a subject, or behind the ear of a subject, to modulate the greater occipital nerve, lesser occipital nerve, and/or the trigeminal nerve. Further details regarding implantation locations of an implant unit 110 for treatment of head pain, such as migraine headaches, are provided below with respect to FIG. 14. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve. Further details regarding implantation locations of an implant unit 110 for treatment of hypertension are provided below, with respect to FIGS. 15 and 16.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
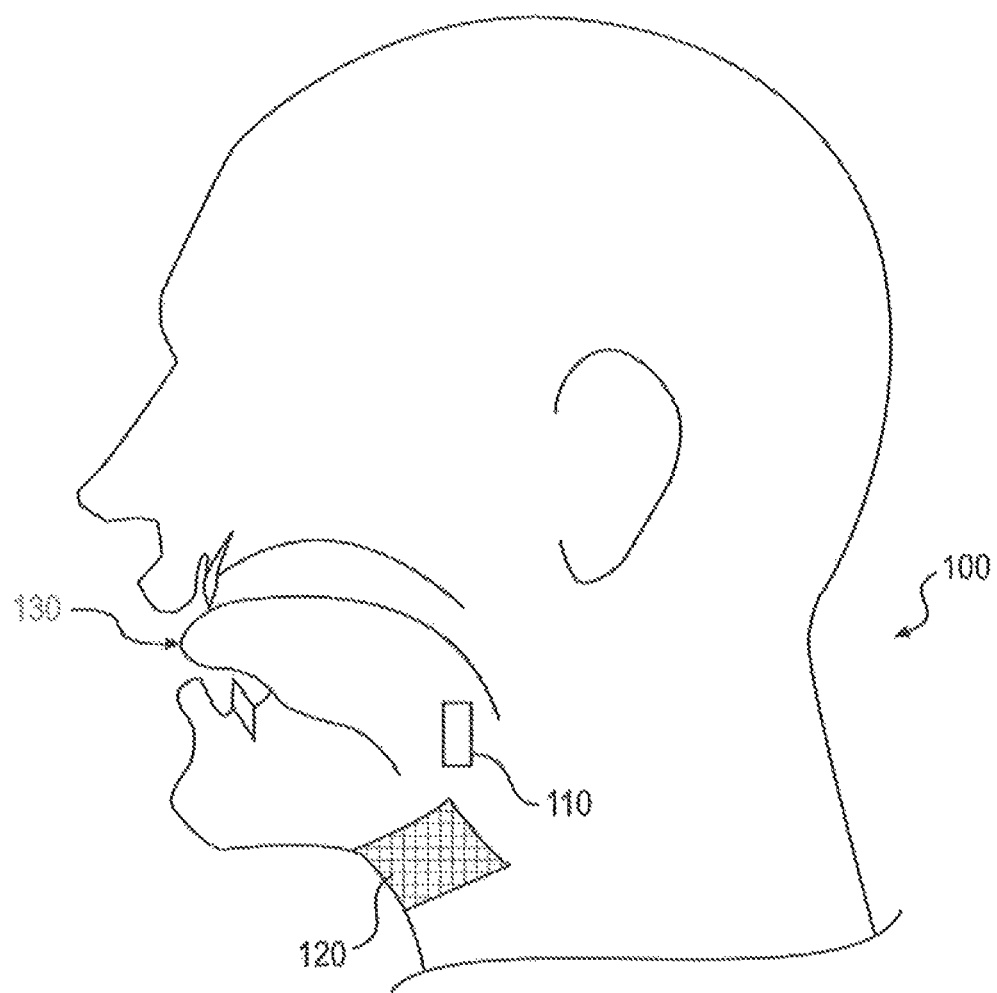
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, the external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient, such as the back of a patient's neck, e.g. for communication with a migraine treatment implant unit, on the outer portion of a patient's abdomen, e.g. for communication with a stomach modulating implant unit, on a patient's back, e.g. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions. The housing may also be removably affixed to skin of a subject through alternate means, such as straps or bands. Any of the various elements described herein as associated with the external unit may be located on or off the housing, as appropriate. For example, a housing comprising a patch may include a processor and a primary antenna.

Figure 3:
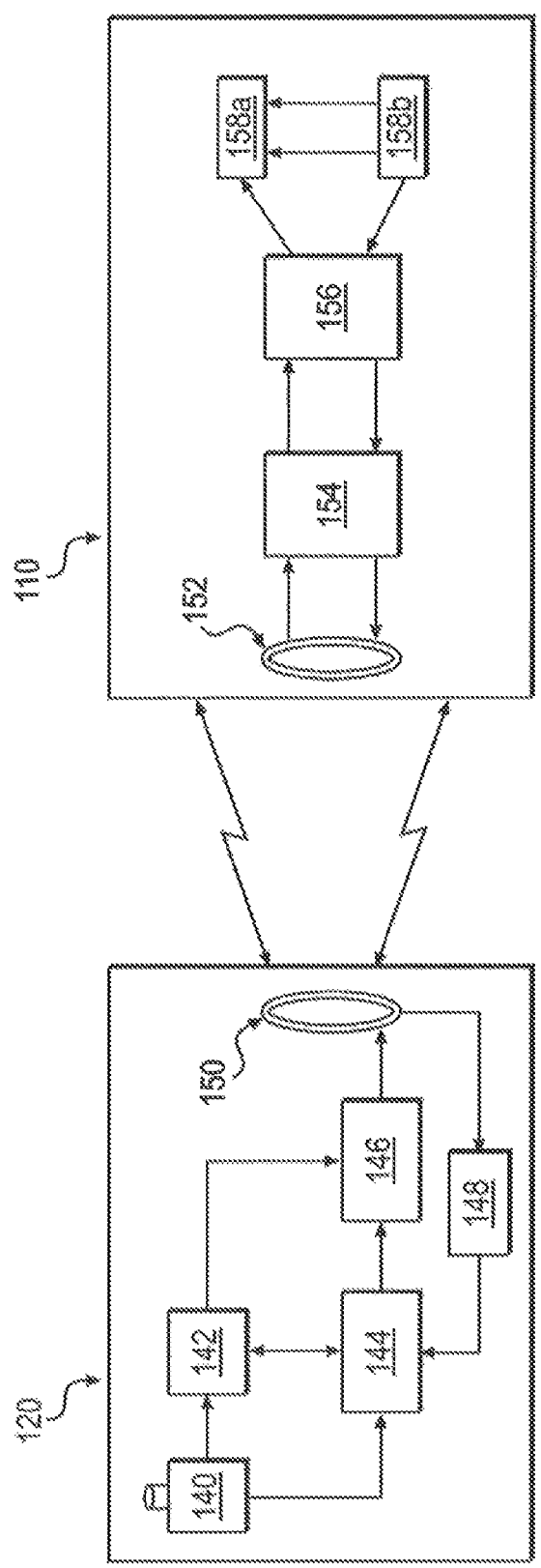
FIG. 3 schematically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery. In some embodiments, external unit 120 may include a housing configured to retain a power source, such as a battery. As further detailed below, embodiments of the neuromodulation techniques disclosed herein permit neuromodulation at low power consumption levels. Thus, in some embodiments, a battery serving as a power source may have a capacity of less than 60 milliamp-hours, less than 120 milliamp-hours, and less than 240 milliamp-hours.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g. a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RE amplifiers, power amplifiers, or any other type of device that can increase the gain associated one or more aspects of a signal. The amplifier may further be configured to output the amplified signals to one or more components within external unit 120.

FIG. 3 further illustrates that external unit 120 may be associated with an indicator 145. That is, indicator 145 may be removably or permanently attached to external unit 120. In one embodiment, for example, indicator 145 may be located within external unit 120. Alternatively, indicator 145 may be in wired or wireless communication with external unit 120 from a location external to external unit 120.

The indicator 145 may include any suitable device configured to provide a signal to the user and/or may include any suitable signal output elements configured to communicate with a user. Suitable signal output elements may include, but are not limited to, audible, visual, and tactile outputs. In one embodiment, for example, the signal output means may include an electrical signal configured to communicate with the implant unit 110. That is, the electrical signal may cause the implant unit 110 to stimulate a nerve and/or induce one of a proprioceptive or kinesthesic reaction in the user. Thus, in the context of an implant unit 110 located in the geniogloss-sus, processor 144 may be configured to function as the indicator 145 to cause a modulation of a nerve located within the tongue by the implant unit 110 (e.g. the processor may provide the signal that causes a physiological indication to the user). In other embodiments, the indicator 145 may be configured to emit an audible signal, including one or more tones.

The indicator 145 may also or alternatively be configured with lighting elements (e.g., LEDs, etc.) for providing various visual signals to a user. Additionally or alternatively, the indicator 145 may include a device configured to vibrate as part of an alert issued to the user. It should be understood that any combination of these or other suitable signaling elements may be included in the indicator 145 associated with external unit 120.

The indicator 145 may further include any suitable antenna known to those skilled in the art and may be configured to send and receive signals to a user in order to alert the user of a condition relating to the external unit 120 and/or implant unit 110. In one embodiment, for example, the indicator 145 may be configured to provide a variable signal according to a distance between the external unit 120 and the implant unit 110.

The indicator 145 may be configured to permit a user to place the external unit 120 at an optimal location in relation to the implant unit 110. For example, a user interested in placing external unit 120 on the skin, for example, in the vicinity of implant 110 may proceed to move external unit 120 around in the general vicinity of implant unit 110. When external unit 120 is placed in a location where a suitable connection can be achieved between external unit 120 and implant unit 110 (e.g., a suitable coupling connection), the indicator 145 may alert the user of this condition. The indicator 145 may further be configured to alert the user of the degree of connectivity between external unit 120 and implant unit 110 such that the user may be able to place the external unit in a location where the connection between the two units is at or near a maximum level.

One or more functions associated with the indicator 145 may be provided by a processor associated with external unit 120. For example, among other functions, a processor may be configured to monitor a connection strength between external unit 120 and implant unit 110 and issue a control signal to cause the indicator 145 to activate.

The external unit may additionally include a primary antenna 150. The primary antenna may be configured as part of a circuit within external unit 120 and may be coupled either directly or indirectly to various components in external unit 120. The primary antenna may be configured for location external to a subject. For example, as shown in FIG. 3, primary antenna 150 may be configured for communication with the amplifier 146.

The primary antenna may include any conductive structure that may be configured to create an electromagnetic field. The primary antenna may further be of any suitable size, shape, and/or configuration. The primary antenna may be flexible to an extent permitting it to generally conform to the contours of a subject's skin. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.1 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e., the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible, material and/or insulative material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of cons, layout of cons, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.01 mm and 1 mm. These antenna parameters are exemplary only, and may be adjusted above or below the ranges given to achieve suitable results.

Figure 4:
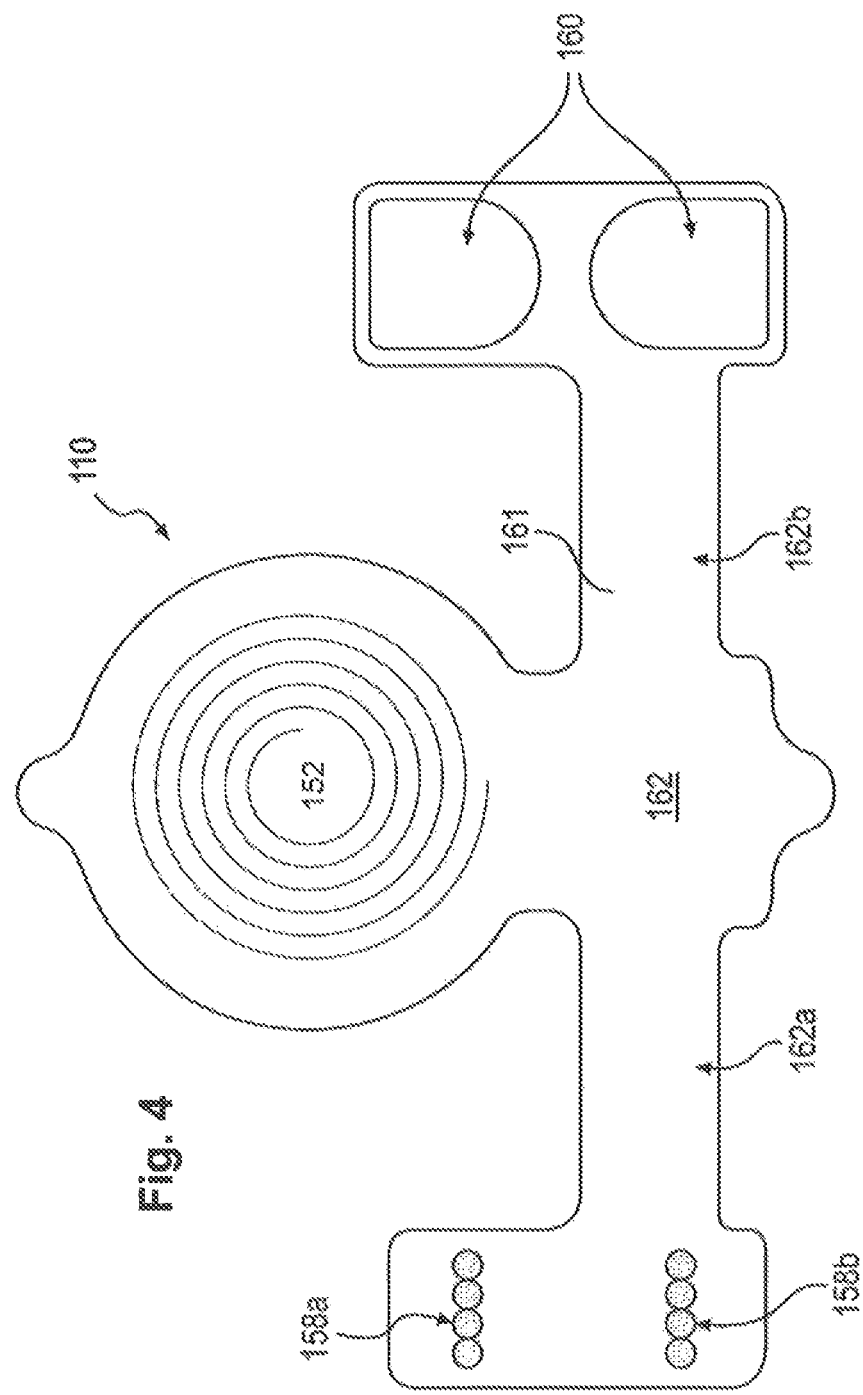
FIG. 4 is a top view of an implant unit, according to an exemplary embodiment of the present disclosure.

Implant unit 110 may additionally include a plurality of field-generating implant electrodes 158a, 158b. The electrodes may include any suitable shape and/or orientation on the implant unit so long as the electrodes may be configured to generate an electric field in the body of a patient. Like implant unit 110, implant electrodes 158a and 158b may be configured for implantation into the body of a subject in the vicinity of one or more nerves either together with or separate from implant unit 110. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, point electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 5. Electrodes on different sides of implant unit 110 may be activated sequentially or simultaneously to generate respective electric fields. Implant electrode pairs may be spaced apart from one another along the longitudinal direction by a distance of less than about 25 mm. Implant electrodes may have a thickness between about 200 nanometers and 1 millimeter, and may have a surface area of about 0.01 mm$^2$ to about 80 mm$^2$. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. In other embodiments, anode and cathode electrode pairs may be spaced apart by a distance of approximately 3 mm. In still other embodiments, anode and cathode electrode pairs may be spaced from each other by a distance greater than about 3 mm.

Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

As noted, electrodes 158a and 158b may configured to be implanted into the body of a subject in the vicinity of at least one nerve to be modulated. Implant (or modulation) electrodes 158a and 158b may be configured to receive an applied electric signal in response to the signal received by the antenna and generate an electrical field to modulate the at least one nerve from a position where the at least one pair of modulation electrodes does not contact the at least one nerve.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body (e.g., for attaching flexible carrier 161 to a surface of non-nerve tissue within the body of a subject). For example, in some embodiments, implant unit 110 may include an elongate arm 162 having a first extension 162*a* and, optionally, a second extension 162*b*. Extensions 162*a* and 162*b* may aid in orienting implant unit 110 with respect to a particular muscle (e.g., the genioglossus muscle), a nerve within a patient's body, or a surface within a body above a nerve. For example, first and second extensions 162*a*, 162*b* may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162*b* of elongate arm 162 and/or on first extension 162*a* of elongate arm 162. Implant unit 110 may be constructed in various shapes. In some embodiments, implant unit may appear substantially as illustrated in FIG. 4. In other embodiments, implant unit 110 may lack illustrated structures such as second extension 162*b*, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body. For example, flexible carrier 161 may facilitate orientation of implant unit 110 with respect to the contour of a particular tissue. Such tissue may include any combination of muscle tissue, bone, connective tissue, adipose tissue, or organ tissue. For subjects suffering from obstructive sleep apnea, for instance, implant unit 110 may be configured to adapt to the contour of the genioglossus muscle.

As illustrated in FIG. 4, secondary antenna 152, circuitry 180, and electrodes 158*a*, 158*b* may be mounted on or integrated with flexible carrier 161. Various circuit components and connecting wires (discussed further below) may be used to connect secondary antenna with implant electrodes 158*a* and 158*b*. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include silicone, polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating. In some embodiments, the protective coating may include a plurality of layers, including different materials or combinations of materials in different layers.

Figure 5:
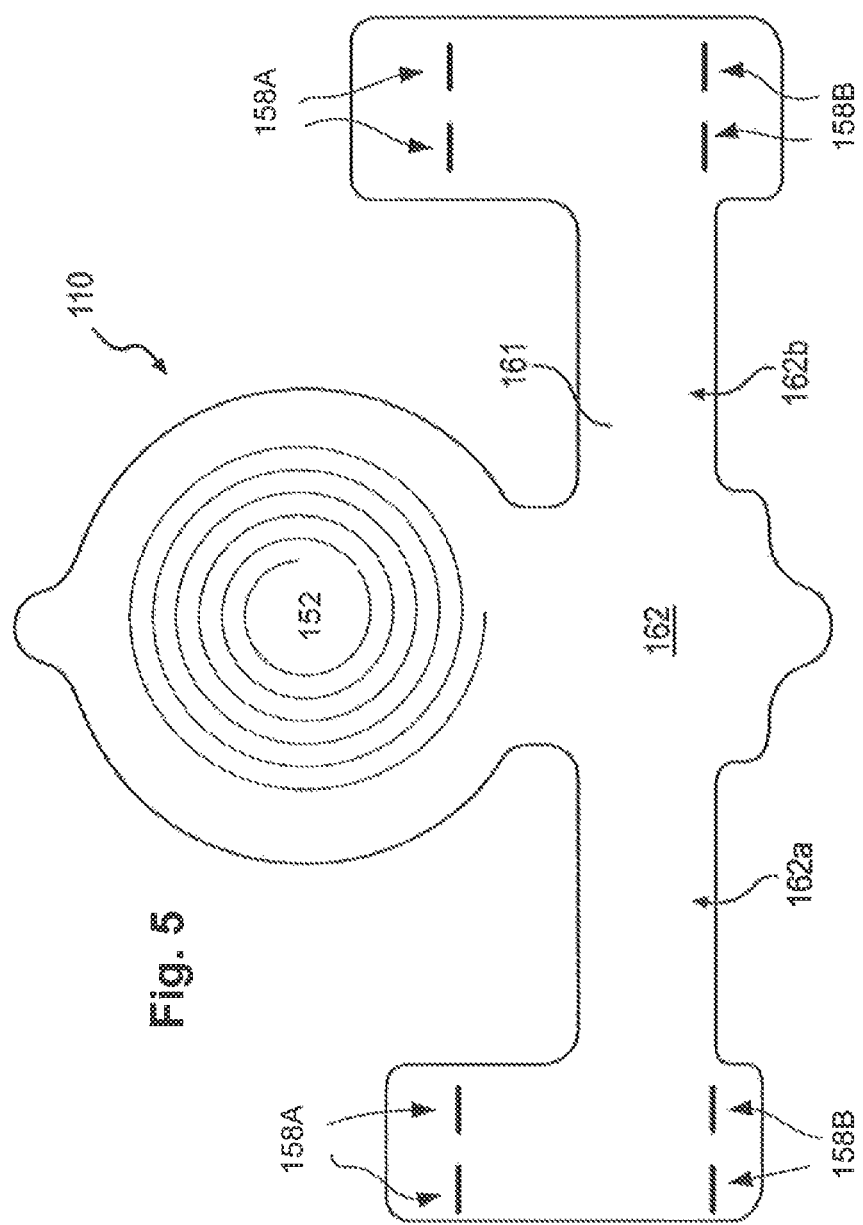
FIG. 5 is a top view of an alternate embodiment of an implant unit, according to an exemplary embodiment of the present disclosure.

FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162*a* and second extension 162*b*. FIG. 5 illustrates an embodiment wherein implant electrodes 158*a* and 158*b* include short line electrodes.

Returning to FIGS. 2 and 3, external unit 120 may be configured to communicate with implant unit 110. The at least one processor 144 may be configured to cause transmission of a primary signal from the primary antenna to implant unit 110, or any other implantable device including at least one pair of modulation electrodes. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158*a*, 158*b*, etc. Amplifier 146 may output the amplified signal to primary antenna 150.

At least one processor 144 may also be configured to receive a condition signal from an implantable device such as implant unit 110. A condition signal may be any type of signal received by the at least one processor, for example via primary antenna 144, from an implantable device. A condition signal may be indicative of movement of the implantable device, location of the implantable device, a maximum power limit of the implantable device, and/or a minimum efficacy threshold of the implantable device. The condition signal may also be indicative of a degree of coupling between primary antenna 144 and secondary antenna 152. A condition signal may include a primary coupled signal component present on the primary antenna due to signals within the implant. A condition signal may also include a signal generated by the implantable device itself, for example, by at least one processor associated the implant. A condition signal may be generated by the implant in response to information generated by the implant, information pertaining to the internal state of the implant, and/or information received by sensors associated with the implant. Various examples of the nature and form of a condition signal are expressed in more detail below.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, a measure of harmonic resonance in the implant, etc. and any combinations thereof.

A degree of coupling between primary antenna 150 and secondary antenna 152 may depend on the proximity of the primary antenna relative to the secondary antenna. As used herein, the term "degree of coupling," may include any measure of electromagnetic interaction between two antennas. For example, a degree of coupling may include a measure of efficiency of energy transfer between two antennas (e.g. primary antenna 150 and secondary antenna 152), a measure of signal strength, a measure of signal arrival time, a measure of travel time of signals between two antennas, and/or any other measure of communication between two antennas. By way of example only, a degree of coupling may be measured in terms of current, voltage, power, elapsed time, arrival time, frequency, phase, one or more ratios of the foregoing, or any other indicator of communication that can be quantified. A degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b. For example, at least one processor 144 may be configured to adjust one or more characteristics of the primary signal to generate either or both of a sub-modulation control signal and a modulation control signal when received by the an implantable device. Adjusted characteristics of a modulation control signal may be referred to as modulation characteristics, hereas adjusted characteristics of a sub-modulation control signal may be referred to as sub-modulation characteristics. The secondary signal on secondary antenna 152 caused by the primary signal may include a modulation control signal, adapted to cause the generation of an electric field sufficient to cause a neuromuscular inducing current across the electrodes of implant unit 110. Additionally, the secondary signal on secondary antenna 152 caused by the primary signal may be a sub-modulation control signal, adapted so as not to cause the generation of an electric field sufficient to cause a neuromuscular inducing current across electrodes of implant unit 110. The adjusted characteristics are explained in greater detail below.

Figure 6:
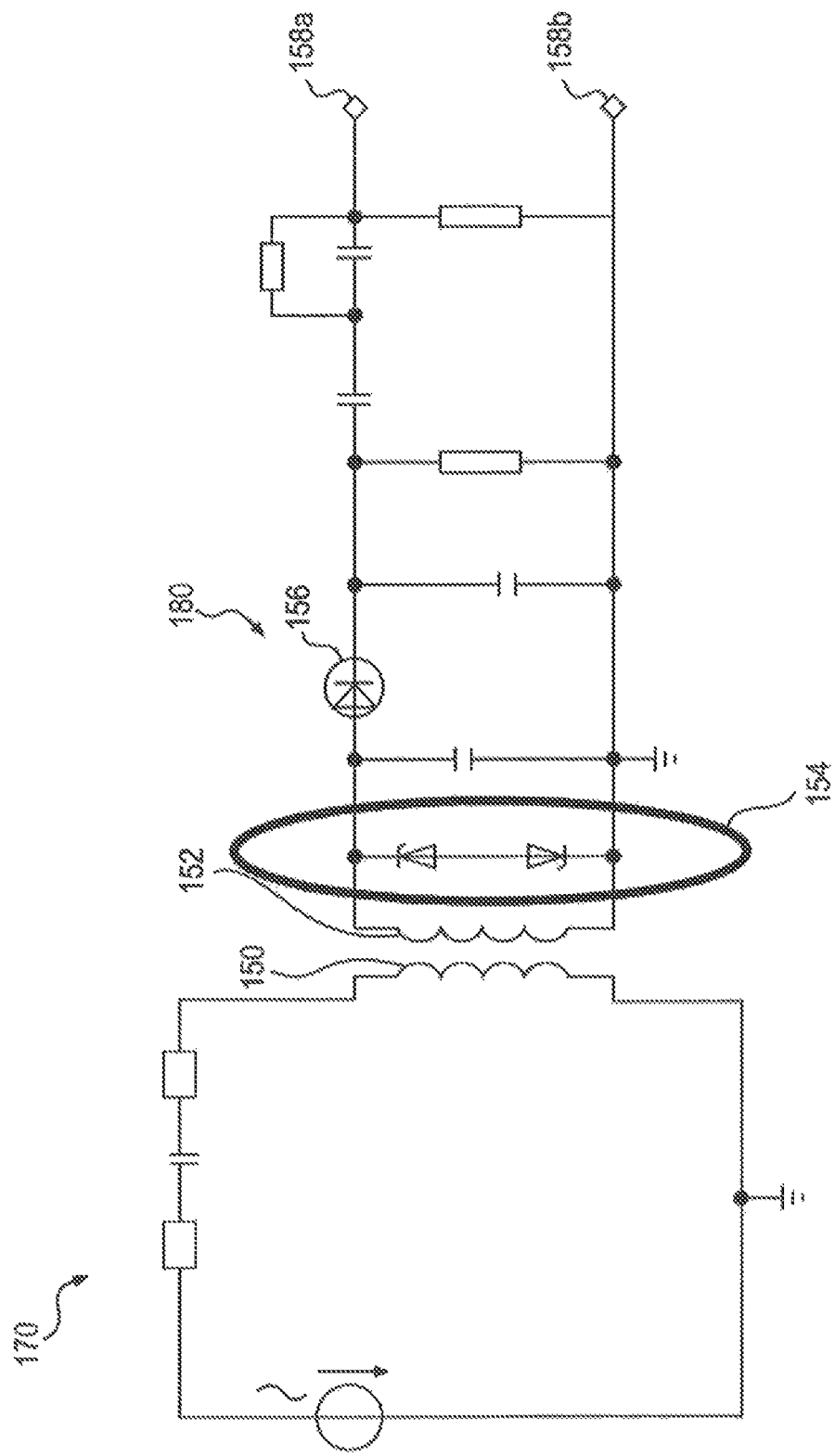
FIG. 6 illustrates circuitry of an implant unit and an external unit, according to an exemplary embodiment of the present disclosure.

FIG. 6 illustrates circuitry 170 that may be included in external unit 120 and circuitry 180 that may be included in implant unit 110 or otherwise associated with implant unit 110. For example, circuitry 180 may be included with implant unit 110 (e.g., provided on flexible carrier 161) or may be included on a substrate or implant element separate from implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry 180 connecting secondary antenna 152 with implant electrodes 158a and 158b may cause a voltage potential across implant electrodes 158a and 158b in the presence of a secondary signal on secondary antenna 152. For example, an implant unit 110 may apply a voltage potential to implant electrodes 158a and 158b in response to an AC signal received by secondary antenna 152. As used herein, the term "voltage potential" may include a voltage signal or any electrical signal. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152 in circuitry 180. In certain embodiments, however, may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include a signal modifier, for example, an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude, orientation, energy density, and/or duration of the generated electric field resulting from the field inducing signal may cause current flow sufficient to modulate one or more nerves in the vicinity of electrodes 158a and 158b. In such cases, the field inducing signal may be referred to as a modulation signal, and the associated primary signal may be referred to as a modulation control signal. In other instances, the magnitude and/or duration of the field inducing signal may generate an electric field that does not result in nerve modulation. In such cases, the field inducing signal may be referred to as a sub-modulation signal.

Various characteristics of the primary control signal may be adjusted by processor 144 so as to cause differing responses in the implant. For example, characteristics of the primary control signal may be adjusted to cause various types of field inducing signals, both modulation signals and sub-modulation signals, at electrodes 158a and 158b of implant unit 110. Adjusted characteristics may include, for example, voltage, current, frequency, pulse rate, pulse width, and signal duration. For example, in some embodiments, a modulation signal may include a moderate amplitude (defined by voltage or current) and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.). For example, the modulation signal may include a voltage between about 0.5 volts and about 40 volts or electric current between about 50 microamps and about 20 milliamps.

In some embodiments, the electrodes 158a and 158b may generate an electric field configured to penetrate intervening tissue 111 between the electrodes and one or more nerves. The intervening tissue 111 may include muscle tissue, bone, connective tissue, adipose tissue, organ tissue, or any combination thereof. For subjects suffering with obstructive sleep apnea, for instance, the intervening tissue may include the genioglossus muscle.

As noted above, electrodes 158a, 158b may have various different configurations, and in some embodiments, the electrodes may be configured to emit a unidirectional electric field (e.g., in response to an applied DC voltage signal). Electrodes 158a, 158b may further be configured such that modulation of at least one nerve in the vicinity of the electrodes may be accomplished when non-nerve tissue is interposed between the electrodes and the at least one nerve. For example, such non-nerve tissue may include muscle tissue, connective tissue, fat, blood vessel, mucosal membrane, etc. may interposed between the electrodes and the nerve to be modulated. Electrodes 158a, 158b may be configured such that an electric field generated by the electrodes can penetrate the tissue interposed between the electrodes and the at least one nerve to be modulated. For example, in some embodiments the electrodes may be configured to generate an electric field enabling modulation of the at least one nerve when the tissue interposed between the electrodes and the at least one nerve has a thickness of greater than about 1 mm. In other embodiments the electrodes may be configured to generate an electric field enabling modulation of the at least one nerve when the tissue interposed between the electrodes and the at least one nerve has a thickness of greater than about 5 mm. In still other embodiments, the electrodes may be configured to generate an electric field enabling modulation of the at least one nerve when the electrodes and the at least one nerve are spaced apart by a distance between about 5 mm and 15 mm, or a distance between 0.1 mm and 25 mm.

Figure 10A:
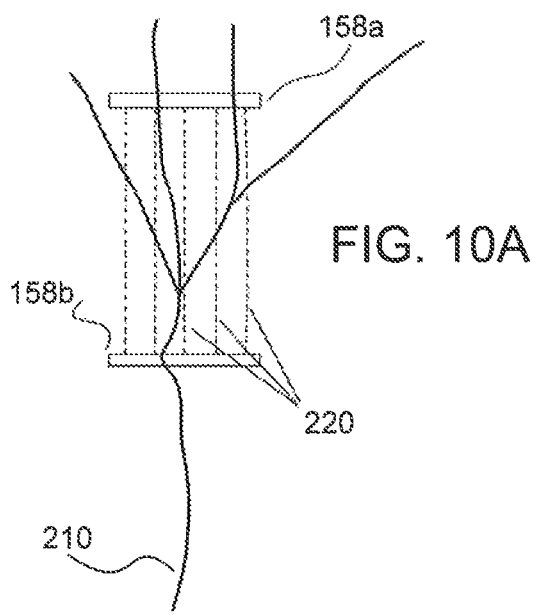
FIG. 10a illustrates an embodiment wherein electrodes are spaced apart from one another in a longitudinal direction of at least a portion of a nerve.
Figure 10B:
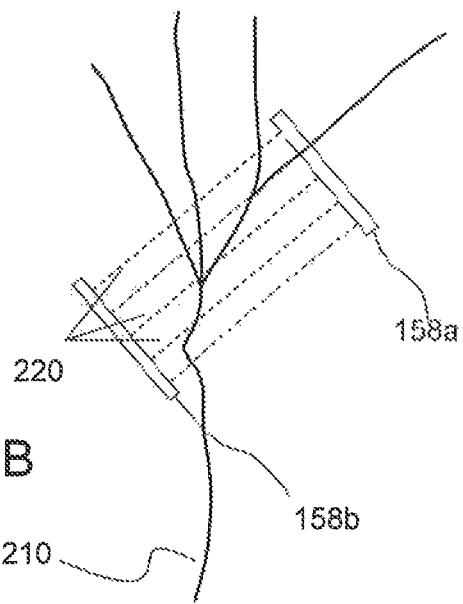
FIG. 10b illustrates an embodiment wherein electrodes are spaced apart from one another in a longitudinal direction of at least a portion of a nerve.
Figure 10C:
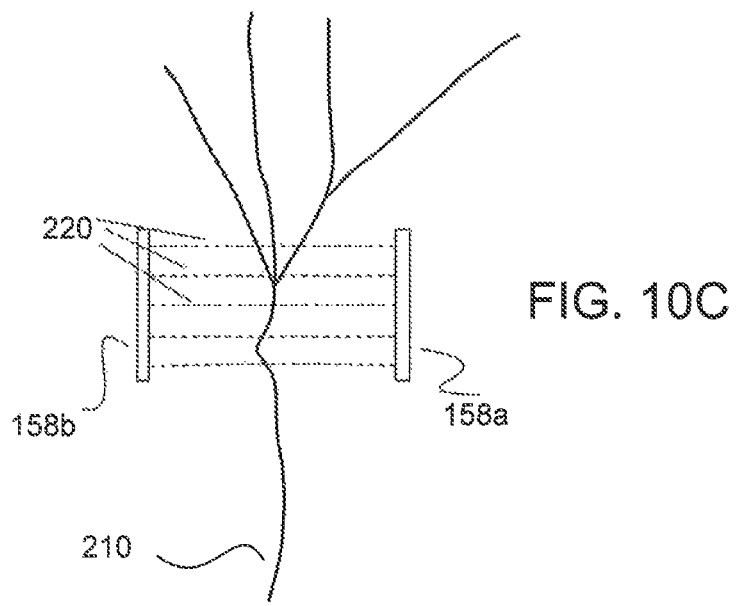
FIG. 10c illustrates a situation wherein electrodes are spaced apart from one another in a transverse direction of a nerve.

As used herein, the term substantially unidirectional electric field may refer to an electric field having field lines parallel to one another, when viewed from an angle orthogonal to a plane on which the electrodes facilitating the electric field are located. For example, the electric field lines 220 illustrated in FIGS. 10A, 10B, and 10C are parallel to one another when viewed from above the drawing sheet on which the electrodes 158a, and 158b are located. It is to be understood that, while electric field lines at the edges of electrodes 158a, 158b may curve out from substantially parallel electric field lines 220, the field generated may still be considered to be substantially unidirectional as a substantial portion of current passed between electrodes 158a and 158b travels along parallel electric field lines.

The generation of electric fields configured to penetrate intervening tissue now discussed with respect to FIGS. 10a, 10b, 10c and 11. In response to a field inducing signal, implant electrodes 158a and 158b may be configured to generate a unidirectional electric field with field lines extending generally in the longitudinal direction of one or more nerves to be modulated. In some embodiments, implant electrodes 158a and 158b may be spaced apart from one another along the longitudinal direction of a nerve to facilitate generation of such an electric field. The unidirectional electric field may also be configured to extend in a direction substantially parallel to a longitudinal direction of at least some portion of the nerve to be modulated. For example, a substantially parallel field may include field lines that extend more in a longitudinal direction than a transverse direction compared to the nerve. Orienting the electric field in this way may facilitate electrical current flow through a nerve or tissue, thereby increasing the likelihood of eliciting an action potential to induce modulation.

FIG. 10a illustrates a pair of electrodes 158a, 158b spaced apart from one another along the longitudinal direction of nerve 210 to facilitate generation of an electric field having field lines 220 substantially parallel to the longitudinal direction of nerve 210. In 10a, modulation electrodes 158a, 158b are illustrated as line electrodes, although the generation of substantially parallel electric fields may be accomplished through the use of other types of electrodes, including, for example, a series of point electrodes. Utilizing an electric field having field lines 220 extending in a longitudinal direction of nerve 210 may serve to reduce the amount of energy required to achieve neural modulation.

Second, more ion channels may be recruited by expanding the area affected by the voltage potential difference.

Returning to 10a, it can be seen that, due to the electric field lines 220 running in a direction substantially parallel to the longitudinal direction of the nerve 210, a large portion of nerve 210 may encounter the field. Thus, more ion channels from the neurons that make up nerve 210 may be recruited without using a larger voltage potential difference. In this way, modulation of nerve 210 may be achieved with a lower current and less power usage. FIG. 10b illustrates an embodiment wherein electrodes 158a and 158 are still spaced apart from one another in a longitudinal direction of at least a portion of nerve 210. A significant portion of nerve 210 remains inside of the electric field. FIG. 10c illustrates a situation wherein electrodes 158a and 158b are spaced apart from one another in a transverse direction of nerve 210. In this illustration, it can be seen that a significantly smaller portion of nerve 210 will be affected by electric field lines 220.

Figure 11:
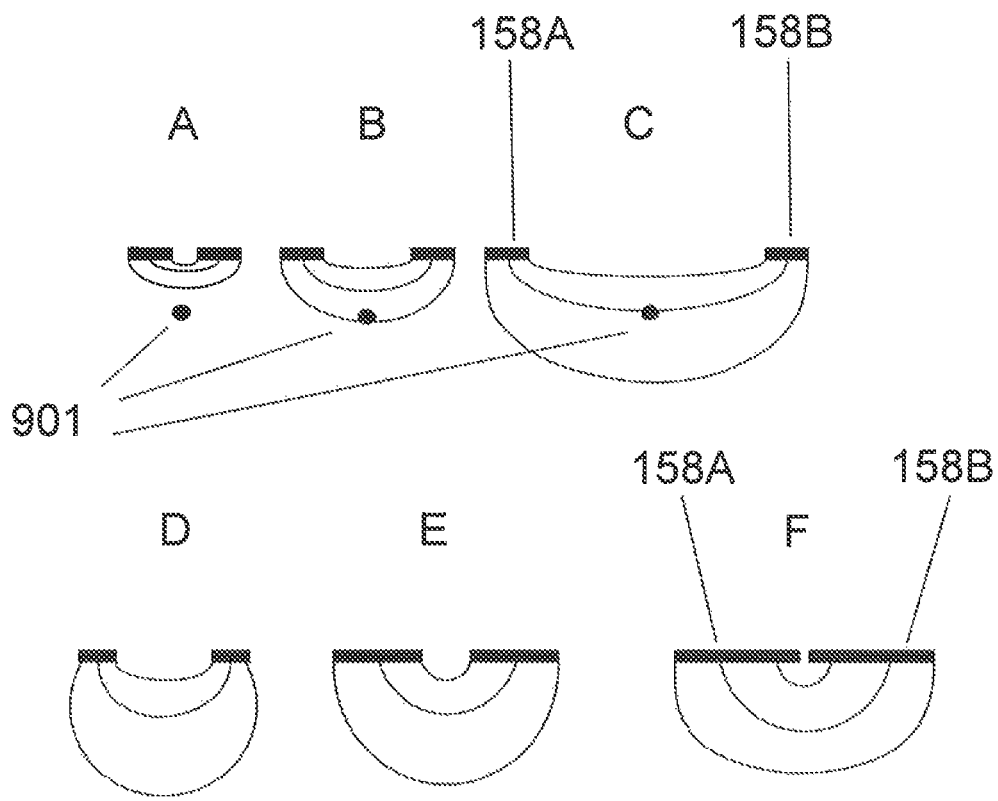
FIG. 11 illustrates effects of electrode configuration on the shape of a generated electric field.

FIG. 11 illustrates potential effects of electrode configuration on the shape of a generated electric field. The top row of electrode configurations, e.g. A, B, and C, illustrates the effects on the electric field shape when a distance between electrodes of a constant size is adjusted. The bottom row of electrode configurations, e.g. D, E, and F illustrates the effects on the electric field shape when the size of electrodes of constant distance is adjusted.

In embodiments consistent with the present disclosure, modulation electrodes 158a, 158b may be arranged on the surface of a muscle or other tissue, in order to modulate a nerve embedded within the muscle or other tissue. Thus, tissue may be interposed between modulation electrodes 158a, 158b and a nerve to be modulated. Modulation electrodes 158a, 158b may be spaced away from a nerve to be modulated. The structure and configuration of modulation electrodes 158a, 158b may play an important role in determining whether modulation of a nerve, which is spaced a certain distance away from the electrodes, may be achieved.

Electrode configurations A, B, and C show that when modulation electrodes 158a, 158b of a constant size are moved further apart, the depth of the electric field facilitated by the electrodes increases. The strength of the electric field for a given configuration may vary significantly depending on a location within the field. If a constant level of current is passed between modulation electrodes 158a and 158b, however, the larger field area of configuration C may exhibit a lower overall current density than the smaller field area of configuration A. A lower current density, in turn, implies a lower voltage potential difference between two points spaced equidistant from each other in the field facilitated by configuration C relative to that of the field facilitated by configuration A. Thus, while moving modulation electrodes 158a and 158b farther from each other increases the depth of the field, it also decreases the strength of the field. In order to modulate a nerve spaced away from modulation electrodes 158a, 158b, a distance between the electrodes may be selected in order to facilitate an electric field of strength sufficient to surpass a membrane threshold potential of the nerve (and thereby modulate it) at the depth of the nerve. If modulation electrodes 158a, 158b are too close together, the electric field may not extend deep enough into the tissue in order to modulate a nerve located therein. If modulation electrodes 158a, 158b are too far apart, the electric field may be too weak to modulate the nerve at the appropriate depth.

Appropriate distances between modulation electrodes 158a, 158b, may depend on an implant location and a nerve to be stimulated. For example, modulation point 901 is located at the same depth equidistant from the centers of modulation electrodes 158a, 158b in each of configurations A, B, and C, The figures illustrate that, in this example, configuration B is most likely to achieve the highest possible current density, and therefore voltage potential, at modulation point 901. The field of configuration A may not extend deeply enough, and the field of configuration C may be too weak at that depth.

In some embodiments, modulation electrodes 158a, 158b may be spaced apart by about a distance of about 0.2 mm to 25 mm. In additional embodiments, modulation electrodes 158a, 158b may be spaced apart by a distance of about 1 mm to 10 mm, or between 4 mm and 7 mm. In other embodiments modulation electrodes 158a, 158b may be spaced apart by between approximately 6 mm and 7 mm.

Electrode configurations D, E, and F show that when modulation electrodes 158a, 158b of a constant distance are changed in size, the shape of the electric field facilitated by the electrodes changes. If a constant level of current is passed between when modulation electrodes 158a and 158b, the smaller electrodes of configuration D may facilitate a deeper field than that of configurations E and F, although the effect is less significant relative to changes in distance between the electrodes. As noted above, the facilitated electric fields are not of uniform strength throughout, and thus the voltage potential at seemingly similar locations within each of the electric fields of configurations D, E, and, F may vary considerably. Appropriate sizes of modulation electrodes 158a, 158b, may therefore depend on an implant location and a nerve to be stimulated.

In some embodiments, modulation electrodes 158a, 158b may have a surface area between approximately 0.01 $mm^2$ and 80 $mm^2$. In additional embodiments, modulation electrodes 158a, 158b may have a surface area between approximately 0.1 $mm^2$ and 4 $mm^2$. In other embodiments modulation electrodes 158a, 158b may have a surface area of between approximately 0.25 $mm^2$ and 0.35 $mm^2$.

In some embodiments, modulation electrodes 158a, 158b may be arranged such that the electrodes are exposed on a single side of carrier 161. In such an embodiment, an electric field is generated only on the side of carrier 161 with exposed electrodes. Such a configuration may serve to reduce the amount of energy required to achieve neural modulation, because the entire electric field is generated on the same side of the carrier as the nerve, and little or no current is wasted traveling through tissue away from the nerve to be modulated. Such a configuration may also serve to make the modulation more selective. That is, by generating an electric field on the side of the carrier where there is a nerve to be modulated, nerves located in other areas of tissue (e.g. on the other side of the carrier from the nerve to be modulated), may avoid being accidentally modulated.

As discussed above, the utilization of electric fields having electrical field lines extending in a direction substantially parallel to the longitudinal direction of a nerve to be modulated may serve to lower the power requirements of modulation. This reduction in power requirements may permit the modulation of a nerve using less than 1.6 mA of current, less than 1.4 mA of current, less than 1.2 mA of current, less than 1 mA of current, less than 0.8 mA of current, less than 0.6 mA of current, less than 0.4 mA of current, and even less than 0.2 mA of current passed between modulation electrodes 158a, 158b.

Reducing the current flow required may have additional effects on the configuration of implant unit 110 and external unit 120. For example, the reduced current requirement may enable implant unit 110 to modulate a nerve without a requirement for a power storage unit, such as a battery or capacitor, to be implanted in conjunction with implant unit 110. For example, implant unit 110 may be capable of modulating a nerve using only the energy received via secondary antenna 152. Implant unit 110 may be configured to serve as a pass through that directs substantially all received energy to modulation electrodes 158a and 158b for nerve modulation. Substantially all received energy may refer to that portion of energy that is not dissipated or otherwise lost to the internal components of implant unit 110. Finally, the reduction in required current may also serve to reduce the amount of energy required by external unit 120. External unit 120 may be configured to operate successfully for an entire treatment session lasting from one to ten hours by utilizing a battery having a capacity of less than 240 mAh, less than 120 mAh, and even less than 60 mAh.

As discussed above, utilization of parallel fields may enable implant unit 110 to modulate nerves in a non-contacting fashion. Contactless neuromodulation may increase the efficacy of an implanted implant unit 110 over time compared to modulation techniques requiring contact with a nerve or muscle to be modulated. Over time, implantable devices may migrate within the body. Thus, an implantable device requiring nerve contact to initiate neural modulation may lose efficacy as the device moves within the body and loses contact with the nerve to be modulated. In contrast, implant unit 110, utilizing contactless modulation, may still effectively modulate a nerve even if it moves away from, or to another location relative to an initial implant location. Additionally, tissue growth and/or fibrosis may develop around an implantable device. This growth may serve to lessen or even eliminate the contact between a device designed for contact modulation and a nerve to be modulated. In contrast, implant unit 110, utilizing contactless modulation, may continue to effectively modulate a nerve if additional tissue forms between it and a nerve to be modulated.

As described above, modulation electrodes 158a, 158b, of implant unit 110 may be configured so as to facilitate the generation of an electric field sufficient to modulate a nerve even when a voltage signal of low current is applied to modulation electrodes 158a, 158b. In some embodiments consistent with the present disclosure, implant unit 110 may have no means of measuring the current of a voltage signal applied to modulation electrodes 158a, 158b. In such an embodiment, processor 144 may be configured to supply a voltage signal having a specific current value, for example, less than about 1.6 mAmps, as follows. Processor 144 may be configured to adjust the characteristics, for example, the voltage, of a primary signal. Processor 144 may detect coupling between primary antenna 152 and secondary antenna 162, and therefore determine the voltage of the secondary signal induced on the secondary antenna 162 by the primary signal. The voltage induced in the implant may drive a certain amount of current through the circuitry 180 of the implant to modulation electrodes 158a, 158b. The amount of current driven through the implant unit 110 may depend on the voltage of the secondary signal, the configuration of implant circuitry 180, and the resistance between modulation electrodes 158a, 158b. The resistance between modulation electrodes 158a, 158b, may vary for physiological reasons because tissue closes the circuit. Implant positioning, tissue composition, tissue hydration, and other physiological factors may all affect the resistance, and thus the current across the electrodes. The resistance, however, will vary within a small range, and the known factors, such as implant circuitry 180, may dominate these small variations. Thus, processor 144 may be configured with information about a configuration of implant unit 110, modulation electrodes, 158a, 158b, and ranges of variation of tissue impedance so as to be able to adjust the primary signal to an appropriate voltage in order to deliver the specified amount of current to modulation electrodes 158a, 158b in order to modulate a nerve.

The circuitry 180 of implant unit 110 may also be configured to deliver to the electrodes an electrical signal having a current less than about 1.6 milliamps. That is, the design of the implant circuitry 180, the values of the resistors, capacitors, diodes, and other electronic components of implant circuitry 180 may be chosen specifically such that when a primary signal on primary antenna 152 induces a secondary signal on secondary antenna 162, the voltage of the secondary signal will be sufficient to drive the specified amount of current across modulation electrodes 158a, 158b, in order to modulate a nerve.

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

In some embodiments, processor 144 may be configured to adjust the one or more characteristics of the primary signal so as to elicit the condition signal from an implantable device. For example, when transmitted to an implantable device such as implant unit 110, the primary signal may be adjusted in order to cause a secondary signal in implant unit 110 that, in turn, causes a primary coupled signal component on primary antenna 144. Such adjustments may, for example, be calculated to cause implant unit 110 to generate a specific type of harmonic resonance, as described further below. In other examples, a primary signal may be adjusted by processor 144 to communicate with a processor associated with an implantable device, and to thereby elicit a condition signal from the processor associated with the implantable device in response.

In some embodiments, a modulation signal resulting in neural stimulation may be provided by electrodes 158a and 158b in response to one or more electrical signals (e.g. signals having various voltage levels, current levels, or durations) supplied by circuitry 180. Such stimulation may result even when each supplied electrical signal has a current of less than about 1 millliamp. In such embodiments, electrodes 158a and 158b may be configured to emit an electric field such that at least a portion of the field lines extend along a length of the nerve such that the delivery of the electrical signal of less than about 1.6 milliamps causes stimulation of the nerve. Circuitry 180 (including various capacitor values, diode activation potentials, etc.) may be configured to deliver a substantial portion of the energy received from external unit 120 to the subject within about 1 second or less of receiving the energy.

As discussed above, implant unit 110 may be secured to the surface of non-nerve tissue. One or more of muscle tissue, connective tissue, fat, blood vessel, and mucosal membrane may be interposed between the electrodes and the nerve. The electrodes may be configured to generate an electric field sufficient to stimulate the underlying nerve with less than 1.6 milliamps of current.

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. For example, components including diodes may be included in implant unit 110 or in external unit 120 to limit power transferred from the external unit 120 to the implant unit 110. In some embodiments, diode 156 may function to limit or substantially restrict the power level received by the patient. Processor 144 may be configured to account for such limitations when setting the magnitude and/or duration of a primary signal to be applied to primary antenna 150. As described above, this information may be received by processor 144 via a condition signal from the implantable device indicative of a maximum power limit.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals). As described above, this information may be received by processor 144 via a condition signal from the implantable device indicative of a minimum efficacy threshold.

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158*a*, 158*b*. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. Measuring the degree of coupling may enable determination of the efficacy of the energy transfer between two antennas. Processor 144 may also use the determined degree of coupling in regulating delivery of power to implant unit 110.

In some embodiments consistent with the present disclosure, processor 144 may be configured to adjust the one or more characteristics of the primary signal based on the condition signal from the implantable device. For example, as described in greater detail below, a condition signal indicative of coupling between primary antenna 150 and secondary antenna 152 may be used by the processor to determine a suitable response. In other examples, a processor associated with an implantable device may generate and cause the transmission of a condition signal containing information which the at least one processor 144 may use to adjust the characteristics of the primary signal.

Processor 144 may be configured with any suitable logic for determining how to regulate power transfer to implant unit 110 based on the determined degree of coupling. Processor 144 may, for example, utilize a baseline coupling range. Presumably, while the patient is awake, the tongue is not blocking the patient's airway and moves with the patient's breathing in a natural range, where coupling between primary antenna 150 and secondary antenna 152 may be within a baseline coupling range. A baseline coupling range may encompass a maximum coupling between primary antenna 150 and secondary antenna 152. A baseline coupling range may also encompass a range that does not include a maximum coupling level between primary antenna 150 and secondary antenna 152. Processor 144 may be configured to determine the baseline coupling range based on a command from a user, such as the press of a button on the patch or the press of a button on a suitable remote device. Alternatively or additionally, processor 144 may be configured to automatically determine the baseline coupling range when external unit 120 is placed such that primary antenna 150 and secondary antenna 152 are within range of each other. In such an embodiment, when processor 144 detects any degree of coupling between primary antenna 150 and secondary antenna 152, it may immediately begin tracking a baseline coupling range. Processor 144 may then determine a baseline coupling range when it detects that the only movement between primary antenna 150 and secondary antenna 152 is caused by a patient's natural breathing rhythm (i.e., the patient has secured the external unit to an appropriate location on their body). Additionally, processor 144 may be configured such that it measures coupling between the primary antenna 150 and the secondary antenna 152 for a specified period of time after activation in order to determine a baseline coupling range, such as 1 minute, 5 minutes, 10 minutes, etc.

A condition signal, for example, a primary coupled signal component, may indicate that a degree of coupling has changed from a baseline coupling range, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. The condition signal, therefore, may be indicative of movement and/or location of the implantable device. In such situations, processor 144 may determine that modulation of a nerve in the patient's body is appropriate. In some embodiments, a condition signal indicative of a predetermined amount of movement of the implantable device may trigger the transmission of the primary signal. For example, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be indicative of tongue movement associated with sleep disordered breathing, such as the onset of a sleep apnea event or a sleep apnea precursor. An amount of tongue movement may be indicative of the severity of the sleep disordered breathing. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking (i.e. a down modulation) of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular vein (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal (i.e. a down modulation) at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission. The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an ion channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

The number of ion channels recruited by a voltage potential difference may be increased in at least two ways. First, more ion channels may be recruited by utilizing a larger voltage potential difference in a local area. Second, more ion channels may be recruited by expanding the area affected by the voltage potential difference. In some embodiments, the at least one processor may be configured to cause transmission of a primary signal from the primary antenna to an implantable device during a treatment session of at least three hours in duration. During such a treatment such, the primary signal may be generated using power supplied by power source associated with the processor, such as a battery. The primary signal during such a treatment session may include a pulse train, as illustrated, for example, in FIG. 10.

Figure 17:
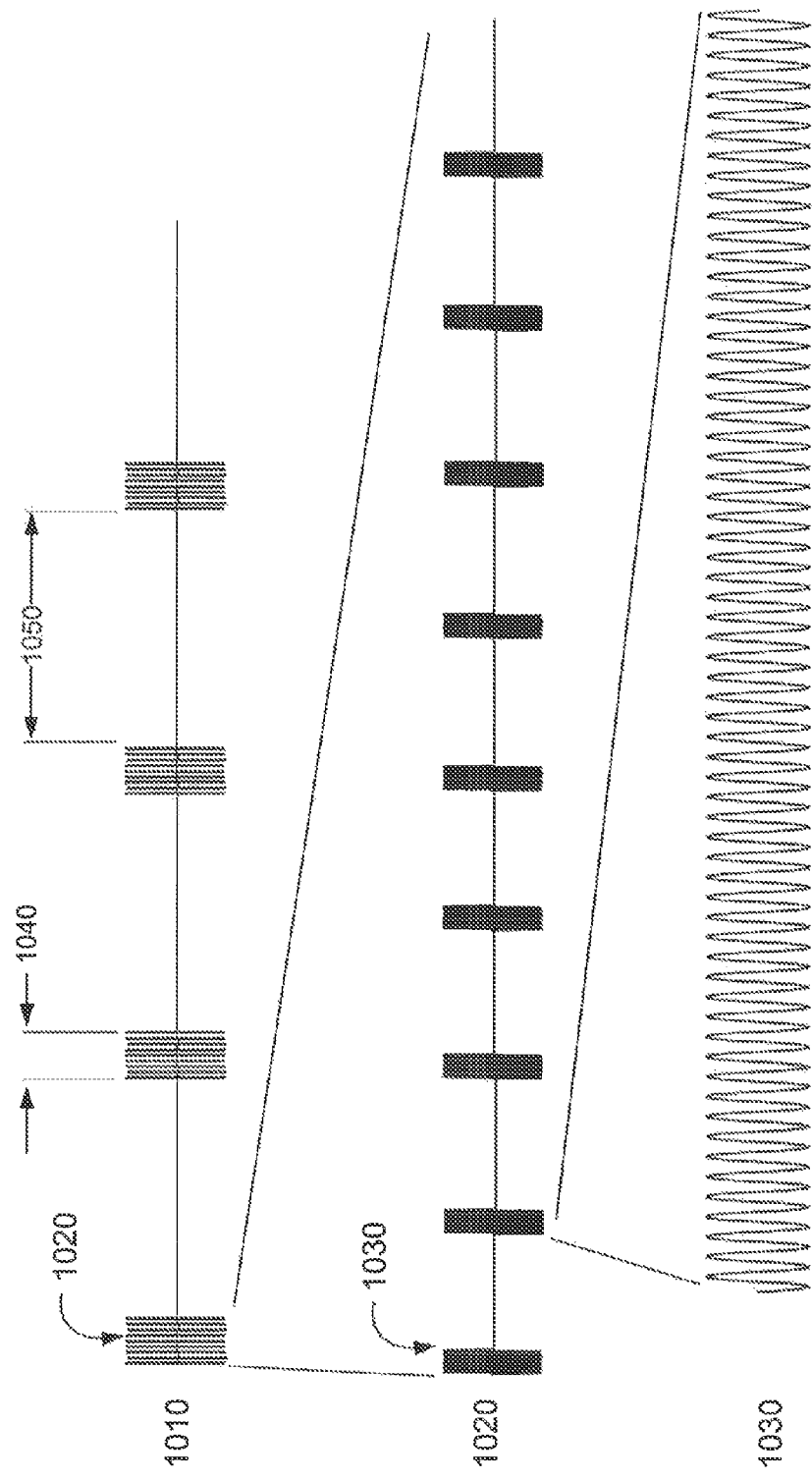
FIG. 17 depicts the composition of an exemplary modulation pulse train.

FIG. 17 depicts the composition of an exemplary modulation pulse train. Such a pulse train 1010 may include a plurality of modulation pulses 1020, wherein each modulation pulse 1020 may include a plurality of modulation sub-pulses 1030. FIG. 17 is exemplary only, at a scale appropriate for illustration, and is not intended to encompass all of the various possible embodiments of a modulation pulse train, discussed in greater detail below. An alternating current signal (e.g., at a frequency of between about 6.5-13.6 MHz) may be used to generate a pulse train 1010, as follows. A sub-pulse 1030 may have a pulse duration of between 50-250 microseconds, or a pulse duration of between 1 microsecond and 2 milliseconds, during which an alternating current signal is turned on. For example, a 200 microsecond sub-pulse 1030 of a 10 MHz alternating current signal will include approximately 2000 periods. Each modulation pulse 1020 may, in turn, have a pulse duration 1040 of between 100 and 500 milliseconds, during which sub-pulses 1030 occur at a frequency of between 25 and 100 Hz. Thus a modulation pulse 1020 may include between about 2.5 and 50 modulation sub-pulses 1030. In some embodiments, a modulation 1020 pulse may include between about 5 and 15 modulation sub-pulses 1030. For example, a 200 millisecond modulation pulse 1020 of 50 Hz modulation sub-pulses 1030 will include approximately 10 modulation sub-pulses 1030. Finally, in a modulation pulse train 1010, each modulation pulse 1020 may be separated from the next by a temporal spacing 1050 of between 0.2 and 2 seconds. For example, in a pulse train 1010 of 200 millisecond pulse duration 1040 modulation pulses 1020, each separated by a 1.3 second temporal spacing 1050 from the next, a new modulation pulse 1020 will occur every 1.5 seconds. The frequency of modulation pulses 1020 may also be timed to in accordance with physiological events of the subject. For example, modulation pulses 1020 may occur at a frequency chosen from among any multiple of a breathing frequency, such as four, eight, or sixteen. In another example, modulation pulses 1020 may be temporally spaced so as not to permit a complete relaxation of a muscle after causing a muscular contraction. The pulse duration 1040 of modulation pulses 1020 and the temporal spacing 1050 between modulation pulses 1020 in a pulse train 1010 may be maintained for a majority of the modulation pulses 1020, or may be varied over the course of a treatment session according to a subject's need. Such variations may also be implemented for the modulation sub-pulse duration and temporal spacing.

Pulse train 1010 depicts a primary signal pulse train, as generated by external unit 120. In some embodiments, the primary signal may result in a secondary signal on the secondary antenna 152 of implant unit 110. This signal may be converted to a direct current signal for delivery to modulation electrodes 158a, 158b. In this situation, the generation of modulation sub-pulse 1030 may result in the generation and delivery of a square wave of a similar duration as modulation sub-pulse 1030 to modulation electrodes 158a, 158b.

In an embodiment for the treatment of sleep disordered breathing, modulation pulses 1020 and modulation sub-pulses 1030 may include stimulation pulses and stimulation sub-pulses adapted to cause neural stimulation. A pulse train 1010 of this embodiment may be utilized, for example, to provide ongoing stimulation during a treatment session. Ongoing stimulation during a treatment session may include transmission of the pulse train for at least 70%, at least 80%, at least 90%, and at least 99% of the treatment session. In the context of sleep disordered breathing, a treatment session may be a period of time during which a subject is asleep and in need of treatment to prevent sleep disordered breathing. Such a treatment session may last anywhere from about three to ten hours. A treatment session may include as few as approximately 4,000 and as many as approximately 120,000 modulation pulses 1020. In some embodiments, a pulse train 1010 may include at least 5,000, at least 10,000, and at least 100,000 modulation pulses 1020. In the context of other conditions to which neural modulators of the present disclosure are applied, a treatment session may be of varying length according to the duration of the treated condition.

Exemplary treatment regimes for head pain management and hypertension therapy may differ from a sleep disordered breathing treatment regime. For example, in an exemplary head pain management treatment regime, temporal spacing 1050 may be reduced to less than 3 milliseconds, less than 2 milliseconds, less than 1 millesecond, or even eliminated altogether. Furthermore, the spacing between sub-pulses 1030 may also be reduced to less than 3 milliseconds, less than 2 milliseconds, less than 1 millesecond, or even eliminated altogether. The amplitude of sub-pulses 1030 and pulses 1020 may be reduced to a level sufficient to recruit ion channels as blocks but not elicit an action potential. A duration of sub-pulses 1030 may also be reduced to between about 50 microseconds and 100 microseconds. Thus, pulse train 1010 may be adapted to maintain a plurality of ion channels as blocks that will not permit the propagation of action potentials along the nerve. When such a pulse train 1010 is applied to a nerve that typically carries a pain signal, such as a greater occipital nerve, lesser occipital nerve, or trigeminal nerve, the amount of pain experienced by a subject may be reduced. Temporal spacing 1050 and spacing between sub-pulses 1030 may be reduced such that the recruited ion channels do not have enough time to restore their ion concentrations in preparation for activation. Thus, an effective neural block may still be created without a constant modulation. A pulse train 1010 where temporal spacing 1050 and spacing between sub-pulses 1030 is not entirely eliminated may be valuable for conserving power.

Exemplary hypertension therapy regimes may vary based on implant location. For example, an exemplary hypertension therapy regime for applying neural modulation to a renal nerve may be similar to a head pain management treatment regime, as the objective is to reduce or eliminate the signals sent along the renal nerve. Such treatment may be valuable because the active propagation of signals along the renal nerve may indicate a need to increase blood pressure.

In contrast, active propagation of signals from the carotid baroreceptor, which travel along the glossopharyngeal nerve, may indicate a need to reduce blood pressure. Thus, an exemplary hypertension therapy regime for applying neural modulation to a carotid baroreceptor or glossopharyngeal nerve may involve stimulation pulses to propagate action potentials. Functioning normally, signals propagating from the carotid baroreceptors along the glossopharyngeal nerve indicate a need to reduce blood pressure through an increased frequency of signals. Thus, an exemplary pulse train 1010 for treatment of hypertension by applying neural modulation to a carotid baroreceptor or glossopharyngeal nerve may involve a reduction in pulse duration 1040, temporal spacing 1050, and spacing between sub-pulses 1030, thereby increasing the frequency of pulses 1020 and sub-pulses 1030. Sub-pulse duration 1030 may be reduced because it is only required to send a brief action potential, or spike, along the nerve, (e.g. rather than a sustained signal to cause a muscle to continuously contract). Temporal spacing 1050 may be eliminated or reduced to increase the frequency of spikes so as to indicate to the brain a need for blood pressure reduction. Sub-pulse duration 1030 may be reduced to between about 100 microseconds and 50 microseconds. Spacing between sub-pulses 1030 may be altered such that sub-pulses 1030 occur at a rate of between about 2 to 100 Hz. During a hypertension treatment session, a pulse train 1010, as described above, may be delivered for approximately thirty seconds every minute, every five minutes, every ten minutes, every thirty minutes, or even every hour.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event, moves in a manner consistent with a precursor of sleep apnea, or moves in any other manner (e.g., vibration, etc.), the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value. Such a predetermined amount of change in the primary coupled signal component may be associated with a predetermined amount of movement of the implantable device.

Figure 7:
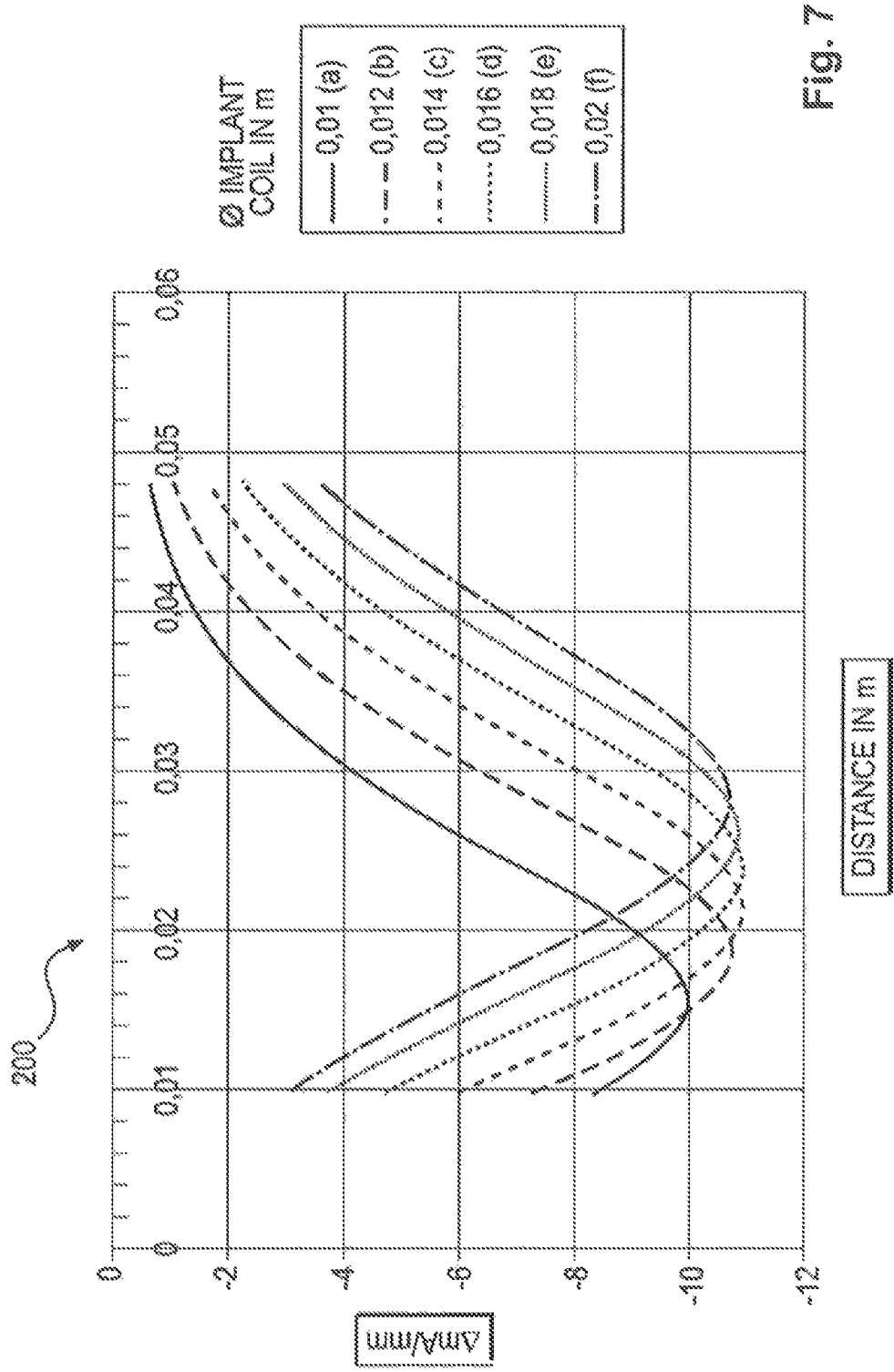
FIG. 7 illustrates a graph of quantities that may be used in determining energy delivery as a function coupling, according to an exemplary disclosed embodiment.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate (or harmonically resonate) at multiple frequencies. The harmonic resonance may be symmetric or asymmetric. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
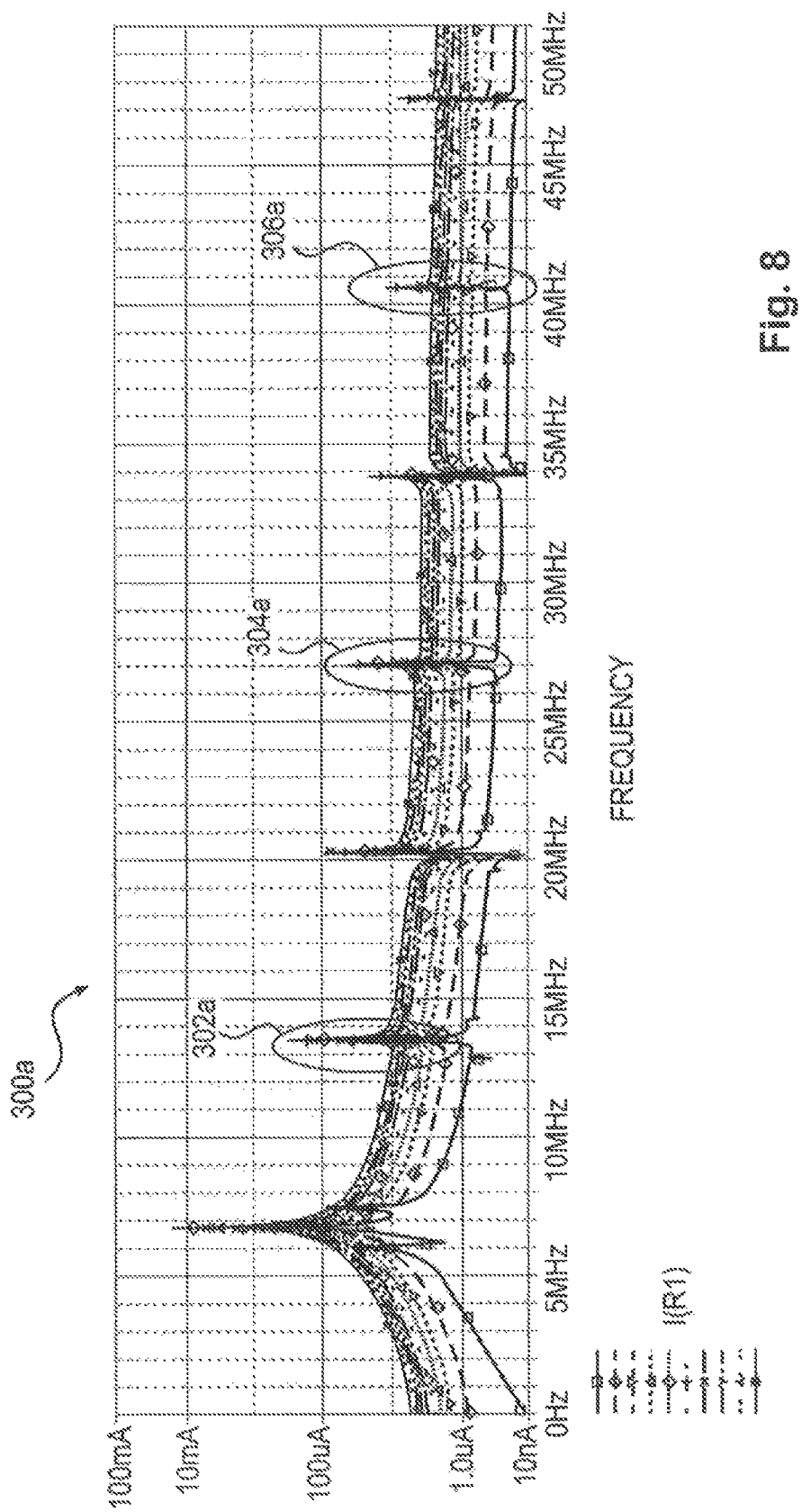
FIG. 8 depicts a graph illustrating non-linear harmonics.
Figure 9:
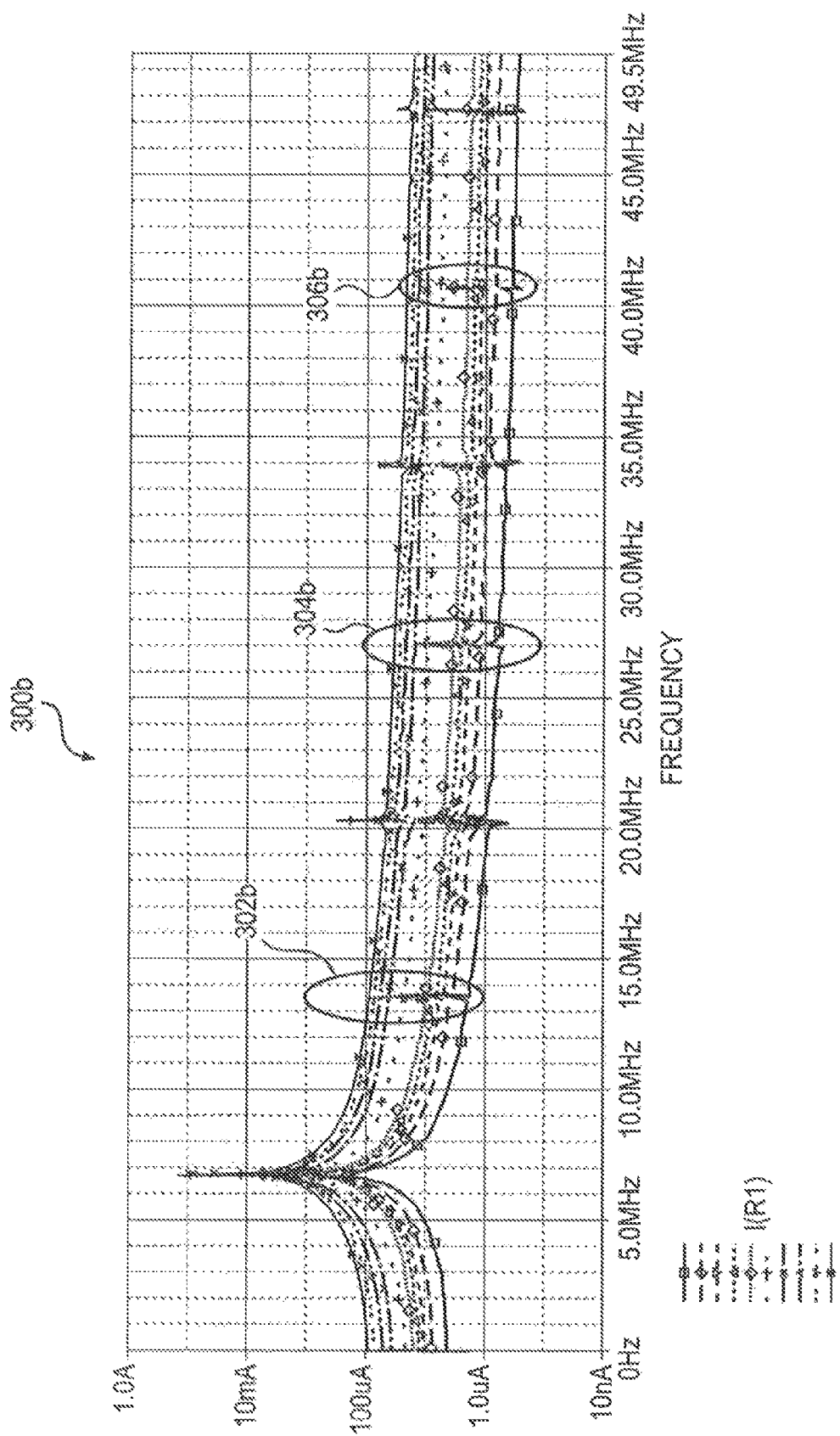
FIG. 9 depicts a graph of quantities that may be used in determining energy delivery as a function coupling, according to an exemplary disclosed embodiment.

FIGS. 8 and 9 illustrate this effect. For example, FIG. 8 illustrates a graph 300a that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300b that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302b, 304b, and 306b, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, from a location remote from implant unit 110, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figures illustrate data based around a 6.7 MHz excitation frequency. These principles, however, are not limited to the 6.7 MHz excitation frequency illustrated, and may be used with a primary signal of any suitable frequency.

In embodiments utilizing non-linear harmonics, the determined amplitude of the primary signal corresponding to the transition level of the Zener diodes (which may be referred to as a primary signal transition amplitude) may establish the baseline coupling range when the patient attaches external unit 120 to the skin. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling which may, for example, be indicative of movement of the tongue) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158*a*, 158*b* throughout a modulation event. For example, processor 144 may after the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g, during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc. Accordingly, processor 144 may be configured to receive a signal from implant unit 110 indicative of tongue movement in a patient.

Tongue movement may be defined or detected in various ways. For example, in one embodiment, tongue movement may be associated with a measurement of the absolute movement of the tongue with respect to external unit 120. Alternatively, or in addition, tongue movement may be associated with a measurement of a relative displacement. For example, the distance between implant unit 110 and external unit 120 may vary over a certain range, and a measurement of relative displacement of tongue movement may include a representation of that range. Moreover, in a further embodiment, tongue movement may include a representation of the speed and/or direction at which the tongue is moving.

Processor 144 may accordingly be configured to determine whether the tongue movement is representative of a sleep disordered breathing based on the signal received that is indicative of tongue movement. The sleep disordered breathing may include, but is not limited to, an apnea precursor, hypopnea, or a hypopnea precursor. Processor 144 may be configured to determine the occurrence of sleep disordered breathing prior to a total obstruction apnea event. That is, processor 144 may be configured to determine when a partial obstruction event occurs, respond to that partial obstruction event, and thereby prevent a total obstruction apnea event from occurring. This determination may be accomplished by the processor comparing the signal information indicative of tongue movement to any suitable baseline from which a sleep disordered breathing condition may be determined. For example, the baseline may include data stored in a lookup table or other form of accessible database. The baseline may include data reflective of a normal tongue movement of the subject. Any suitable baseline may be used to represent normal tongue movement and to enable a qualitative or quantitative determination of when a detected tongue movement varies from normal tongue movement and the degree to which the detected tongue movement varies from normal tongue movement.

In some embodiments, the subject's normal tongue movement may be monitored, and a baseline tongue movement profile may be determined and stored for use in detection of sleep disordered breathing events. This baseline tongue movement profile may be determined, for example, upon activation of external unit 120, upon placement of external unit 120 on the skin of a patient relative to implant unit 110, etc. In some embodiments, activation of external unit 120 may include a calibration period, during which processor 144 may be configured to monitor the patient's normal tongue movement. Monitoring the normal tongue movement during the calibration period may include, but is not limited to, a measurement of the range of movement of the tongue during breathing, the speed of movement of the tongue, and the absolute displacement of implant unit 110 from external unit 120.

Subsequent to the calibration period, processor 144 may be configured to monitor movement of the subject's tongue and compare those movements to the tongue movement profile obtained during calibration or to any other suitable baseline tongue movement data. Processor 144 may be configured to detect a sleep disordered breathing event when one or more detected tongue movement characteristics (e.g., absolute displacement, direction of movement, velocity of movement, periodicity of vibratory or oscillatory movements, etc.) as compared to normal tongue movement parameters indicate the existence of a sleep disordered breathing event.

In response to a determination that the tongue movement is representative of sleep disordered breathing, processor 144 may generate a modulation control signal (e.g., a stimulation control signal) to correct the sleep disordered breathing. The modulation control signal may be applied, for example, to primary antenna 150 of external unit 120 and may be configured to interact with secondary antenna 152 of implant unit 110 in order to generate a modulation signal within implant unit 110. This modulation signal may cause activation of one or more nerves associated with the tongue and may lead to contraction of the Genioglossus muscle associated with the tongue. Contraction of the Genioglossus muscle may move the tongue away from the subject's airway to correct or avoid a sleep disordered breathing event.

Processor 144 may further be configured to adjust at least one characteristic of the modulation control signal based on a detected severity of the sleep disordered breathing. The severity of a sleep disordered breathing condition may be determined, for example, based on analysis of movement characteristics (e.g. absolute displacement, direction of movement, velocity of movement, periodicity of vibratory or oscillatory movements, etc.) associated with the tongue. The at least one characteristic of the modulation control signal may include, but is not limited to, voltage amplitude, current amplitude, pulse frequency, pulse duration, or any other suitable characteristic of the modulation control signal.

In response to any of these determined physiologic data, processor 144 may regulate delivery of power to implant unit 110 based on the determined physiologic data. For example, processor 144 may select parameters such as, for example, the power level and/or duration for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. Additionally or alternatively, processor 144 may deliver power to implant unit 110 to initiate a tongue movement, monitor the movement of the tongue, and deliver additional power, for example, a reduced amount of power, if necessary to encourage the tongue to continue moving away from the patient's airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

In some embodiments, processor 144 may select the parameters of a particular modulation control signal or series of modulation control signals based on the severity of a physiological condition. Severity of a detected physiological condition may be defined as a deviation from normal range of the condition, and may be determined by a deviation in, for example, a position of certain tissue or body parts in a subject, a rate of change or direction of change in a position of certain tissue or body parts in a subject, blood oxygen level, blood glucose level, pulse rate, and breathing rate or any other parameter of normal bodily function.

Processor 144 may be configured to select the parameters of a particular modulation control signal or series of modulation control signals based on a function (either continuous or discontinuous) of the severity of the detected physiological condition. In a continuous function, the measured severity may be mapped directly to variations in the power level and/or duration of the modulation control signal based on a transfer function. The transfer function may be universal, predetermined, or may be calibrated for each individual subject. In a discontinuous function, a look-up table may be used to determine an appropriate power level and/or duration of the modulation control signal for severities within certain ranges.

In each case, processor 144 may be configured to use the severity of the physiologic condition to determine an amount of power to be delivered to implant unit 110 in order to modulate nerves associated with the tongue with the appropriate amount of energy. Because the modulation control signal may be received in pulses by secondary antenna 152, the length and frequency of the pulses of the secondary signal generated on secondary antenna 152 may also be varied. Variations in the secondary signal may cause variations in the power level and/or duration of the modulation signal applied to electrodes 158a, 158b.

A method for regulating delivery of power to implant unit 110 may include detecting a severity of a physiologic condition and determining, based on the severity of the physiologic condition, a power level and/or duration of the modulation signal or series of modulation signals. For example, tongue movement may be indicative of a sleep disordered breathing event, and the amount of tongue movement may be indicative of a severity of the sleep disordered breathing event.

In some embodiments, a predetermined movement of implant unit 110 with the tongue muscle 130 may trigger delivery of a modulation signal. The predetermined movement, as used here, refers to a distance threshold, a vibratory amplitude/frequency threshold, or any other suitable threshold parameter.

The power and/or duration of the modulation signal triggered by the movement of implant unit 110 may be dependent on the amount of movement of a subject's tongue. In some embodiment, tongue movement may be indicative of sleep disordered breathing, and the amount of tongue movement may be indicative of a severity of a sleep disordered breathing event. The amount of tongue movement may be determined based on the absolute movement of tongue muscle 130 relative to external unit 120. Alternatively, the amount of tongue movement may be determined by the relative displacement of implant unit 110 and external unit 120. In some embodiments, the amount of tongue movement may also refer to the speed at which the tongue is moving, direction of tongue movement, and vibration of the tongue.

As previously discussed, the degree of coupling between primary antenna 150 associated with external unit 120 and secondary antenna 152 associated with implant unit 110, may be monitored in order to determine an amount of tongue movement. Processor 144 may be configured to monitor the degree of coupling and regulate delivery of power from the external unit 120 to the implant unit 110 based on the determined degree of coupling and/or determined amount of tongue movement. In some embodiment, processor 144 may be configured such that a predetermined movement of the at least one implantable circuit with the tongue triggers delivery of a modulation control signal. Regulation of power delivery in this manner, in turn, may regulate the power level and/or duration of the modulation signal applied to electrodes 158a, 158b.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include at least one processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

In some embodiments, the at least one processor may be associated with monitoring the degree of coupling can provide such physiologic data as whether a patient's tongue is moving or vibrating. In one embodiment, for example, the degree of coupling may indicate physiologic data relating to a distance between external unit 120 and implant unit 110, which processor 144 may use to determine a position of external unit 120 or a relative position of a patient's tongue. The distance between external unit 120 and implant unit 110 may be determined along any suitable and desired vector and/or combination of vectors.

The signals produced by the indicator 145 may permit a user to place external unit 120 at an optimal location in relation to implant unit 110. In one embodiment, indicator 145 may be configured to produce a variable signal (i.e., two or more signals) when external unit 120 is within a predetermined distance range of implant unit 110, such that the variable signal may be configured to reach a maximum output when external unit 120 is at an optimal distance from implant unit 110. For example, if the indicator signal is audible, it may be configured to change pitch as external unit 120 is moved closer to implant unit 110, thereby reaching the highest, or alternatively, the lowest pitch, when external unit 120 is at an optimal location. Further examples of indicator signals may include, but are not limited to, beeps that change frequencies, a light changing colors and/or getting brighter or dimmer, a tactile output (e.g., vibration) that increases or decreases in strength, or an electrical stimulating signal that increases or decreases in strength. Of course, these signals are described as examples only. There are nearly limitless forms of audible, visual, tactile, or other signals that can be configured to convey a degree of coupling between external unit 120 and internal unit 110.

In addition, or alternatively, the indicator 145 may be configured to transmit electrical signals directly to implant unit 110 in response to a determined degree of coupling. For example, once the determined degree of coupling reaches a suitable level or exceeds a predetermined threshold, for example, the indicator 145 may cause a modulation control signal to be issued that causes modulation of a nerve in the subject's body. This modulation may be felt by the subject and may serve as an indication that external unit is properly positioned with respect to implant unit 110.

The indicator 145 may further be configured to produce a signal when external unit 120 is within a predetermined distance range of implant unit 110 or when a degree of coupling between external unit 120 and implant unit 110 exceeds a predetermined threshold. The indicator 145 may further be configured to provide a signal when external unit 120 is not within a predetermined distance range of implant unit 110 or when a determined degree of coupling between the two units falls below a predetermined threshold. For example, indicator 145 may be configured to produce at least two signals: a first signal when external unit 120 is within a predetermined distance range of implant unit 110 or when a determined coupling level exceeds a predetermined level and a second, different signal when external unit 120 is not within a predetermined distance range of implant unit 110 or when the determined coupling level does not exceed the predetermined level.

Implant unit 110 may be configured to deliver at power in at least a first power mode and a second power mode. Power delivery in the first power mode and the second power mode may be configured in any suitable manner in order to provide a desired response or performance characteristic. For example, in some embodiments, the level of power delivered in the first power mode and the second mode may be different. For example, the first power mode may be associated with a power level that is less than a power level associated with the second power mode. Any suitable power delivery scheme using at least the first power mode and second power mode may also be employed. For example, during a therapy period, power delivery in the first mode may be associated with a desired duty cycle such that power delivery in the first power mode occurs over a total time that is greater than about 50% of the therapy period (e.g., while a subject is asleep). In some embodiments, however, the total time of power delivery in the first power mode may be greater than about 90% of the therapy period. The total time of power delivery in the first power mode may also be greater than about 95% of the therapy period.

Power may be supplied to implant unit 110 in any suitable form. In some embodiments, the at least one processor may be configured to cause power to be delivered to implant unit 110 via an alternating current signal or via a direct current signal. In embodiments where power is supplied via an alternating current signal, implant unit 110 may include conversion circuitry for converting the alternating current signal received, for example, by secondary antenna 152 to a direct current signal to be applied, for example to electrodes 158 a, b.

The power levels associated with each of the first and second power modes may be selected to provide a desired response or performance characteristic of implant unit 110 and/or external unit 120. For example, in some embodiments, the power delivered to implant unit 110 during the first power mode may be provided via a sub-stimulation or sub-modulation control signal applied to primary antenna 150. As noted above, such sub-modulation control signals may include an amplitude and/or duration that result in a sub-modulation signal at electrodes 158a, 158b (e.g., a signal that produces little or no nerve modulation). While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

The sub-modulation control signal in the first power mode may be applied in any suitable manner for achieving a desired operational characteristic of either implant unit 110 or external unit 120 or for determining various parameters associated with implant unit 110 or external unit 120. For example, a sub-modulation control signal may be useful in making impedance measurements, e.g., using standard RF coupling techniques to detect the impedance between primary antenna 150 and secondary antenna 152. In a first power mode, the energy sent may include a low voltage AC signal (e.g., a sub-modulation control signal), to detect movement of the implant through coupling. As a sub-modulation control signal, this low power AC signal may provide insufficient power to activate the stimulation circuit. Diodes, e.g. diode 156 in FIG. 6, may be used to control whether the low voltage AC signal activates the stimulator. The low power AC signal, or sub-modulation control signal, may be constantly provided in order to continuously or periodically detect location and motion of implant unit 110 over a period of time. This signal, however, may be provided at a level below that needed to activate diodes in the circuit of FIG. 6 (e.g., diode 156). With no activation of the diodes, little or no current is passed to electrodes 158 a, b.

The sub-modulation control signal may also be useful for monitoring asymmetric non-linearities generated through activation of diode 156. The non-linear diode 156 rectifies the signal appearing on secondary antenna 152, which may result in the production of harmonics that may be detected as one or more signal components induced on primary antenna 150. These harmonics may be asymmetric in view of the half wave rectification provided by diode 156. While the sub-modulation control signal may have an amplitude sufficient to cause forward biasing of diode 156, nerve modulation may be avoided by applying sub-modulation control signal to primary antenna 150 using pulse durations that are sufficiently short to avoid nerve modulation.

The sub-modulation control signal may also be useful in monitoring symmetric non linearities generated through activation of both diode 156 and the Zener diodes 154 (FIG. 6). In such embodiments, the transmitted voltage associated with the sub-modulation control signal may be high enough to activate both diode 156 and Zener diodes 154 such that symmetric, non-linear harmonics are generated. The pulse duration of the sub-modulation control signal, however, may be short enough to avoid nerve modulation. and the zener diodes earlier in the circuit.

Monitoring the impedance, onset of non-linearities, or transitions from asymmetric to symmetric non-linearities may provide information regarding various aspects of implant unit 110. For example, such information may enable determination of the position of implant unit 110 with respect to external unit 120, relative direction of movement, velocity of movement, etc.

During the second power mode, the at least one processor may cause a second alternating current signal (e.g., a modulation control signal) to be applied to primary antenna 150 in order to supply power to implant unit 110. A signal induced on secondary antenna 152 in response to the modulation control signal may be supplied to the electrodes for generating an electromagnetic field. In some embodiments, the signal on secondary antenna 152 may be converted to DC for application to electrodes 158a, b by either active or passive circuit components or by any other suitable method. The modulation control signal may be associated with a power level higher than the sub-modulation control signal and/or a pulse length longer than the sub-modulation control signal. While the sub-modulation control signal may be useful for monitoring various characteristics associated with implant unit 110, the modulation control signal may be associated with a power level and/or pulse duration sufficient to cause modulation of at least one nerve in the body of the subject.

In some embodiments, the pulse length of the sub-modulation control signal may be less than 50 microseconds or less than 500 nanoseconds. The pulse length of the modulation control signal may be greater than 50 microseconds.

Either of the sub-modulation control signal or the modulation control signal may include any signal which may cause power to be supplied to the implant. In some embodiments, these signals may include electromagnetic signals (e.g. microwave, infrared, radio-frequency (RF), etc.). These signals may include any suitable waveforms (e.g. sinusoidal, sawtooth wave, square wave, triangle wave) and may include any suitable amplitude or duration which may achieve the desired results.

The first power mode may be implemented in any manner which may deliver less power than the power in the second power mode. In some embodiments, the first power mode may not provide enough power to activate the implant unit. For example, the first alternating current signal may be supplied at a lower voltage during the first power mode than the alternating current signal applied during the second power mode.

In the second power mode, the level of power delivered may be any level greater than the level of power in the first mode. In some embodiments, the power level in the second mode is sufficient to activate the implant. The level of power transmitted in the second mode may be sufficient to allow implant unit 110 to cause neural modulation through the electrodes associated with the implant circuit.

As used herein, references to an amount of power delivered may refer both to an instantaneous rate of energy transfer and a rate of energy transfer over a specific period of time. For example, at a constant current, increasing the voltage of a signal will increase the instantaneous rate of energy transfer of that signal, thereby increasing the amount of power delivered. In an embodiment utilizing power delivery in direct current pulses, an amount of power delivered may be increased even if voltage and current are held constant. Consider for example, power delivered in a series of direct current pulses over a specified time period. Over the specified time period, direct current pulses having a greater length will deliver a greater amount of power than a series of direct current pulses having a shorter length, even if the instantaneous rate of energy transfer during each pulse is the same. That is, the amount of power delivered may be measured as a function of energy transferred over any appropriate length of time.

Physiologically, different methods of altering an amount of power delivered may be used in order to create a signal adapted to modulate (or not modulate) a nerve. For example, delivering less power to modulation electrodes 158*a*, 158*b* via a signal with lower current may result in the generation of an electric field too weak to exceed the membrane potential threshold of neural ion channels, thus resulting in no modulation. Increasing the power via an increased current may serve to induce an electric field sufficient to cause modulation. Power delivery with an increased current, therefore, may be an example of delivering an amount of current sufficient to modulate a nerve. In another example, delivering less power to modulation electrodes 158*a*, 158*b* by delivering shorter pulses without reducing the current may result in the generation of a short lived electric field. Such a short lived electric field may not permit the ion channels in the field enough time to activate and pump sufficient ions across the plasma membrane in order to propagate an action potential to neighboring ion channels. That is, the energy is transferred to the ion channel while the electric field is being generated may be insufficient to modulate the nerve. Increasing the power delivery in such an embodiment by increasing the pulse lengths (such that the pulses facilitate an electric field of sufficient duration to induce the propagation of an action potential) may constitute one example of power delivery in pulse lengths sufficient to cause neural modulation.

In some embodiments, the at least one processor may be in electrical communication with primary antenna 150 and configured to be located external to a subject. The at least one processor may also be configured to receive a condition signal from an implantable device. In some embodiments, the condition signal may be indicative of a precursor to sleep disordered breathing. In response to the received condition signal, the at least one processor may cause transmission of a primary signal from the primary antenna to the implantable device. In some embodiments, the primary signal may be used to stimulate at least one nerve (for example, a hypoglossal nerve) in response to a detected precursor to sleep disordered breathing. The primary antenna and the at least one processor may also be associated with an external unit, for example external unit 120.

The condition signal received from the implantable device (which may be configured to be implanted, for example, in the body of a subject and proximate to the subject's tongue) may include any signal or signal component indicative of at least one condition associated with the subject. In some embodiments, for example, the condition may indicate whether a portion of the subject's body (e.g., the tongue) has moved, a direction of movement, a rate of change of movement, temperature, blood pressure, etc. The condition signal may include any form of signal suitable for conveying information associated with at least some aspect of the subject. In some embodiments, the condition signal may include an electromagnetic signal (e.g. microwave, infrared, radio-frequency (RF), etc.) having any desired waveform (e.g. sinusoidal, square wave, triangle wave, etc.). The condition signal may include any suitable amplitude or duration for transferring information about the subject. In some embodiments, the control signal may include a signal component arising on primary antenna 150 as a result of coupling with secondary antenna 152 on implant unit 110. For example, in some embodiments, the condition signal may include a primary coupled signal component on primary antenna 150. This primary coupled signal component may be induced on primary antenna 150 through coupling between primary antenna 150 of external unit 120 and secondary antenna 152 on implant unit 110. In other embodiments, the control signal may include signals transmitted to primary antenna 150 via one or more active transmitters in implant unit 110.

In some embodiments, the condition signal may be indicative of movement of a subject's tongue. For example, movement of the tongue may cause relative motion between primary antenna 150 and secondary antenna 152, and this relative motion may result in variation of a degree of coupling between primary antenna 150 and secondary antenna 152. In some embodiments, the condition signal may be indicative of the degree of coupling between the primary antenna 150 and secondary antenna 152 associated with the implantable device. By monitoring the degree of coupling between primary antenna 150 and secondary antenna 152, for example, by monitoring signals or signal components present on primary antenna 150, relative movement between primary antenna 150 and secondary antenna 152 (which may indicate relative movement between implantable device 110 and external unit 120, with which primary antenna 150 and the at least one processor are associated), and, therefore, movement of the subject's tongue, may be detected. In some embodiments, the condition signal may be indicative of the subject's tongue over a predetermined distance. Generally, however, the condition signal may indicate any condition at least partially upon which a primary signal may be sent.

As noted, the at least one processor may cause a response based on the condition signal. For example, in some embodiments, the at least one processor may be configured to cause the generation of a primary signal intended to control at least one aspect of implant unit 110. The primary signal may include a modulation control signal applied to primary antenna 150 such that a resulting secondary signal on secondary antenna 152 will provide a modulation signal at implant electrodes 158*a* and 158*b*.

In some embodiments, the processor may be configured to detect a sleep disordered breathing event based on the condition signal and send a primary signal in response to the detected sleep disordered breathing event. In some embodiments, the sleep disordered breathing event may be a precursor of sleep apnea or of sleep apnea-related airway blockage, and the primary signal may be predetermined to activate neuromuscular tissue within the tongue. Such activation may cause movement of the subject's tongue, for example, in a direction away from the posterior pharyngeal wall. In some embodiments, transmission of the primary signal from primary antenna 150 to the implantable device 110 may occur prior to the sleep apnea airway blockage.

The primary signal may include any suitable characteristics for causing a desired response in implant unit 110. For example, the primary signal may have any suitable amplitude, duration, pulse width, duty cycle, or waveform (e.g. a sinusoidal signal, square wave, triangle wave, etc.) for causing a desired effect on implant unit 110 (e.g., modulation of nerve tissue, for example a hypoglossal nerve, in the vicinity of implant unit 110, etc.).

In some embodiments, the desired effect may be achieved by supplying an electrical signal to at least one pair of electrodes, for example electrodes 158*a* and 158*b*, in the implantable device. The electrodes may be configured to generate an electromagnetic field to stimulate the at least one nerve. In some embodiments, one electrode of each pair may function as an anode (i.e. a positive electrode), and the other electrode of the pair may function as a cathode (i.e. a negative electrode). Implant unit 110 may be configured in a manner that promotes achievement of the desired effect. For example, in at least some embodiments, implant unit 110 may be configured such that when implant unit 110 is implanted into a subject, the electrodes of implant 110 will be oriented such that an electromagnetic field generated from the electrodes extends in an elongated direction of the at least one nerve to be stimulated. In some embodiments, the field is created, for example, by forming a direct current (DC) pulse and providing it to one or more pairs of electrodes.

Electromagnetic fields from the electrodes on implant unit 110 may be generated in any suitable manner. In some embodiments, the at least one processor may cause generation of a primary signal on primary antenna 150, which, in turn, may cause a responsive signal to appear on secondary antenna 152 through coupling. As discussed above, circuitry in implant unit 110 may respond to the presence of a signal on the secondary antenna and cause a signal to be applied to electrodes 158*a* and 158*b*. This applied signal at the elecrodes may creates the electromagnetic field for stimulating neuromuscular tissue in the body of a subject.

In some embodiments, the at least one processor may be associated with the housing of external unit 120 and may be configured to communicate with a circuit implanted in the subject. The at least one processor may also be configured to receive a physiological signal from the subject via the implanted circuit. In response to the received physiological signal, the at least one processor may send a control signal, such as a closed loop control signal, to the implanted circuit. In some embodiments, the control signal may be predetermined to activate neuromuscular tissue within the tongue. Activating neuromuscular tissue may include, for example, causing muscular contractions and initiating a nerve action potential.

The physiological signal received from the implant unit may include any signal or signal component indicative of at least one physiological characteristic associated with the subject. In some embodiments, for example, the physiological characteristic may indicate whether a portion of the subject's body (e.g., the tongue) has moved, a direction of movement, a rate of change of movement, temperature, blood pressure, etc. The physiological signal may include any form of signal suitable for conveying information associated with at least some aspect of the subject. In some embodiments, the physiological signal may include an electromagnetic signal (e.g. microwave, infrared, radio-frequency (RF), etc.) having any desired waveform (e.g. sinusoidal, square wave, triangle wave, etc.). In some embodiments, the physiological signal may include any suitable amplitude or duration for transferring information about the subject.

In some embodiments, the physiological signal may include a primary coupled signal component on primary antenna 150. This primary coupled signal component may be induced on primary antenna 150 through coupling between primary antenna 150 of external unit 120 and secondary antenna 152 on implant unit 110.

In some embodiments, the physiological signal may include at least one aspect indicative of a movement of the subject's tongue. For example, movement of the tongue may cause relative motion between primary antenna 150 and secondary antenna 152, and this relative motion may result in variation of a degree of coupling between primary antenna 150 and secondary antenna 152. By monitoring the degree of coupling between primary antenna 150 and secondary antenna 152, for example, by monitoring signals or signal components present on primary antenna 150, relative motion between primary antenna 150 and secondary antenna 152 and, therefore, movement of the subject's tongue, may be detected.

As noted, in response to a received physiological signal, the at least one processor may cause a response based on the physiological signal. For example, in some embodiments, the at least one processor may be configured to cause the generation of a control signal (e.g. a closed loop control signal) intended to control at least one aspect of implant unit 110. The control signal may include a modulation control signal applied to primary antenna 150 such that a resulting secondary signal on secondary antenna 152 will provide a modulation signal at implant electrodes 158*a* and 158*b*.

In some embodiments, the processor may be configured to detect a sleep disordered breathing event based on the physiological signal and send the closed loop control signal in response to the detected sleep disordered breathing event. In some embodiments, the sleep disordered breathing event may be a precursor of sleep apnea, and the control signal may be predetermined to activate neuromuscular tissue within the tongue and may cause movement of the subject's tongue, for example, in a direction away from the posterior pharyngeal wall. The at least one processor may be further configured to determine a severity of the sleep disordered breathing event based on the physiological signal and vary a power level or duration of the control signal based on the determined severity of the sleep disordered breathing event. The severity of the event may be determined, for example, based on a determination of the relative movement between primary antenna 150 and secondary antenna 152 (e.g., an amplitude of movement, a rate of movement, a direction of movement, etc.). In some embodiments, a control signal may be sent if the relative movement exceeds a certain threshold.

A control signal may include any signal having suitable characteristics for causing a desired response in implant unit 110. For example, a control signal may have any suitable amplitude, duration, pulse width, duty cycle, or waveform (e.g. a sinusoidal signal, square wave, triangle wave, etc.) for causing a desired effect on implant unit 110 (e.g., modulation of nerve tissue in the vicinity of implant unit 110, etc.). A control signal may be generated and sent (e.g., to implant unit 110) within any desired response time relative to receipt of a physiological signal. In some embodiments, the response time may be set at 1 second, 500 milliseconds, 200 milliseconds, 100 milliseconds, 50 milliseconds, 20 milliseconds, 5 milliseconds, 1 millisecond, or any other time greater than 0 seconds and less than about 2 seconds. The control signal may be closed loop. As used herein, the term closed loop control signal may refer to any signal at least partially responsive to another signal, such as a control signal sent in response to a physiological signal. Or it may include any feedback response.

Based on the physiological signal, the processor may determine a quantity of energy to be sent via the closed loop control signal to implant unit 110. The amount of energy to be sent may be determined and/or varied based on any relevant factor including, for example, the time of day, a relevant biological factor of the subject (blood pressure, pulse, level of brain activity, etc.), the severity of the detected event, other characteristics associated with the detected event, or on any combination of factors. As noted, in embodiments where the physiological signal indicates a sleep disordered breathing event, the processor may be configured to determine a severity of the sleep disordered breathing event based on the physiological signal. In such embodiments, the processor may also determine an amount of energy to be provided to implant unit 110 as a response to the detected sleep disordered breathing event and in view of the determined severity of the event. The determined amount of energy may be transferred to implant unit 110 over any suitable time duration and at any suitable power level. In some embodiments, the power level and/or the duration of the control signal may be varied, and such variation may be dependent on the determined severity of the sleep disordered breathing event.

The power level and/or duration of the control signal may also be determined based on other factors. For example, the processor may vary a power level or duration associated with the control signal based on the efficiency of energy transfer between external unit 120 and implant unit 110. The processor may have access to such information through pre-programming, lookup tables, information stored in memory, etc. Additionally or alternatively, the processor may be configured to determine the efficiency of energy transfer, e.g., by monitoring the primary coupled signal component present on primary antenna 150, or by any other suitable method.

The processor may also vary the power level or duration of the control signal based on the efficacy of implant unit 110 (e.g., the implant unit's ability to produce a desired effect in response to the control signal). For example, the processor may determine that a certain implant unit 110 requires a certain amount of energy, a control signal of at least a certain power level and/or signal duration, etc., in order to produce a desired response (e.g., a modulation signal having an amplitude/magnitude of at least a desired level, etc). Such a determination can be based on feedback received from implant unit 110 or may be determined based on lookup tables, information stored in memory, etc. In some embodiments, the power level or duration of the control signal may be determined based on a known or feedback-determined efficacy threshold (e.g., an upper threshold at or above which a desired response may be achieved) associated with implant unit 110.

Figure 12:
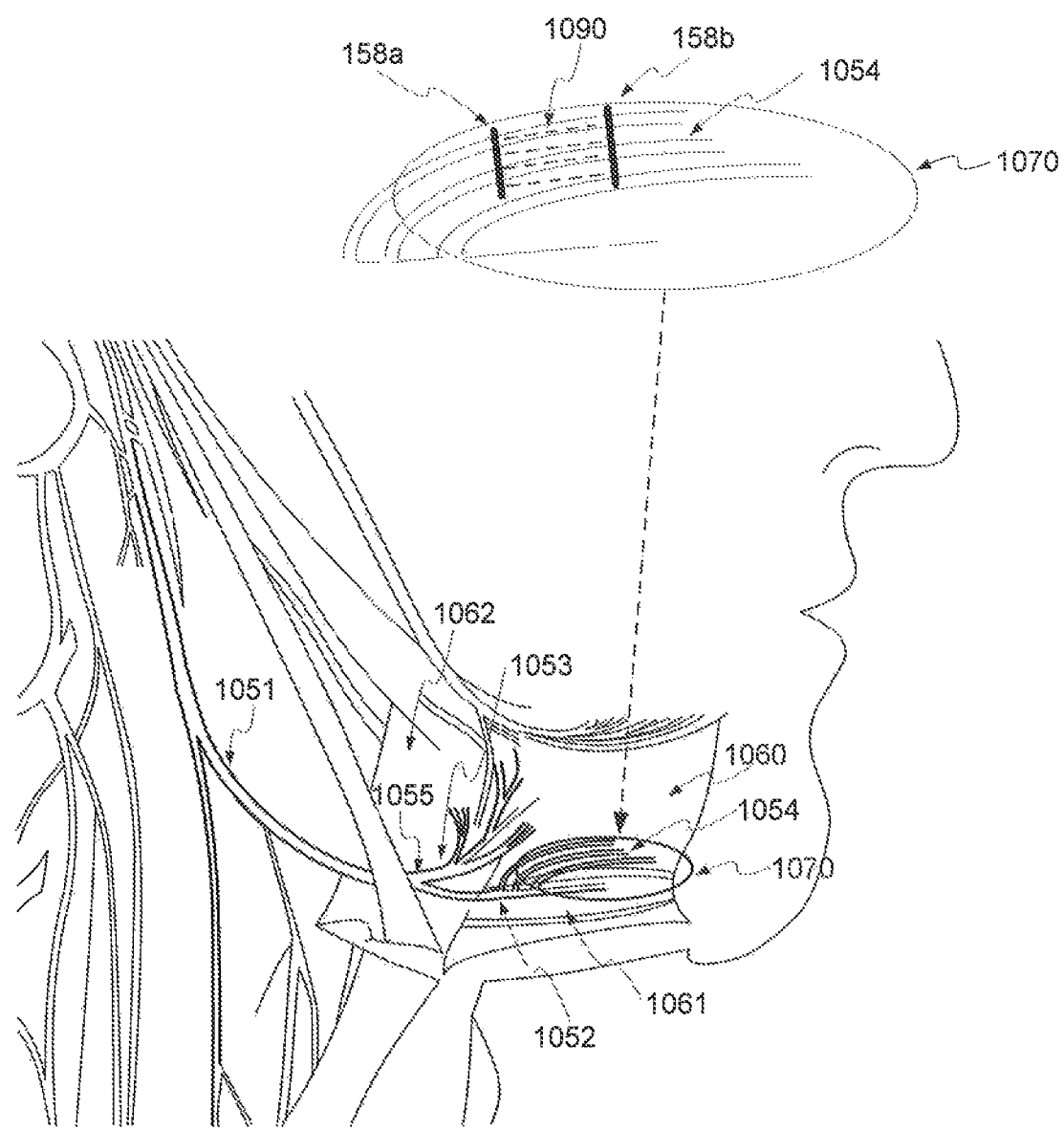
FIG. 12 depicts anatomy of the tongue and associated muscles and nerves.
Figure 13:
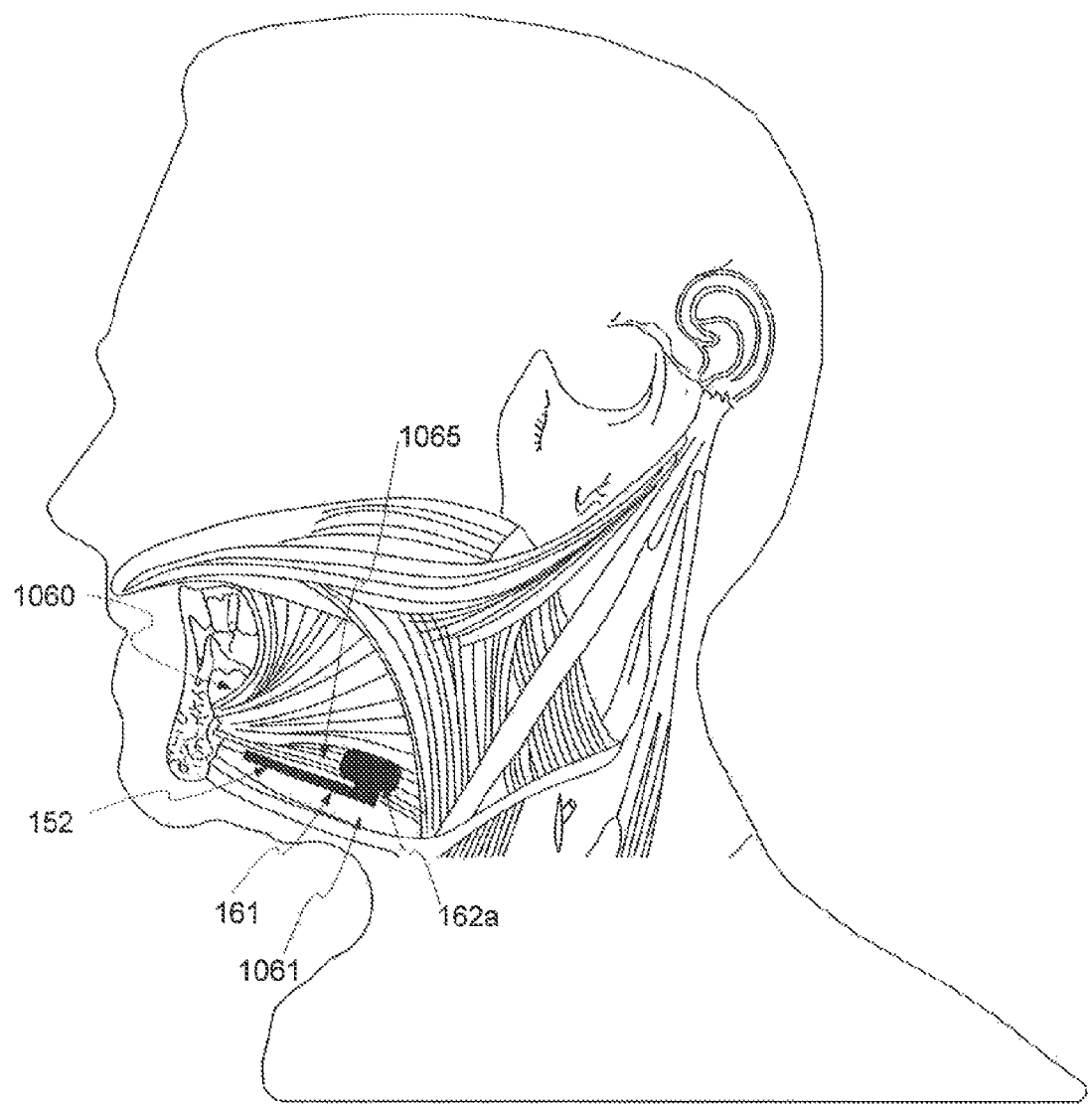
FIG. 13 depicts an exemplary implant location for the treatment of sleep apnea.
Figure 14:
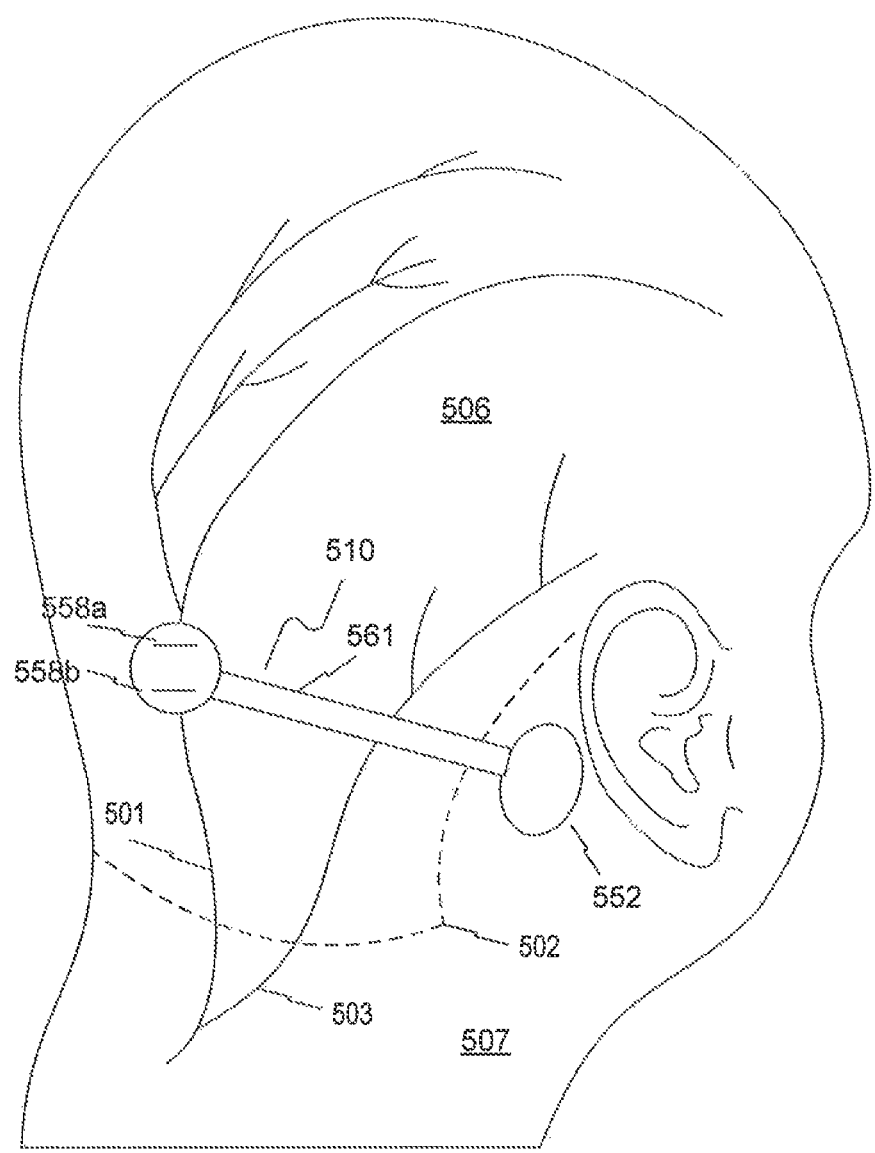
FIG. 14 depicts an exemplary implant location for the treatment of head pain.
Figure 15:
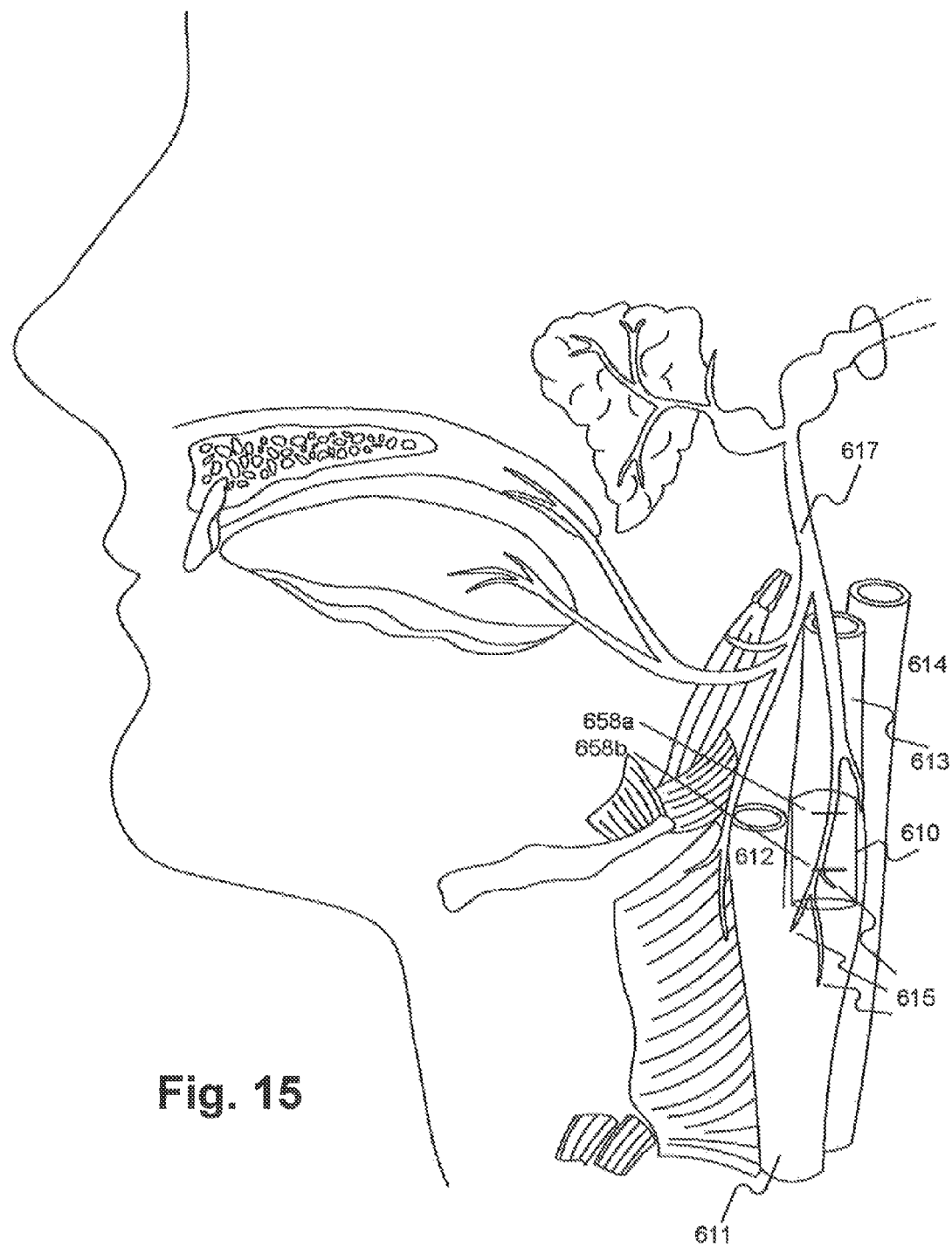
FIG. 15 depicts an exemplary plant location for the treatment of hypertension.
Figure 16:
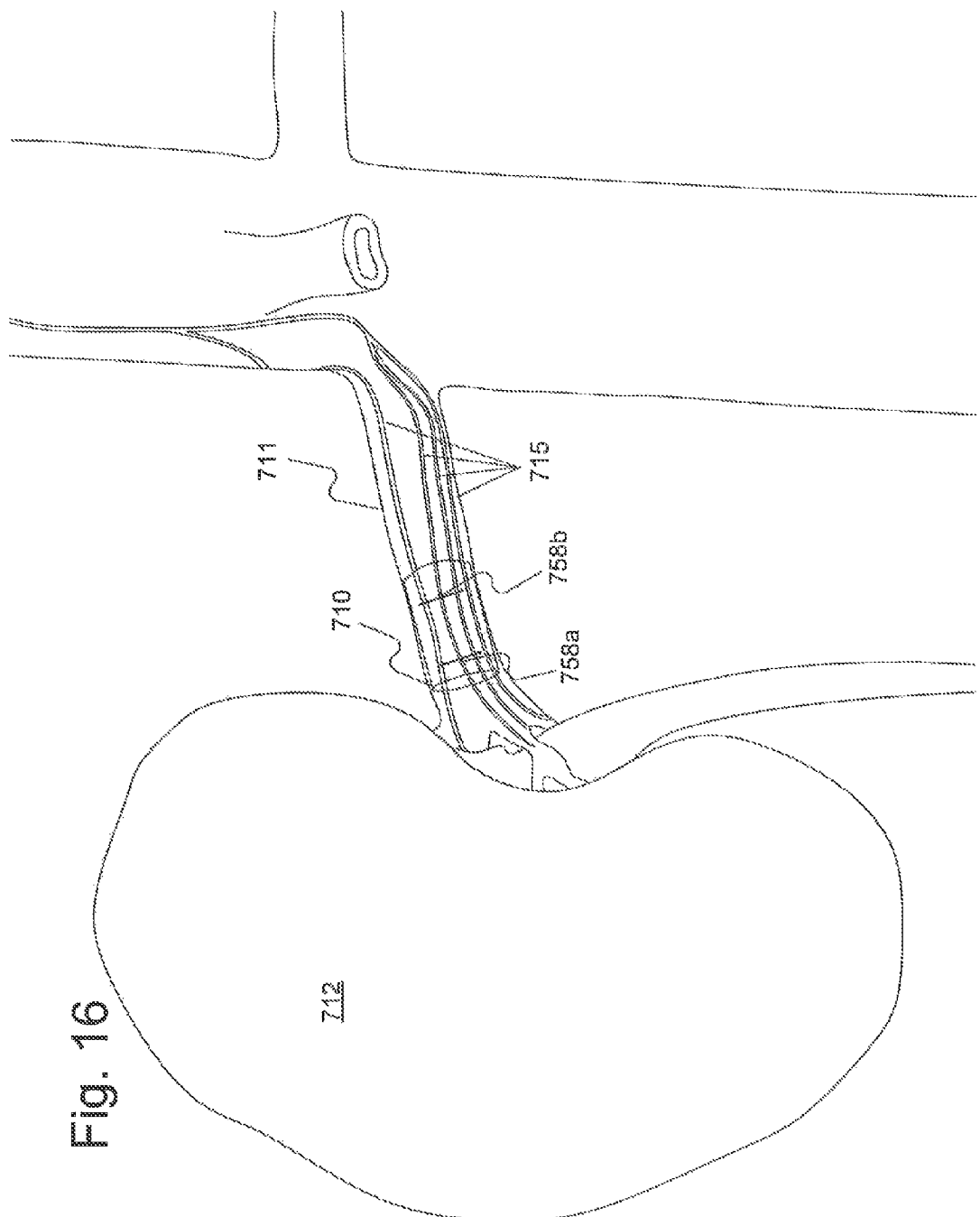
FIG. 16 depicts an exemplary plant location for the treatment of hypertension.

In some embodiments, implant unit 110 may be structurally configured to facilitate implantation in a location so as to increase the efficacy of modulation provided. For example, FIGS. 12 and 13 illustrate the anatomy of neck and tongue, and depict implantation locations suitable for neuromodulation treatment of OSA. FIG. 14 illustrates an exemplary implant unit 110 structurally configured for the treatment of head pain. FIGS. 15 and 16 illustrate exemplary implant units 110 structurally configured for the treatment of hypertension.

FIG. 12 depicts an implantation location in the vicinity of a genioglossus muscle 1060 that may be accessed through derma on an underside of a subject's chin. FIG. 12 depicts hypoglossal nerve (i.e. cranial nerve XII). The hypoglossal nerve 1051, through its lateral branch 1053 and medial branch 1052, innervates the muscles of the tongue and other glossal muscles, including the genioglossus 1060, the hyoglossus 1062, mylohyoid (not shown) and the geniohyoid 1061 muscles. The mylohyoid muscle, not pictured in FIG. 12, forms the floor of the oral cavity, and wraps around the sides of the genioglossus muscle 1060 and the geniohyoid 1061 muscles. The horizontal compartment of the genioglossus 1060 is mainly innervated by the medial terminal fibers 1054 of the medial branch 1052, which diverges from the lateral branch 1053 at terminal bifurcation 1055. The distal portion of medial branch 1052 then variegates into the medial terminal fibers 1054. Contraction of the horizontal compartment of the genioglossus muscle 1060 may serve to open or maintain a subject's airway. Contraction of other glossal muscles may assist in other functions, such as swallowing, articulation, and opening or closing the airway. Because the hypoglossal nerve 1051 innervates several glossal muscles, it may be advantageous, for OSA treatment, to confine modulation of the hypoglossal nerve 1051 to the medial branch 1052 or even the medial terminal fibers 1054 of the hypoglossal nerve 1051. In this way, the genioglossus muscle, most responsible for tongue movement and airway maintenance, may be selectively targeted for contraction inducing neuromodulation. Alternatively, the horizontal compartment of the genioglossus muscle may be selectively targeted. The medial terminal fibers 1054 may, however, be difficult to affect with neuromodulation, as they are located within the fibers of the genioglossus muscle 1061. Embodiments of the present invention facilitate modulation the medial terminal fibers 1054, as discussed further below.

In some embodiments, implant unit 110, including at least one pair of modulation electrodes, e.g. electrodes 158a, 158b, and at least one circuit may be configured for implantation through derma (i.e. skin) on an underside of a subject's chin. When implanted through derma on an underside of a subject's chin, for example, into a sub-mandibular region, an implant unit 110 may be located proximate to medial terminal fibers 1054 of the medial branch 1052 of a subject's hypoglossal nerve 1051. An exemplary implant location 1070 is depicted in FIG. 12.

In some embodiments, implant unit 110 may be configured such that the electrodes 158a, 158b cause modulation of at least a portion of the subject's hypoglossal nerve through application of an electric field to a section of the hypoglossal nerve 1051 distal of a terminal bifurcation 1055 to lateral and medial branches 1053, 1052 of the hypoglossal nerve 1051. In additional or alternative embodiments, implant unit 110 may be located such that an electric field extending from the modulation electrodes 158a, 158b can modulate one or more of the medial terminal fibers 1054 of the medial branch 1052 of the hypoglossal nerve 1051. Thus, the medial branch 1053 or the medial terminal fibers 1054 may be modulated so as to cause a contraction of the genioglossus muscle 1060, which may be sufficient to either open or maintain a patient's airway. When implant unit 110 is located proximate to the medial terminal fibers 1054, the electric field may be configured so as to cause substantially no modulation of the lateral branch of the subject's hypoglossal nerve 1051. This may have the advantage of providing selective modulation targeting of the genioglossus muscle 1060.

As noted above, it may be difficult to modulate the medial terminal fibers 1054 of the hypoglossal nerve 1051 because of their location within the genioglossus muscle 1060. Implant unit 110 may be configured for location on a surface of the genioglossus muscle 1060. Electrodes 158a, 158b, of implant unit 110 may be configured to generate a parallel electric field 1090, sufficient to cause modulation of the medial terminal branches 1054 even when electrodes 158a, 158b are not in contact with the fibers of the nerve. That is, the anodes and the cathodes of the implant may be configured such that, when energized via a circuit associated with the implant 110 and electrodes 158a, 158b, the electric field 1090 extending between electrodes 158a, 158b may be in the form of a series of substantially parallel arcs extending through and into the muscle tissue on which the implant is located. A pair of parallel line electrodes or two series of circular electrodes may be suitable configurations for producing the appropriate parallel electric field lines. Thus, when suitably implanted, the electrodes of implant unit 110 may modulate a nerve in a contactless fashion, through the generation of parallel electric field lines.

Furthermore, the efficacy of modulation may be increased by an electrode configuration suitable for generating parallel electric field lines that run partially or substantially parallel to nerve fibers to be modulated. In some embodiments, the current induced by parallel electric field lines may have a greater modulation effect on a nerve fiber if the electric field lines 1090 and the nerve fibers to be modulated are partially or substantially parallel. The inset illustration of FIG. 12 depicts electrodes 158a and 158b generating electric field lines 1090 (shown as dashed lines) substantially parallel to medial terminal fibers 1054.

In order to facilitate the modulation of the medial terminal fibers 1054, implant unit 110 may be designed or configured to ensure the appropriate location of electrodes when implanted. An exemplary implantation is depicted in FIG. 13.

For example, a flexible carrier 161 of the implant may be configured such that at least a portion of a flexible carrier 161 of the implant is located at a position between the genioglossus muscle 1060 and the geniohyoid muscle 1061. Flexible carrier 161 may be further configured to permit at least one pair of electrodes arranged on flexible carrier 161 to lie between the genioglossus muscle 1060 and the mylohyoid muscle. Either or both of the extensions 162a and 162b of elongate arm 161 may be configured adapt to a contour of the genioglossus muscle. Either or both of the extensions 162a and 162b of elongate arm 161 may be configured adapt to a contour of the genioglossus muscle. Either or both of the extensions 162a and 162b of elongate arm 161 may be configured to extend away from the underside of the subject's chin along a contour of the genioglossus muscle 1060. Either or both of extension arms 162a, 162b may be configured to wrap around the genioglossus muscle when an antenna 152 is located between the genioglossus 1060 and geniohyoid muscle 1061. In such a configuration, antenna 152 may be located in a plane substantially parallel with a plane defined by the underside of a subject's chin, as shown in FIG. 13.

Flexible carrier 161 may be configured such that the at least one pair of spaced-apart electrodes can be located in a space between the subject's genioglossus muscle and an adjacent muscle. Flexible carrier 161 may be configured such that at least one pair of modulation electrodes 158a, 158b is configured for implantation adjacent to a horizontal compartment 1065 of the genioglossus muscle 1060. The horizontal compartment 1065 of the genioglossus 1060 is depicted in FIG. 13 and is the portion of the muscle in which the muscle fibers run in a substantially horizontal, rather than vertical, oblique, or transverse direction. At this location, the hypoglossal nerve fibers run between and in parallel to the genioglossus muscle fibers. In such a location, implant unit 110 may be configured such that the modulation electrodes generate an electric field substantially parallel to the direction of the muscle fibers, and thus, the medial terminal fibers 1054 of the hypoglossal nerve in the horizontal compartment.

FIG. 14 depicts an exemplary implant location for the treatment of head pain. As illustrated in FIG. 14, implant unit 510 includes an elongated carrier 561, secondary antenna 552, and modulation electrodes 558a, 558b. Implant unit 510 may also include any elements, such as circuitry, electrical components, materials, and any other features described previously with respect to implant unit 110. Implant 510 may be sized and configured such that it may be implanted with an end having secondary antenna 552 located beneath the skin in a substantially hairless region 507 of a subject. Elongated flexible carrier 561 may extend from this location, across a hairline 502 of the subject, to a location beneath the skin in a substantially haired region 506 of the subject in a vicinity of an occipital or other nerve that may be modulated to control or reduce head pain, such as a greater occipital nerve 501 or a lesser occipital nerve 503. As used herein, the term "substantially haired region" includes areas of a subject's head located on a side of the hairline where the scalp hair is located on a typical subject. Thus, a bald person may still have a "substantially haired region" on the side of the hairline on which hair typically grows. As used herein, the term "substantially hairless region" includes areas of a subject's head located on a side of the hairline where the scalp hair is not located on a typical subject. A "substantially hairless region," as used herein, is not required to be completely hairless, as almost all skin surfaces have some hair growth. As illustrated in FIG. 14, a substantially haired region 506 is separated from a substantially hairless region 507 by a hairline 502.

As described above, implant 510 may extend across the hairline 502 to a location in the vicinity of an occipital nerve. In FIG. 14, implant 510 extends across the hairline 502 to a location in the vicinity of greater occipital nerve 501. Furthermore, implant 510 may be configured for implantation such that electrodes 558a and 558b are spaced from each other along a longitudinal direction of an occipital nerve, such as the greater occipital nerve 501 shown in FIG. 14. Such a configuration permits electrodes 558a and 558b to facilitate an electrical field that extends in the longitudinal direction of the occipital nerve. In turn, the facilitated electrical field may be utilized to modulate greater occipital nerve 501, for example to block pain signals, as previously described.

The size and configuration of implant 510 illustrated in FIG. 14 may permit secondary antenna 552 to be located beneath the skin in a location where an external unit 520 (not illustrated), may be easily affixed to the skin, due to the lack of hair. External unit 520 may include any elements, such as circuitry, processors, batteries, antennas, electrical components, materials, and any other features described previously with respect to external unit 120. External unit 520 may be configured to communicate with implant 510 via secondary antenna 552 to deliver power and control signals, as described above with respect to external unit 120. Elongated carrier 561 may be flexible, and may permit modulation electrodes 558a and 558b to be located beneath the skin in a location suitable for modulating an occipital or other nerve for controlling head pain.

FIG. 15 depicts an exemplary implant location for the treatment of hypertension. As illustrated in FIG. 15, implant unit 610 may be configured for location or implantation inside a blood vessel. Such a configuration may include, for example, a flexible tubular carrier. Implant unit 610 may also include any elements, such as circuitry, electrical components, materials, and any other features described previously with respect to implant unit 110. Implant unit 610 may include modulation electrodes 658a, 658b configured to facilitate an electric field including field lines extending in the longitudinal direction of the blood vessel. For example, as illustrated in FIG. 13, implant unit 610 may be implanted in a carotid artery 611. Implant unit 610 may be located within carotid artery 611 in a location in the vicinity of carotid baroreceptors 615, at a location near the branching of the internal carotid artery 613 and the external carotid artery 612. As described previously, carotid baroreceptors 615 aid in the regulation of the blood pressure of a subject. Thus, implant unit 610, located within carotid artery 611 in the vicinity of carotid baroreceptors 615 may facilitate an electric field configured to modulate carotid baroreceptors 615, and, thus, affect the blood pressure of a subject. Affecting the blood pressure of a subject may include reducing, increasing, controlling, regulating, and influencing the blood pressure of a subject. The illustrated location is exemplary only, and implant unit 610 may be configured in alternate ways. For example, implant unit 610 may be configured for implantation in jugular vein 614 of the subject, in a location from which modulation of carotid baroreceptors 615 may be accomplished. Furthermore, implant unit 610 may be configured for implantation in a blood vessel, such as carotid artery 611 or jugular vein 614, in a location suitable for modulation of glossopharyngeal nerve 615. As described above, glossopharyngeal nerve 615 innervates carotid baroreceptors 615. Thus, glossopharyngeal nerve 615 may be directly modulated to affect blood pressure of a subject. Glossopharyngeal nerve 615 may also be modulated by an implant unit 610 located in a sub-cutaneously, in a non intravascular location.

FIG. 16 depicts another exemplary implant location for the treatment of hypertension. As illustrated in FIG. 16, implant unit 710 may be configured for location or implantation inside a blood vessel. Such a configuration may include, for example, a flexible tubular carrier. Implant unit 710 may also include any elements, such as circuitry, electrical components, materials, and any other features described previously with respect to implant unit 110. Implant unit 710 may include modulation electrodes 758a, 758b configured to facilitate an electric field including field lines extending in the longitudinal direction of the blood vessel. For example, as illustrated in FIG. 15, implant unit 710 may be implanted in a renal artery 711. Implant unit 710 may be located within renal artery 711 in a location in the vicinity of renal nerves 715 surrounding renal artery 711 prior to its entry into kidney 712. As described previously, renal nerves 715 aids in the regulation of the blood pressure in humans. Thus, implant unit 710, located within renal artery 711 in the vicinity of renal nerves 715 may facilitate an electric field configured to modulate renal nerves 715, and, thus, affect the blood pressure of a subject. The illustrated location is exemplary only, and implant unit 710 may be configured in alternate ways suitable for the modulation of renal nerves 715.

Additional embodiments of the present disclosure may include the following. A method of activating neuromuscular tissue with an implanted circuit, comprising: communicating with the implanted circuit, which is implanted within a proximity of a tongue of a subject, wherein the implanted circuit is in electrical communication with at least one electrode; receiving a physiological signal from the subject via the implanted circuit; sending a control signal to the implanted circuit in response to the physiological signal; and activating neuromuscular tissue within the tongue of the subject via the control signal. The control signal may be sent within a response time chosen from among the group comprising 1 second, 500 milliseconds, 200 milliseconds, 100 milliseconds, 50 milliseconds, 20 milliseconds, 5 milliseconds, and 1 millisecond. The physiological signal may be received by a unit located external to the body of the subject, and the control signal is sent from the unit. The physiological signal may include at least one aspect indicative of a movement of the tongue. The movement of the tongue may be detected via a relative motion between an antenna located external to the body of the subject and an antenna associated with the implanted circuit. The method of claim may, further comprise determining, based on the physiologic signal, a quantity of energy to be sent to the implanted circuit via the control signal. The method may further comprise detecting a sleep disordered breathing event based on the physiological signal; and generating the control signal to be sent based on the detected sleep disordered breathing event. Generating the control signal to be sent may include determining a power level for the control signal based on a determined severity of the sleep disordered breathing event. Generating the control signal to be sent may include determining a time duration for the control signal based on a determined severity of the sleep disordered breathing event. The sleep disordered breathing event may be a precursor of sleep apnea. Activating neuromuscular tissue within the tongue may cause the subject's tongue to move in a direction away from a posterior pharyngeal wall of the subject. The physiological signal may be indicative of an efficiency of energy transfer between the housing and the circuit, and generating the control signal to be sent may include determining a power level based on the efficiency of energy transfer and an upper threshold associated with the implant circuit. The physiological signal may be indicative of an efficiency of energy transfer between the housing and the circuit, and generating the control signal to be sent may include determining a power level based on the efficiency of energy transfer and an efficacy threshold associated with the implant circuit.

Additional embodiments of the present disclosure may include the following. A method of modulating a hypoglossal nerve may comprise receiving an alternating current (AC) signal at an implant unit, generating a voltage signal in response to the AC signal, applying the voltage signal to at least one pair of modulation electrodes, the at least one pair of modulation electrodes being configured to be implanted into the body of a subject in the vicinity of the hypoglossal nerve, and generating an electrical field in response to the voltage signal applied to the at least one pair of modulation electrodes to modulate the hypoglossal nerve from a position where the at least one pair of modulation electrodes do not contact the hypoglossal nerve. The AC signal may be received via an antenna associated with the implant unit. The electric field generated by the at least one pair of modulation electrodes may be configured to penetrate tissue in order to induce modulation of the hypoglossal nerve. The tissue may include a genioglossus muscle. The at least one pair of modulation electrodes may be configured such that the generated electric field provides an energy density sufficient to modulate the hypoglossal nerve without contacting the hypoglossal nerve. The voltage signal applied to the at least one pair of modulation electrodes may have a voltage of between about 0.5 volts and about 40 volts. Each of the electrodes of the at least one pair of modulation electrodes may includes surface area of about 0.01 mm$^2$ to about 80 mm$^2$. The electrodes of the at least one pair of modulation electrodes may be separated from one another by a distance of less than about 25 mm.

Alternative embodiments consistent with the present disclosure may include the following. A method of locating an external unit with respect to an implant unit may comprise detecting a distance between the external unit and the implanted unit located beneath the skin of a subject, and producing an indicator signal when the external unit is within a predetermined range of the implant unit, and varying the indicator signal as a function of a distance between the external unit and the implant unit. The indicator signal may include a visual output. The indicator signal may include a tactile output. The indicator signal may include an electrical signal communicated to the implant unit. The electrical signal may cause the implant unit to modulate a nerve and to induce at least one of a proprioceptive or kinesthesic reaction in the subject. The indicator signal may include an audible output. The method may further comprise generating a primary signal on a primary antenna associated with the external unit, the primary signal being configured to cause a secondary signal on a secondary antenna associated with the implant unit, determining a degree of coupling between the primary antenna associated with the external unit and the secondary antenna associated with the implant unit, determining the distance between the external unit and the implant unit based on the degree of coupling, and causing the indicator to produce the indicator signal when the degree of coupling exceeds a predetermined threshold. Determining the degree of coupling between the primary antenna associated with the external unit and the secondary antenna associated with the implant unit may include at least one of determining a degree of capacitive coupling, a degree of radio frequency coupling, or a degree of inductive coupling between the primary antenna and the secondary antenna. The external unit may comprise at least one processor; the at least one processor being configured to generate a primary signal on a primary antenna associated with the external unit, the primary signal being configured to cause a secondary signal on a secondary antenna associated with the implant unit, determine a degree of coupling between the primary antenna associated with the external unit and the secondary antenna associated with the implant unit, and cause the indicator to produce the indicator signal when the degree of coupling does not exceed a predetermined threshold.

A glucose monitoring device for measuring a level of glucose in a subject, the glucose monitoring device may comprise a housing configured for location on a a subject to communicate with an implantable glucose sensor implanted in the subject, and an indicator associated with the housing, wherein the indicator is configured to produce an indicator signal when the housing is within a predetermined range of the implant unit, and wherein the indicator is configured to vary the indicator signal according to a distance between the housing and the implant unit. The housing may comprise at least one processor; the at least one processor being configured to: generate a primary signal on a primary antenna associated with the housing, the primary signal being configured to cause a secondary signal on a secondary antenna associated with the implant unit, determine a degree of coupling between the primary antenna associated with the housing and the secondary antenna associated with the implant unit, and cause the indicator to produce the indicator signal when the degree of coupling exceeds a predetermined threshold, operate in a placement mode and a monitoring mode, cause the indicator to produce the variable signal during operation in the placement mode, and transition from the placement mode to the monitoring mode when a correct placement condition is satisfied. The correct placement condition may include at least one of a predetermined coupling threshold and a predetermined timing threshold. The glucose monitoring device may further comprise a skin patch, wherein the skin patch comprises an adhesive and is configured for adherence to the skin of the subject, wherein the housing is removably connected to the skin patch, and the at least one processor is configured to operate in a placement mode when the housing is connected to the skin patch.

Additional embodiments of the present disclosure may include a method of modulating a nerve via at least one pair of electrodes associated with an implanted circuit and implanted in the vicinity of the nerve. The method may include steps of delivering to the electrodes, via the implanted circuit, an electrical signal having a current less than about 1.6 milliamps and modulating the nerve via the generation of an electrical field between the electrodes by the electrical signal having a current less than about 1.6 milliamps. The method may further include delivering a plurality of electrical signals to the electrodes, wherein each of the plurality of electrical signals has a current less than about 1.6 milliamps. The method may further include, further comprising varying at least one of a voltage, current, or duration of the plurality of electrical signals. The method may further include receiving, via the implantable circuit, energy from a source external to a subject. The method may further include delivering to the electrodes, via the electrical signal having a current less than about 1.6 milliamps, a substantial portion of the energy received from the source external to the subject within about 1 second or less of receiving the energy. The method may further include providing an implantable antenna, in electrical communication with the implantable circuit, for transmitting or receiving electrical signals. The method may further include generating and sending, via a transmitter included in the implantable circuit, a signal indicative of a request that energy be supplied from the source external to the subject. The implantable circuit may be configured for location detection from a location external to the subject. The circuit and the electrodes may be further configured for implantation in a subject on the surface of non-nerve tissue interposed between the electrodes and the nerve. The tissue interposed between the electrodes and the nerve may include at least one of muscle tissue, connective tissue, fat, blood vessel, and mucosal membrane.

Additional embodiments of the present disclosure may include a method for regulating delivery of power to an implant unit. The method may include communicating with the implant unit, which is implanted in a body of a subject, determining a degree of coupling between a primary antenna associated with a power source and a secondary antenna associated with the implant unit, and regulating delivery of power from the power source to the implant unit based on the degree of coupling. The method may further include receiving physiologic data via the implant unit, and regulating delivery of power from the power source to the implant unit based on the physiologic data and the degree of coupling. The upper limit of the power delivered from the power source to the implant unit may be determined according to an upper threshold associated with the implant unit. The lower limit of the power delivered from the power source to the implant unit may be determined according to an efficacy threshold of the power delivered. The power may be delivered from the power source to the implant unit via radiofrequency transmission of an alternating current signal. Regulating delivery of power from the power source to the implant unit may include adjusting at least one of voltage, pulse rate, and current associated with the alternating current signal. The degree of coupling between the primary antenna and the secondary antenna may include a measure of capacitive coupling. The degree of coupling between the primary antenna and the secondary antenna may include a measure of radiofrequency coupling. The degree of coupling between the primary antenna and the secondary antenna may include a measure of inductive coupling. The physiologic data may be representative of a motion of the implant unit.

Additional embodiments of the present disclosure may include a method of delivering electrical stimulation treatment pulses, including generating a primary signal in a primary antenna using power supplied by a battery, wherein the primary antenna is associated with a housing configured to retain the battery, and transmitting the primary signal from the primary antenna to an implantable device during a treatment session of at least three hours in duration, wherein the primary signal includes a pulse train, the pulse train including a plurality of stimulation pulses. The at least one of the plurality of stimulation pulses may include an alternating current signal. The alternating current signal may have a frequency between 6.5 and 13.6 megahertz. The at least one of the plurality of stimulation pulses may include a plurality of stimulation sub-pulses, each stimulation sub-pulse having a duration of between 50 and 250 microseconds. The at least one of the plurality of stimulation pulses may include between 5 and 15 stimulation sub-pulses. The at least one processor may be configured to cause transmission of the primary signal for at least 90% of the treatment session. The battery may have a capacity of less than 240 mAh, less than 120 mAh, and less than 60 mAh. The pulse train may include more than at least one of 5000, 10,000, and 100,000 stimulation pulses. The temporal spacing between a majority of the stimulation pulses may be less than 1.3 seconds. The stimulation pulses occur at a frequency chosen from among four, eight, and sixteen times a breathing frequency. The majority of the stimulation pulses may have a pulse duration of at least 200 milliseconds. At least one of the housing and the primary antenna may be flexible to an extent permitting it to generally conform to the contours of a subject's skin. The implantable device may include at least one pair of stimulation electrodes, and may be configured to cause a muscular contraction inducing current at the at least one pair of stimulation electrodes when the primary signal is received by the implantable device. The stimulation pulses may be temporally spaced so as not to permit a complete relaxation of a muscle after muscular contraction.

Additional embodiments of the present disclosure may include the following. A method of transmitting signals to an implantable device may comprise determining one or more sub-modulation characteristics of a sub-modulation control signal so as not to cause a neuromuscular modulation inducing current across at least one pair of modulation electrodes in electrical communication with an implantable device when the sub-modulation control signal is received by the implantable device, determining one or ore modulation characteristics of a modulation control signal so as to cause a neuromuscular modulation inducing current across at least one pair of modulation electrodes in electrical communication with the implantable device when the modulation control signal is received by the implantable device, generating the modulation control signal having the one or more modulation characteristics, generating the sub-modulation control signal having the one or more sub-modulation characteristics, transmitting, via the primary antenna, the modulation control signal to a secondary antenna associated with the implantable device, and transmitting, via the primary antenna, the sub-modulation control signal to a secondary antenna associated with the implantable device. The method may further comprise receiving via the primary antenna a condition signal from the implantable device. The condition signal may be indicative of at least one of movement of the implantable device, a location of the implantable device, a maximum power limit of the implantable device, and a minimum efficacy threshold of the device. The one or more modulation characteristics of the modulation control signal and the one or more sub-modulation characteristics of the sub-modulation control signal may include at least one of a voltage, current, frequency, pulse rate, pulse width, and duration. Transmission of at least one of modulation signal and the sub-modulation signal may be triggered by the condition signal indicative of a predetermined amount of movement of the implantable device. Movement of the implantable device may be indicative of an amount of tongue movement associated with sleep disordered breathing and the amount of tongue movement may be indicative of a severity of the sleep disordered breathing. The condition signal may be indicative of a degree of coupling between the primary antenna and a secondary antenna associated with the implantable device, the degree of coupling relating to at least one of a level of radiofrequency coupling, a level of inductive coupling, and a measure of harmonic resonance. The sub-modulation characteristics of the sub-modulation control signal may be determined so as to elicit the condition signal from the implantable device. The method may further comprise adjusting at least one of the one or more modulation characteristics of the modulation control signal and the one or more sub-modulation characteristics of the sub-modulation control signal based on the condition signal.

Additional embodiments consistent with the present disclosure may include the following. A device, including an implantable flexible carrier, an implantable circuit, and, a pair of electrodes located on the carrier and in electrical communication with the implantable circuit. The electrodes may be configured to cause, when supplied with an electrical signal via the implantable circuit, a unidirectional electrical field. The pair of electrodes may be further configured to modulate the at least one nerve when non-nerve tissue is interposed between the electrodes and the at least one nerve. The electrodes may be configured with a spacing distance such that the unidirectional electrical field is sufficient to modulate at least one nerve located greater than 1 mm away from the electrodes. The flexible carrier may include attachment points configured for securing the flexible carrier to a surface of the non-nerve tissue. The flexible carrier may comprise an insulative coating, and the electrodes may be exposed on one side of the flexible carrier. The device may further include at least one pair of additional electrodes. The device may further include an antenna in electrical communication with the implantable circuit, wherein the antenna is adapted to receive a transmitted alternating current signal and a converter configured to convert the alternating current signal into a direct current signal for delivery to the at least one pair of implantable electrodes. The implantable circuit may located on the flexible carrier, and the antenna may be located on the flexible carrier.

Additional embodiments of the present disclosure may include the following. A sleep disordered breathing therapy implant unit may comprise a flexible carrier, at least one pair of modulation electrodes on the flexible carrier, and at least one implantable circuit in electrical communication with the at least one pair of modulation electrodes, wherein the at least one pair of modulation electrodes and the at least one circuit are configured for implantation through derma on an underside of a subject's chin, and wherein the implantable circuit and the electrodes are configured to cooperate in order to generate an electric field adapted to cause modulation of at least a portion of the subject's hypoglossal nerve through application of an electric field to a section of the hypoglossal nerve distal of a terminal bifurcation to lateral and medial branches of the hypoglossal nerve. The at least one pair of modulation electrodes may be configured to cause modulation of at least a portion of the medial branch of the hypoglossal nerve. The at least one pair of modulation electrodes may be configured to cause modulation of one or more terminal branches of the medial branch of the hypoglossal nerve.

Additional embodiments of the present disclosure may include a method for delivering power to an implanted circuit including communicating with the implanted circuit, which is implanted in a body of a subject, and transmitting power to the implanted circuit in a first power mode and in a second power mode, wherein a first level of power delivered in the first power mode is less than a second level of power delivered in the second power mode, and wherein during a therapy period, power delivery in the first power mode occurs over a total time that is greater than about 50% of the therapy period. The implanted circuit may be associated with electrodes, and during the first power mode, transmitting power may include transmitting a first alternating current signal to supply power to the implant circuit while the implant circuit is substantially restricted from supplying direct current to the electrodes, and during the second power mode, transmitting power may include transmitting a second alternating current signal to supply power to the implant circuit for conversion to direct current to be supplied to the electrodes. The implant circuit may be substantially restricted from supplying direct current to the electrodes by a diode. During the first power mode, the first alternating current signal may be transmitted at a lower voltage than the second alternating current signal transmitted during the second power mode. The implant circuit may be associated with electrodes, and transmitting power may include transmitting an alternating current signal to the implant circuit for conversion to direct current to be supplied to the electrodes, and during the first power mode, a first power mode pulse length of the alternating current signal may be shorter than a pulse length required to cause neural modulation through the electrodes associated with the implant circuit, and during the second power mode, a second power mode pulse length of the alternating current signal may be at least as long as the pulse length required to cause neural modulation through the electrodes associated with the implant circuit. The first power mode pulse length may be less than 500 nanoseconds, and the second power mode pulse length may be greater than 50 microseconds. The first power mode pulse length may be less than 50 microseconds, and the second power mode pulse length may be greater than 50 microseconds. The implant circuit may be associated with electrodes, and transmitting power may include transmitting an alternating current signal to the implant circuit for conversion to direct current to be supplied to the electrodes, and during the first power mode, a first power mode current amplitude of the alternating current signal may be lower than a current amplitude required to cause neural modulation through the electrodes associated with the implant circuit, and during the second power mode, a second power mode current amplitude of the alternating current signal may be at least as great as a current amplitude required to cause neural modulation through the electrodes associated with the implant circuit. The total time of power delivery in the first mode may be greater than about 90 of the therapy period. The total time of power delivery in the first mode may be greater than about 95% of the therapy period.

Additional embodiments of the present disclosure may include the following. A sleep disordered breathing therapy implant unit may comprise a flexible carrier, at least one pair of modulation electrodes on the flexible carrier, and at least one implantable circuit in electrical communication with the at least one pair of modulation electrodes, wherein the at least one pair of modulation electrodes and the at least one circuit are configured for implantation through derma on an underside of a subject's chin, and wherein the implantable circuit and the electrodes are configured to cooperate in order to generate an electric field adapted to cause modulation of at least a portion of the subject's hypoglossal nerve through application of an electric field to a section of the hypoglossal nerve distal of a terminal bifurcation to lateral and medial branches of the hypoglossal nerve. The at least one pair of modulation electrodes may be configured to cause modulation of at least a portion of the medial branch of the hypoglossal nerve. The at least one pair of modulation electrodes may be configured to cause modulation of one or more terminal branches of the medial branch of the hypoglossal nerve.

Other embodiments of the present disclosure will be apparent to those skilled in the art from consideration of the specification and practice of the present disclosure.

While this disclosure provides examples of the neuromodulation devices employed for the treatment of certain conditions, usage of the disclosed neuromodulation devices is not limited to the disclosed examples. The disclosure of uses of embodiments of the invention for neuromodulation are to be considered exemplary only. In its broadest sense, the invention may be used in connection with the treatment of any physiological condition through neuromodulation. Alternative embodiments will become apparent to those skilled in the art to which the present invention pertains without departing from its spirit and scope. Accordingly, the scope of the present invention is defined by the appended claims rather than the foregoing description.

What is claimed is:

1. A system for the treatment of sleep apnea, the system comprising:
   a flexible carrier;
   at least one pair of stimulation electrodes disposed on the carrier; and
   a neurostimulation device configured to transfer power to the at least one pair of stimulation electrodes;
   wherein the flexible carrier is configured for location proximate to a genioglossus muscle of a subject such that the at least one pair of stimulation electrodes cause dilation of an airway of the subject solely through stimulation of a portion of the subject's hypoglossal nerve through application of an electric field to a single section of a medial branch of the hypoglossal nerve distal of a terminal bifurcation of the hypoglossal nerve into lateral and medial branches.

2. The system of claim 1, wherein at least a portion of the flexible carrier is configured to be located between the genioglossus muscle and an adjacent muscle.

3. The system of claim 2, wherein the adjacent muscle is a mylohyoid muscle.

4. The system of claim 1, wherein at least a portion of the flexible carrier is configured to be located at a position between the genioglossus muscle and the geniohyoid muscle.

5. The system of claim 1, wherein the at least one pair of stimulation electrodes are spaced apart by a distance of 1 mm to 10 mm.

6. The system of claim 1, wherein the at least one pair of stimulation electrodes are configured to provide stimulation using less than 1.6 milliamps of current.

7. The system of claim 1, wherein the at least one pair of stimulation electrodes are configured to generate an electric field having electric field lines that run partially or substantially parallel to nerve fibers of the medial branch of the hypoglossal nerve.

8. The system of claim 2, wherein the flexible carrier is configured to position the at least one pair of stimulation electrodes to stimulate terminal fibers of the medial branch.

\* \* \* \* \*